(12) United States Patent
Hong et al.

(10) Patent No.: US 11,588,113 B2
(45) Date of Patent: Feb. 21, 2023

(54) ORGANIC LIGHT EMITTING DIODE AND ORGANIC LIGHT EMITTING DEVICE HAVING THE SAME

(71) Applicants: LG Display Co., Ltd., Seoul (KR); LG CHEM, LTD., Seoul (KR)

(72) Inventors: Tae-Ryang Hong, Paju-si (KR); Hyong-Jong Choi, Paju-si (KR); Jun-Yun Kim, Paju-si (KR); Wan-Pyo Hong, Daejeon (KR); Jin-Joo Kim, Daejeon (KR); Hong-Sik Yoon, Seoul (KR)

(73) Assignees: LG DISPLAY CO., LTD., Seoul (KR); LG CHEM, LTD., Seoul (KR)

( * ) Notice: Subject to any disclaimer, the term of this patent is extended or adjusted under 35 U.S.C. 154(b) by 778 days.

(21) Appl. No.: 16/518,414

(22) Filed: Jul. 22, 2019

(65) Prior Publication Data

US 2020/0136059 A1 Apr. 30, 2020

(30) Foreign Application Priority Data

Oct. 25, 2018 (KR) ........................ 10-2018-0128298

(51) Int. Cl.
*H01L 51/00* (2006.01)
*C07D 409/14* (2006.01)
(Continued)

(52) U.S. Cl.
CPC ........ *H01L 51/0072* (2013.01); *C07D 405/14* (2013.01); *C07D 409/14* (2013.01); *C09K 11/06* (2013.01); *H01L 51/0073* (2013.01); *H01L 51/0074* (2013.01); *C09K 2211/1018* (2013.01); *H01L 51/5004* (2013.01); *H01L 51/5016* (2013.01); *H01L 51/5278* (2013.01); *H01L 2251/5376* (2013.01); *H01L 2251/552* (2013.01)

(58) Field of Classification Search
CPC .......................... H01L 51/504; H01L 51/5278
See application file for complete search history.

(56) References Cited

U.S. PATENT DOCUMENTS

| 2008/0203406 A1 | 8/2008 | He et al. |
| 2016/0056393 A1* | 2/2016 | Oikawa ............... H01L 51/5016 548/440 |
| 2018/0090705 A1 | 3/2018 | Kim et al. |

FOREIGN PATENT DOCUMENTS

| CN | 107887516 A | 4/2018 |
| CN | 108218834 A | 6/2018 |
| KR | 10-2018-0035528 A | 4/2018 |

* cited by examiner

*Primary Examiner* — Jennifer A Boyd
*Assistant Examiner* — Sean M DeGuire
(74) *Attorney, Agent, or Firm* — Birch, Stewart, Kolasch & Birch, LLP

(57) ABSTRACT

Disclosed is an organic light emitting diode (OLED) includes a first emitting material layer, which includes a first compound and a second compound, and a second emitting material layer, which includes a third compound and a fourth compound, wherein a HOMO energy level of the first compound is higher than a HOMO energy level of the second compound and a HOMO energy level of the third compound is lower than a HOMO energy level of the fourth compound, and an organic light emitting device having the OLED. The OLED and the organic light emitting device disclosed have enhanced luminous efficiency, color purity and luminous life span as well as low driving voltage by applying the emitting material layer.

12 Claims, 8 Drawing Sheets

(51) Int. Cl.
*C09K 11/06* (2006.01)
*C07D 405/14* (2006.01)
*H01L 51/50* (2006.01)
*H01L 51/52* (2006.01)

ORGANIC LIGHT EMITTING DIODE AND ORGANIC LIGHT EMITTING DEVICE HAVING THE SAME

CROSS-REFERENCE TO RELATED APPLICATIONS

This application claims the benefit under 35 U.S.C. § 119(a) of Korean Patent Application No. 10-2018-0128298, filed in Korea on Oct. 25, 2018, which is incorporated herein by reference in its entirety.

BACKGROUND

Technical Field

The present disclosure relates to an organic light emitting diode, and more specifically, to an organic light emitting diode with superior luminous efficiency, color purity and luminous life span and an organic light emitting device including the same.

Description of the Related Art

As a display device becomes larger, there exists a need for a flat display device with reduced size. Among the flat display devices, a display device using an organic light emitting diode (OLED) has come into the spotlight.

In the OLED, when electrical charges are injected into an emitting layer between an electron injection electrode (i.e., cathode) and a hole injection electrode (i.e., anode), electrical charges are combined to be paired, and then emit light as the combined electrical charges are canceled.

The OLED can be formed on a flexible transparent substrate such as a plastic substrate. In addition, the OLED can be driven at a lower voltage of 10 V or less. Moreover, the OLED has relatively lower power consumption for driving compared to the plasma display panel and inorganic electroluminescent devices, and color purity of the OLED is very high. Further, since the OLED can display various colors such as green, blue, red and the like, the OLED display device has attracted a lot of attention as a next-generation display device that can replace a liquid crystal display device (LCD).

BRIEF SUMMARY

Accordingly, the present disclosure is directed to an organic light emitting diode and an organic light emitting device including the diode that substantially decreases one or more of the problems due to the limitations and disadvantages of the related art.

An object of the present disclosure is to provide an organic light emitting diode and an organic light emitting device that can enhance luminous efficiency and color purity.

Another object of the present disclosure is to provide an organic light emitting diode and an organic light emitting device with lower driving voltage and power consumption, and improves the OLED luminous life span.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

According to an aspect, the present disclosure provides an organic light emitting diode (OLED) that comprises first and second electrodes facing each other, and an emitting material layer disposed between the first and second electrodes, wherein the emitting material layer includes a first emitting material layer including a first compound and a second compound and a second emitting material layer including a third compound and a fourth compound, wherein an excited state singlet energy level of the first compound is higher than an excited state singlet energy level of the second compound, wherein each of an excited state singlet energy level and an excited state triplet energy level of the third compound is higher than each of an excited state singlet energy level and an excited state triplet energy level of the fourth compound, respectively, wherein a Highest Occupied Molecular Orbital (HOMO) energy level of the first compound is higher than a HOMO energy level of the second compound, and wherein a HOMO energy level of the third compound is lower than a HOMO energy level of the fourth compound.

According to another aspect, the present disclosure provides an OLED, comprising, first and second electrodes facing each other; and an emitting material layer disposed between the first and second electrodes, wherein the emitting material layer includes a first emitting material layer including a first compound and a second compound and a second emitting material layer including a third compound and a fourth compound, wherein an excited state singlet energy level of the first compound is higher than an excited state singlet energy level of the second compound, wherein each of an excited state singlet energy level and an excited state triplet energy level of the third compound is higher than each of an excited state singlet energy level and an excited state triplet energy level of the fourth compound, respectively, wherein a Highest Occupied Molecular Orbital (HOMO) energy level of the first compound is higher than a HOMO energy level of the second compound, and wherein the third compound includes an organic compound having the following structure of Chemical Formula 3:

Chemical Formula 3

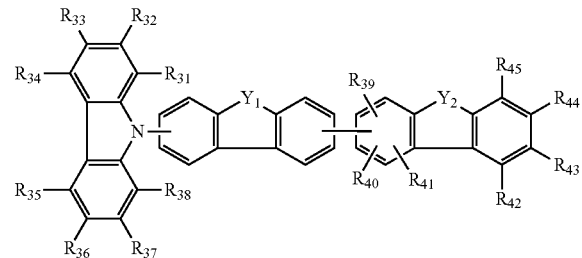

wherein each of $R_{31}$ to $R_{45}$ is independently hydrogen, deuterium, tritium, silyl group, $C_1$~$C_{10}$ alkyl group, $C_1$~$C_{10}$ alkoxy group, $C_1$~$C_{10}$ alkyl amino group, $C_5$~$C_{30}$ aryl group, $C_4$~$C_{30}$ hetero aryl group, $C_5$~$C_{30}$ alkyl aryl group, $C_4$~$C_{30}$ hetero alkyl aryl group, $C_5$~$C_{30}$ aryloxyl group, $C_4$~$C_{30}$ hetero aryloxyl group, $C_5$~$C_{30}$ aryl amino group or $C_4$~$C_{30}$ hetero aryl amino group, or two adjacent groups among $R_{31}$ to $R_{45}$ forms a fused aryl ring or a fused hetero aryl ring each of which is unsubstituted or substituted with $C_5$~$C_{30}$ aryl group or $C_4$~$C_{30}$ hetero aryl group; each of $Y_1$ and $Y_2$ is independently $NR_{46}$, oxygen (O) or sulfur (S), wherein $R_{46}$ is hydrogen, deuterium, tritium, $C_1 \sim C_{20}$ alkyl group or $C_1 \sim C_{20}$ alkoxy group.

According to still another aspect, the present disclosure provides an organic light emitting device that comprises a substrate and the OLED disposed over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Reference will now be made in detail to aspects of the disclosure, examples of which are illustrated in the accompanying drawings.

Organic Light Emitting Device

Figure 1:
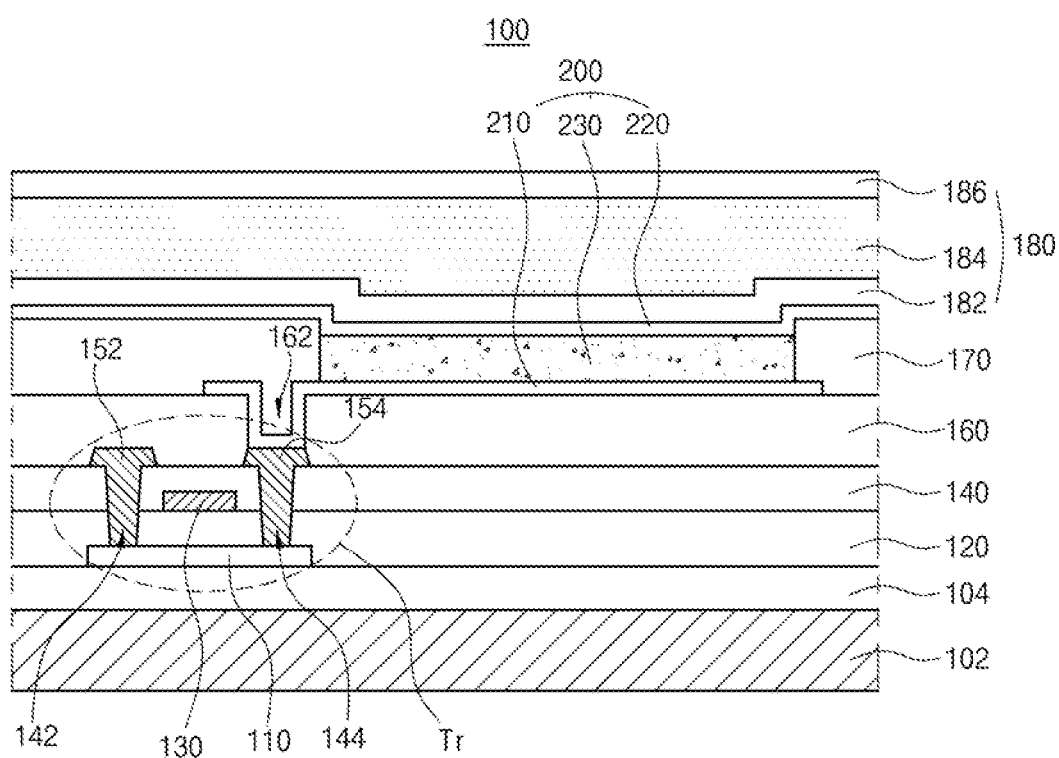
FIG. 1 is a schematic cross-sectional view illustrating an organic light emitting display device of the present disclosure.

The present disclosure relates to an organic light emitting diode (OLED) that includes multiple emitting material layers each of which has luminous materials whose energy levels are controlled within predetermined ranges so as to enhance charge transportations and to inhibit exciton quenching among the luminous materials, and an organic light emitting device having the OLED. The OLED of the present disclosure may be applied to an organic light emitting device such as an organic light emitting display device and an organic light emitting illumination device. A display device having the OLED of the present disclosure will be explained. FIG. 1 is a schematic cross-sectional view illustrating an organic light emitting display device of the present disclosure.

As illustrated in FIG. 1, the organic light emitting display device 100 comprises a substrate 102, a thin-film transistor Tr on the substrate 102, and an organic light emitting diode 200 connected to the thin film transistor Tr. The thin-film transistor Tr includes a semiconductor layer 110, a gate electrode 130, a source electrode 152 and a drain electrode 154.

The substrate 102 may include, but are not limited to, glass, thin flexible material and/or polymer plastics. For example, the flexible material may be selected from the group, but are not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode 200 are arranged, form an array substrate.

A buffer layer 104 may be disposed over the substrate 102, and, when the buffer layer 104 is present, the thin film transistor Tr is disposed over the buffer layer 104. The buffer layer 104 may be omitted.

A semiconductor layer 110 is disposed over the buffer layer 104. In one exemplary embodiment, the semiconductor layer 110 may include oxide semiconductor materials. In this case, a light-shield pattern may be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 may include, but are not limited to, polycrystalline silicon. In this case, opposite edges of the semiconductor layer 110 may be doped with impurities.

A gate insulating layer 120 formed of an insulating material is disposed on the semiconductor layer 110. The gate insulating layer 120 may include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 formed of an insulating material is disposed on the gate electrode 130 with covering over an entire surface of the substrate 102. The interlayer insulating layer 140 may include, but are not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over both sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, each of which is made of a conductive material such as a metal, are disposed on the interlayer insulating layer 140. The source electrode 152 and the drain electrode 154 are spaced apart from each other with respect to the gate electrode 130 and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and source and drain electrodes are disposed over the semiconductor layer. In this case, the semiconductor layer may include, but are not limited to, amorphous silicon.

Although not shown in FIG. 1, a gate line and a data line, which cross each other to define a pixel region, and a switching element, which is connected to the gate line and the data line, may be further formed in the pixel region. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter for absorbing a part of the light emitted from the organic light emitting diode 200. For example, the color filter may absorb a light of specific wavelength such as red (R), green (G) or blue (B). In this case, the organic light emitting display device 100 can implement full-color through the color filter.

For example, when the organic light emitting display device 100 is a bottom-emission type, the color filter may be disposed on the interlayer insulating layer 140 with corresponding to the organic light emitting diode 200. Alternatively, when the organic light emitting display device 100 is a top-emission type, the color filter may be disposed over the organic light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 154, it may be spaced apart from the second semiconductor layer contact hole 154.

The organic light emitting diode 200 includes a first electrode 210 that is disposed on the passivation layer 160 and connected to the drain electrode 154 of the thin-film transistor Tr. The organic light emitting diode 200 further includes an emitting unit 230 as an emission layer and a second electrode 220 each of which is disposed sequentially on the first electrode 210.

The first electrode 210 is disposed in each pixel region. The first electrode 210 may be an anode and include, but are not limited to, a conductive material having a relatively high work function value. For example, the first electrode 610 may include, but are not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the likes.

In one exemplary embodiment, when the organic light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

The emitting unit 230 as an emission layer is disposed on the first electrode 210. In one exemplary embodiment, the emitting unit 230 may have a mono-layered structure of an emitting material layer. Alternatively, the emitting unit 230 may have a multiple-layered structure of at least one charge control or transfer layer, for controlling charge transport, such as a hole injection layer, a hole transport layer, an electron blocking layer, a hole blocking layer, an electron transport layer and/or an electron injection layer as well as an emitting material layer (see, FIGS. 2 and 6). As an example, the organic light emitting diode 200 may have multiple emitting units and at least one charge generation layer disposed between two adjacent emitting units. The emitting unit 230 may include multiple emitting material layers having luminous materials whose energy levels are controlled within predetermined ranges. The construction and energy levels of those luminous materials will be explained in more detail below.

The second electrode 220 is disposed over the substrate 102 above which the emitting unit 230 is disposed. The second electrode 220 may be disposed over a whole display area and may include, but are not limited to, a conductive material having a relatively low work function value compared to the first electrode 210. The second electrode 220 may be a cathode. For example, the second electrode 220 may include, but are not limited to, aluminum (Al), magnesium (Mg), calcium (Ca), silver (Au), alloy thereof or combination thereof such as aluminum-magnesium alloy (Al—Mg).

In addition, an encapsulation film 180 may be disposed over the second electrode 220 in order to prevent outer moisture from penetrating into the organic light emitting diode 200. The encapsulation film 180 may have, but are not limited to, a laminated structure of a first inorganic insulating film 182, an organic insulating film 184 and a second inorganic insulating film 186.

The emitting unit 230 includes a first emitting material layer includes a first compound and a second compound, a second emitting material layer includes a third compound and a fourth compound, and optionally a third emitting material layer includes a fifth compound and a sixth compound. It is possible to luminous efficiency and color purity and luminous life span owing to reduced driving voltage of the OLED 200 and the organic light emitting display device 100 by adjusting energy levels and/or energy level bandgap among those compounds as luminous materials.

Organic Light Emitting Diode (OLED)

Figure 2:
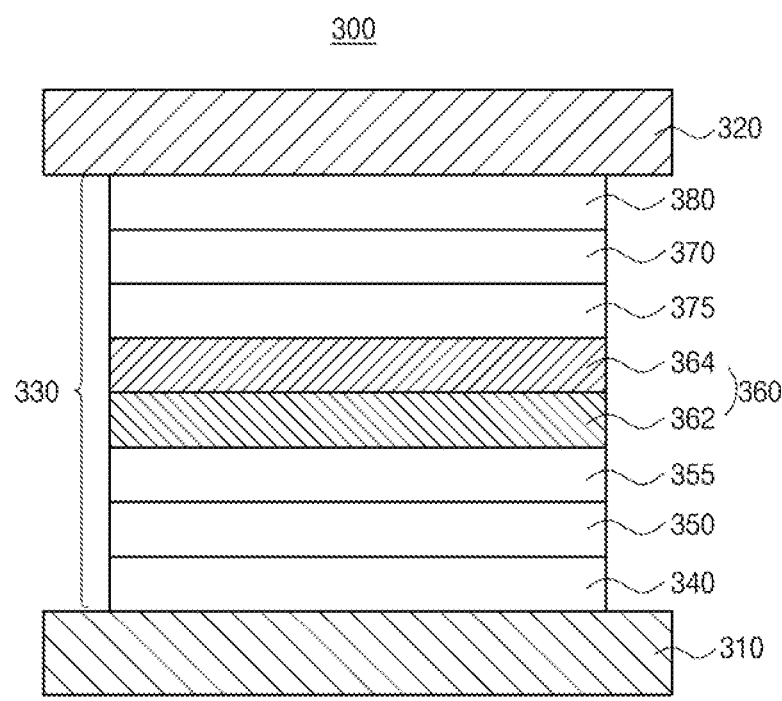
FIG. 2 is a schematic cross-sectional view illustrating an organic light emitting diode in accordance with an exemplary embodiment of the present disclosure.

An organic light emitting diode including multiple-layered emitting material layer will be explained. FIG. 2 is a schematic cross-sectional view illustrating an organic light emitting diode in accordance with an exemplary embodiment of the present disclosure.

As illustrated in FIG. 2, the organic light emitting diode (OLED) 300 in accordance with an exemplary embodiment of the present disclosure includes first and second electrodes 310 and 320 facing each other, and an emitting unit 330 as an emission layer disposed between the first and second electrodes 310 and 320. In one exemplary embodiment, the emitting unit 330 includes a hole injection layer (HIL) 340, a hole transport layer (HTL) 350, an emitting material layer (EML) 360, an electron transport layer (ETL) 370 and an electron injection layer (EIL) 380 each of which is laminated sequentially from the first electrode 310. Alternatively, the emitting unit 330 may further include a first exciton blocking layer, i.e. an electron blocking layer (EBL) 355 disposed between the HTL 350 and the EML 360 and/or a second exciton blocking layer, i.e. an hole blocking layer (EBL) 375 disposed between the EML 360 and the ETL 370.

The first electrode 310 may be an anode that provides a hole into the EML 360. As described above, the first electrode 310 may include, but are not limited to, a conductive material having a relatively high work function value, for example, a transparent conductive oxide (TCO). In an exemplary embodiment, the first electrode 110 may include, but are not limited to ITO, IZO, ITZO, SnO, ZnO, ICO, AZO, and the like.

The second electrode 320 may be a cathode that provides an electron into the EML 360. As described above, the second electrode 320 may include, but is not limited to, a conductive material having a relatively low work function values, i.e., a highly reflective material such as Al, Mg, Ca, Ag, alloy thereof, combination thereof, and the likes. As an example, each of the first electrode 310 and the second electrode 320 may have a thickness of, but are not limited to, about 30 nm to about 300 nm.

The HIL 340 is disposed between the first electrode 310 and the HTL 350 and improves an interface property between the inorganic first electrode 310 and the organic HTL 350. In one exemplary embodiment, the HIL 340 may include, but are not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 340 may be omitted in compliance with a structure of the OLED 300.

The HTL 350 is disposed adjacently to the EML 360 between the first electrode 310 and the EML 360. In one exemplary embodiment, the HTL 350 may include, but are not limited to, N,N'-Diphenyl-N,N'-bis(3-methylphenyl)-1, 1'-biphenyl-4,4'-diamine (TPD), NPB, 4,4'-bis(N-carbazolyl)-1,1'-biphenyl (CBP), Poly[N,N'-bis(4-butylpnehyl)-N,N'-bis(phenye-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary embodiment, each of the HIL 340 and the HTL 350 may be respectively laminated with a thickness of, but are not limited to, about 5 nm to about 200 nm, preferably about 5 nm to about 100 nm.

The EML 360 includes hosts each of which is doped with a dopant where substantial illumination occurs. Phosphorescent materials, which utilize triplet exciton as well as singlet exciton, show higher luminous efficiency than fluorescent materials, which utilize only the singlet exciton. Accordingly, phosphorescent hosts that can be used with phosphorescent dopants have attracted a lot of attentions.

An excited state triplet energy level of the phosphorescent host must be higher than an excited stated triplet energy level of the phosphorescent dopant so as to prevent the triplet energy of the phosphorescent dopant from transferring to the phosphorescent host. The triplet energy of the organic aromatic compounds drops sharply as the organic aromatic compounds have increased conjugation structure or fused rings. Accordingly, the organic materials that can be used as the phosphorescent hosts are extremely limited.

In addition, the phosphorescent hosts are designed to have an energy level bandgap larger than 3.5 to 4.5 eV in order to obtain a high triplet energy level. When a phosphorescent host having excessively wide energy level bandgap is used, charge injection and charge transportation become poor, and therefore, a high driving voltage is required, which may adversely affect on life span properties of the diode.

According to the first embodiment of the present disclosure, the EML 360 includes a first EML (EML1) 362 including a first compound and a second compound, and a second EML (EML2) 364 including a third compound and a fourth compound. In one exemplary embodiment, the first compound may be a first host and the second compound may be a fluorescent or phosphorescent material in the EML1 362. The third compound may be a second host and the fourth compound may be a delayed fluorescent material in the EML2 364. As an example, the first compound may be a fluorescent host and the third compound may be a phosphorescent host.

It is possible to realize the OLED 300 having low driving voltage, excellent luminous efficiency and color purity and improved luminous life span by applying the first to fourth compounds whose singlet energy levels $S_1$, triplet energy levels $T_1$, a Highest Occupied Molecular Orbital (HOMO) energy levels and/or a Lowest Unoccupied Molecular Orbital (LUMO) energy levels are controlled within predetermined ranges. Hereinafter, the OLED 300, where the first compound is the first host "$H_1$", the second compound is the fluorescent dopant "FD", the third compound is the second host "$H_2$", and the fourth compound is a thermally activated delayed fluorescent dopant "TD", will be explained in detail.

An organic light emitting diode (OLED) emits light as holes injected from the anode and electrons injected from the cathode are combined to form excitons in an EML and then unstable excited state excitons return to a stable ground state. The external quantum efficiency (EQE; $\eta_{ext}$) of the luminous material applied into the EML may be calculated by product of four parameters, i.e. exciton generation efficiency or singlet-triplet ratio "$\eta_{S/T}$", a charge balance factor "r", radiative quantum efficiency "Φ" and out-coupling efficiency "$\eta_{out-coupling}$".

The singlet-triplet ratio has maximum value of 0.25 in case of fluorescent materials. Theoretically, when electrons meet holes to form exciton, a singlet exciton of a paired spin and a triplet exciton of an unpaired spin are generated by a ratio of 1:3 by spin arrangements. Only the singlet exciton among the excitons can be involved in emission process and the triplet exciton cannot be involved in the emission process in case of the fluorescent materials.

Charge balance factor "r" is a balance between holes and electrons both of which form excitons and generally has a value of "1" assuming 1:1 matching of 100%. "Φ" is a value related with luminous efficiency of actual luminous materials and depends upon photoluminescence of dopant in a host-dopant system.

"$\eta_{out\text{-}coupling}$" is a ratio of light extracted outwardly among the emitted light in a luminous materials. When isotropic luminous material is thermally deposited to form a thin film, each of luminous molecules does not have specific orientation, but exists with random states. The out-coupling efficiency in such random orientation is generally assumed "0.2". Accordingly, when combining 4 parameters, the OLED may exhibit at most 5% luminous efficiency in case of using the prior art fluorescent material.

In contrast, phosphorescent materials adopt different luminous mechanism of converting both singlet excitons and triplet exciton into light. The phosphorescent materials convert singlet excitons into triplet excitons through inter-system crossing (ISC). Therefore, it is possible to enhance luminous efficiency when the phosphorescent materials, which use the triplet excitons as well as the singlet excitons during the luminous process, are used as luminous materials, compared to using the fluorescent materials.

When metal complexes having a heavy metal such as Ir, Pt, and the likes is utilized as the phosphorescent materials, it is possible to convert triplet state to singlet state through strong spin-orbital bonds by the heavy metal. However, the prior art phosphorescent materials do not have enough color purity for the display device and exhibit very short luminous lifespan, and therefore, they have not been used in commercial display devices.

Delayed fluorescent material has been developed for solving the problems caused by the prior art fluorescent and phosphorescent materials. Representative delayed fluorescent materials utilize thermally activated delayed fluorescence (TADF) mechanism. The delayed fluorescent material enables intramolecular charge transfer and can utilize triplet exciton energy as well as singlet exciton energy during the emission process, and therefore can enhance luminous efficiencies.

Figure 3:
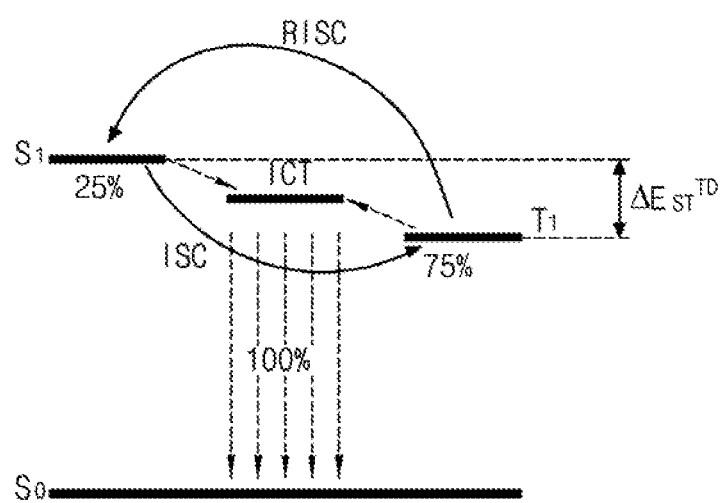
FIG. 3 is a schematic diagram illustrating luminous mechanism of the delayed fluorescent material in accordance with an exemplary embodiment of the present disclosure.

FIG. 3 is a schematic diagram illustrating luminous mechanism by a delayed fluorescent material in an EML in accordance with an exemplary embodiment of the present disclosure.

The delayed fluorescence can be divided into a thermally activated delayed fluorescence (TADF) and a filed activated delayed fluorescence (FADF). Triplet exciton in the delayed fluorescent material can be activated by heat or electrical field so that super-fluorescence beyond the maximal luminous efficiency by conventional fluorescent material can be realized.

Since the triplet excitons within the delayed fluorescent material can be activated by heat or electrical field generated in driving the OLED, the triplet excitons of the delayed fluorescent material can be involved in emission processes. Since the delayed fluorescent material generally has an electron donor moiety as well as an electron acceptor moiety, it can be converted to an intramolecular charge transfer (ICT) state. In case of using the delayed fluorescent material, which can be converted to an ICT state, as a dopant, the excitons of singlet energy level $S_1$ as well as the excitons of triplet energy level $T_1$ can move to an intermediate energy level state, i.e. ICT state, and then the intermediated stated excitons can be transferred to a ground state $(S_0; S_1 \rightarrow ICT \leftarrow T_1)$. Since the excitons of singlet energy level $S_1$ as well as the excitons of triplet energy level $T_1$ in the delayed fluorescent material is involved in the emission process, the delayed fluorescent material can improve internal quantum efficiency and luminous efficiency.

Since both the Highest Occupied Molecular Orbital (HOMO) and the Lowest Unoccupied Molecular Orbital (LUMO) are widely distributed over the whole molecule within the common fluorescent material, it is not possible to inter-convert between the singlet energy level and the triplet energy level within their own molecules (selection rule). In contrast, since the delayed fluorescent material, which can be converted to ICT state, has little orbital overlaps between HOMO and LUMO, there is little interaction between the HOMO state molecular orbital and the LUMO state molecular orbital within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As there is little interaction between HOMO molecular orbital and LUMO molecular orbital in the molecule having the dipole moment of the polarized state, the triplet energy level excitons as well as the singlet energy level excitons can be converted to ICT state. Accordingly, the excitons of triplet energy level $T_1$ as well as the excitons of singlet energy level $S_1$ can participate in the emission process.

In case of driving an OLED that includes the delayed fluorescent material, 25% excitons of singlet energy level $S_1$ and 75% excitons of triplet energy level $T_1$ are converted to ICT state by heat or electrical field, and then the converted excitons at ICT state transfers to the ground state $S_0$ with luminescence. Therefore, the delayed fluorescent material may have 100% internal quantum efficiency in theory.

The delayed fluorescent material must have an energy level bandgap $\Delta E_{ST}^{TD}$ equal to or less than about 0.3 eV, for example, from about 0.05 to about 0.3 eV, between the singlet energy level $S_1$ and the triplet energy level $T_1$ so that exciton energy in both the singlet energy level and the triplet energy level can be transferred to the ICT state. The material having little energy level bandgap between the singlet energy level $S_1$ and the triplet energy level $T_1$ can exhibit common fluorescence with Inter System Crossing (ISC) in which the excitons of singlet energy level $S_1$ can be transferred to the excitons of triplet energy level $T_1$, as well as delayed fluorescence with Reverse Inter System Crossing (RISC) in which the excitons of triplet energy level $T_1$ can be transferred upwardly to the excitons of single energy level $S_1$, and then the exciton of singlet energy level $S_1$ can be transferred to the ground state $S_0$.

Since the delayed fluorescent material can exhibit 100% internal quantum efficiency in theory, it can realize high luminous efficiency as the conventional phosphorescent material including the heavy metal. However, due to the bond conformation between the electron acceptor-electron donor and the sterical twists in the delayed fluorescent material, and additional charge transfer transition (CT transition) caused by them, the delayed fluorescent material shows broad spectrum in the course of emission, i.e. broad full width at half maximum (FWHM), which results in poor color purity. In addition, the fluorescent material exhibits short luminous life span owing to utilizing the triplet exciton energy as well as the singlet exciton energy.

When a delayed fluorescent material and a fluorescent or phosphorescent material are included in a single-layered EML, the delayed fluorescent material is illuminated by RISC and the exciton energy of the delayed fluorescent material is transferred to the fluorescent or phosphorescent material through Dexter resonance energy transfer (DRET) mechanism, which transfers energy by exciton diffusions through intermolecular electron exchanges. In this case, the exciton energy is not sufficiently transferred from the delayed fluorescent material to the fluorescent or phosphorescent material, and the luminous efficiency and color purity may not be achieved to a desired level.

As described above, in one exemplary embodiment of the present disclosure, the EML 360 has a multiple-layered structure. Particularly, the EML1 362 includes the first compound, i.e. the first host and a second compound, i.e. the fluorescent or phosphorescent material, and the EML2 364 includes the third compound, i.e. the second host and the fourth compound, i.e. the delayed fluorescent material. Accordingly, when the triplet energy is converted to the singlet energy in the fourth compound, i.e. the delayed fluorescent material in the EML2 364 by RISC mechanism, the singlet energy of the delayed fluorescent material can be transferred to the second compound, i.e. the fluorescent or phosphorescent material in the EML1 362, which is disposed adjacently to the EML2 364, by fluorescence resonance energy transfer (FRET) mechanism, which transfers exciton energies in a form of non-radiation through an electrical filed by a dipole-dipole interaction.

As the final luminescence occurs in the fluorescent or phosphorescent material, efficient energy transfer becomes possible and high color purity can be realized. As the efficiency of the energy transfer from fourth compound, i.e. the delayed fluorescent material in the EML2 364 to the second compound, i.e. the fluorescent or phosphorescent material in the adjacent EML1 362 is improved, the OLED 300 can enhance its luminous efficiency so as to realize hyper-fluorescence. In addition, since the final luminescence in the EML1 362 occurs with the fluorescent or phosphorescent material, which has a narrow FWHM (full width at half maximum) compared the delayed fluorescent material, being shifted the excited state to the ground state, the color purity of the OLED 300 can be improved.

Figure 4:
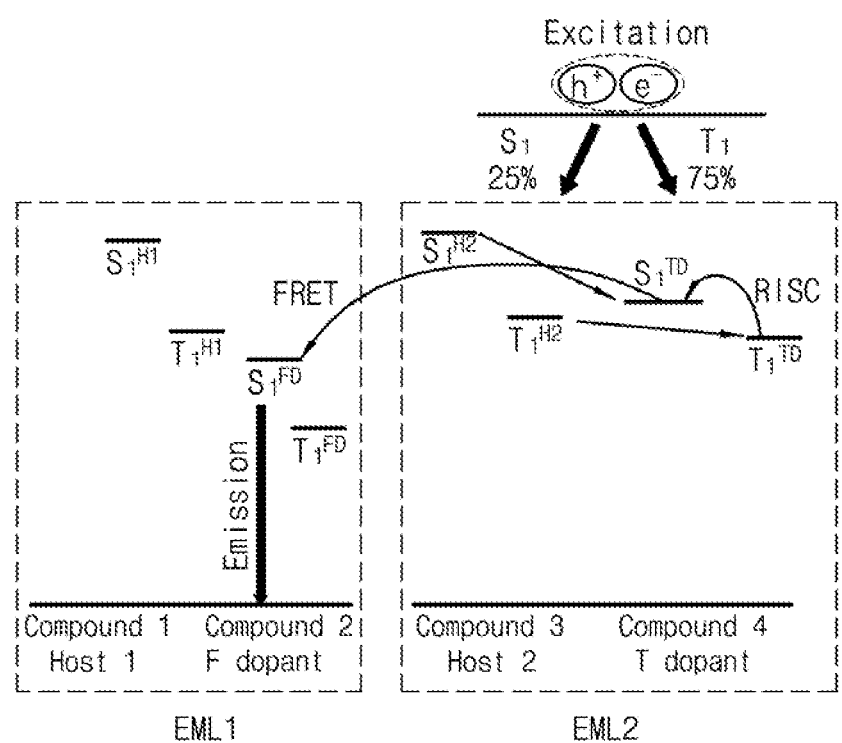
FIG. 4 is a schematic diagram illustrating luminous mechanism by energy level bandgap among luminous materials in the EML in accordance with an exemplary embodiment of the present disclosure.

In order to realize such a hyper-fluorescence, it is necessary to control the singlet energy levels and/or triplet energy levels of the first to fourth compounds within predetermined ranges. FIG. 4 is a schematic diagram illustrating luminous mechanism by energy level bandgap among luminous materials in the EML in accordance with an exemplary embodiment of the present disclosure.

With referring to FIG. 4, it is necessary to transfer exciton energies generated in the first and third compounds, each of which may be the host, to the fourth compound, which may be the delayed fluorescent material, in advance. In order to realize such energy transfers, each of excited state singlet energy levels $S_1^{H}$ and $S_1^{H2}$ and excited state triplet energy levels $T_1^{H1}$ and $T_1^{H2}$ of the first and third compounds, each of which may be the host, should be higher than each of an excited state singlet energy level $S_1^{TD}$ and an excited state triplet energy level $T_1^{TD}$ of the fourth compound, which may be the delayed fluorescent materials, respectively.

For example, when the excited state triplet energy level $T_1^{H1}$ of the first compound and the excited state triplet energy level $T_1^{H2}$ of the third compound are not higher enough than the excited state triplet energy level $T_1^{TD}$) of the fourth compound, the excitons of the triplet state $T_1^{TD}$ of the fourth compound, which may be the delayed fluorescent material, can be reversely transferred to the excited state triplet energy levels $T_1^{H1}$ and $T_1^{H2}$ of the first and third compounds, each of which may be the host. Accordingly, the excitons of the triplet state $T_1^{TD}$ of the fourth compound may be quenched as a non-emission in the first and third compounds, which cannot use the triplet exciton energy, and therefore, the triplet exciton energy generated in the fourth compound cannot be involved in emission process. For example, each of the excited state triplet energy levels $T_1^{H1}$ and $T_1^{H2}$ of the first and third compounds may be high by at least 0.2 eV compared to the excited state triplet energy level $T_1^{TD}$ of the fourth compound.

In one exemplary embodiment, each of the first and third compounds, each of which is respectively the first host and the second host, may have the singlet energy levels SP and SP of, but are not limited to, about 3.0 eV to about 3.5 eV, and the excited state triplet energy level $T_1^{H1}$ and $T_1^{H2}$ of, but are not limited to, about 2.5 eV to about 3.0 eV, respectively. In addition, the fourth compound, which may be the delayed fluorescent material, may have the excited stated singlet energy levels $S_1^{TD}$ of, but are not limited to, about 2.3 eV to about 3.0 V, and the excited state triplet energy level $T_1^{TD}$ of, but are not limited to, about 2.1 eV to about 2.8 eV.

In another exemplary embodiment, the excited state triplet energy level $T_1^{H1}$ of the first compound, which may be the first host, may be higher than the excited state triplet energy level $T_1^{H2}$ of the third compound, which may be the second host. In this case, the exciton energy generated in the third compound may be efficiently transferred to the fourth compound, which may be the delayed fluorescent material, without being transferred to the first compound in which the transferred exciton energy is quenched as a non-emission. In other words, when the excited state triplet energy level $T_1^{H1}$ of the first compound is not higher than the excited state triplet energy level $T_1^{H2}$ of the third compound, the transferred triplet exciton in the first compound, which cannot emit triplet excitons, is quenched as a non-emission and the luminous efficiency can be lowered.

In addition, it may be necessary to transfer energy from the fourth compound, i.e. the delayed fluorescent material, in which excitons of singlet and triplet energy levels are converted to the ICT state by RISC, in the EML2 364 to the second compound, which may be the fluorescent or phosphorescent material, in the EML1 362 so as to realize an OLED having high luminous efficiency and color purity. In order to implement such an OLED, each of the excited state singlet energy level $S_1^{TD}$ and the excited state triplet energy level $T_1^{TD}$ of the fourth compound, which may be delayed fluorescent materials, in the EML2 364 is higher than each of the excited state singlet energy level $S_1^{FD}$ and the excited state triplet energy level $T_1^{FD}$ of the second compound, which is the fluorescent material, in the EML1 362, respectively.

Alternatively, when the second compound in the EML1 362 is a phosphorescent material, the excited state singlet energy level $S_1^{TD}$ of the fourth compound, which may be the delayed fluorescent material, may not be higher than an excited state singlet energy level of the second compound. However, the excited state triplet energy level $T_1^{TD}$ of the fourth compound may be higher than the excited state singlet energy level of the second compound as the phosphorescent material.

As an example, the second compound, which may be the fluorescent material, may have the excited state singlet energy level $S_1^{FD}$ of, but are not limited to, about 2.3 eV to about 2.7 eV and have the excited triplet energy level $T_1^{FD}$ of, but are not limited to, about 2.1 eV to about 2.5 eV. Alternatively, the second compound as the phosphorescent material may have the excited state singlet energy level of, but are not limited to, about 2.3 eV to about 2.8 eV, and have the excited triplet energy level of, but are not limited to, about 2.0 eV to about 2.4 eV.

Moreover, the excited state singlet energy level $S_1^{H1}$ of the first compound is higher than the excited state singlet energy level $S_1^{FD}$ of the second compound as the fluorescent material in order to prevent the exciton energy transferred from the fourth compound to the second compound from being transferred to the first compound and to realize efficient luminescence. In an exemplary embodiment, the excited state triplet energy level $T_1^{H1}$ of the first compound may be higher than the excited state triplet energy level $T_1^{FD}$ of the second compound. The fourth compound must have an energy level bandgap $\Delta E_{ST}^{TD}$ between the excited stated singlet energy level $S_1^{TD}$ and the excited state triplet energy level $T_1^{TD}$ equal to or less than about 0.3 eV in order to realized delayed fluorescence (see, FIG. 3).

When the delayed fluorescent material is used in implementing luminescence, the triplet exciton can participate in the emission process. When a recombination region of forming an exciton is formed at an interface between the EML and the ETL, the possibility of meeting between the triplet exciton of the delayed fluorescent material and the hole-polaron to interact each other is increased. Due to the interaction between the triplet exciton of the delayed fluorescent material and the hole-polaron, the triplet exciton of the delayed fluorescent material fails to contribute to the emission mechanism, resulting in being quenched as a non-emission. As the non-emission quenching is increased, stresses are applied to the luminous materials in the EML 360, which causes damages in the materials, and thereby reducing the life span of the OLED 300.

Figure 5:
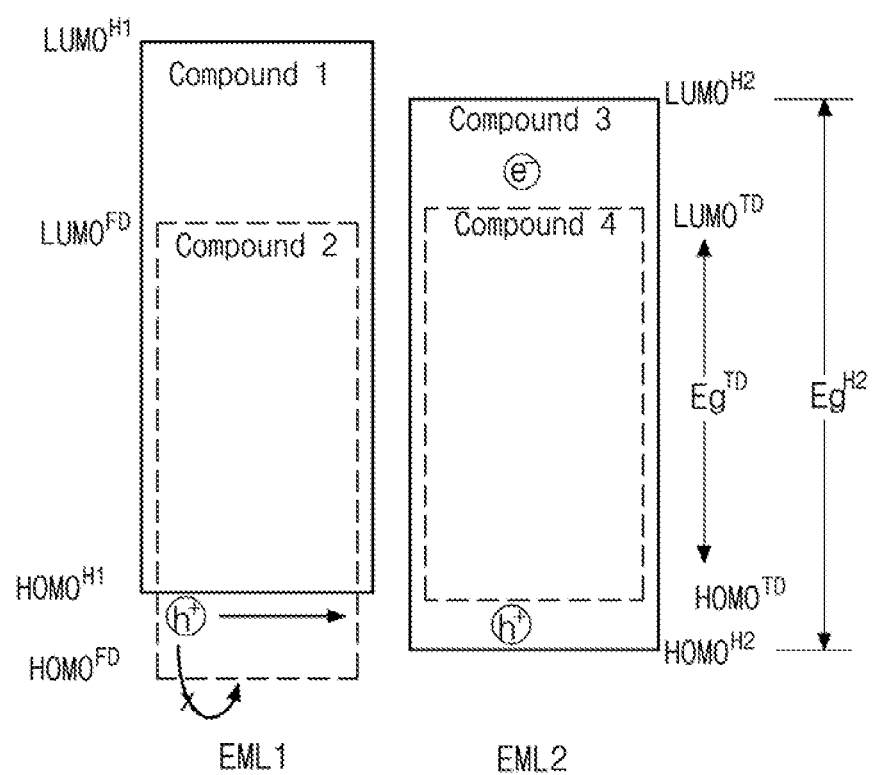
FIG. 5 is a schematic diagram illustrating HOMO energy levels and LUMO energy levels among the luminous materials in the EML in accordance with an exemplary embodiment of the present disclosure.

Accordingly, it may be necessary to adjust properly a Highest Occupied Molecular Orbital (HOMO) energy levels and/or Lowest Unoccupied Molecular Orbital (LUMO) energy levels of the luminous materials, i.e. the first to fourth compounds in the EML1 362 and EML2 364 in order to prevent the non-emission quenching of the exciton energies which may be caused in the EML 360 and to allow the charges to be efficiently injected to the EML 360. FIG. 5 is a schematic diagram illustrating HOMO energy levels and LUMO energy levels among the luminous materials in a double-layered EML in accordance with an exemplary embodiment of the present disclosure.

As illustrated in FIG. 5, a HOMO energy level $HOMO^{H1}$ of the first compound, which may be the first host having a fluorescent property, is higher or shallower than a HOMO energy level $HOMO^{FD}$ of the second compound, which may be the fluorescent or phosphorescent material, in the EML1 362. In contrast, a HOMO energy level $HOMO^{H2}$ of the third compound, which may be the second host having a phosphorescent property, is lower or deeper than a HOMO energy level $HOMO^{TD}$ of the fourth compound, which may be the delayed fluorescent material.

When a dopant has a weight ratio less than 10 wt % in an EML including a host and the dopant, electrons and holes are injected into the host in advance. The exciton energy of the host are transferred to the dopant through Dexter transfer mechanism where an energy transfer is dependent on the wave function superposition between adjacent molecules, and FRET (Fluorescence Resonance Energy Transfer) mechanism where an energy is transferred in a non-radiation mode through an electrical filed by dipole-dipole interaction. However, when the delayed fluorescent material is used as dopant for an EML, the delayed fluorescent material is doped to about 10 wt % or more in the EML in order to maximize the luminous efficiency. In this case, there is a high probability that holes and electrons are directly injected to the dopant without passing through the host.

Accordingly, when both the EML1 362 and the EML2 364 use a host (e.g. a fluorescent host such as the first compound) having higher HOMO energy level than the HOMO energy levels of the fluorescent or phosphorescent material and the delayed fluorescent material, the holes are injected to the HOMO energy level of the host in the EML2 364, and electrons are injected to the LUMO energy level of the delayed fluorescent material in the EML2 364 to form an excited complex, i.e. exciplex between the host and the delayed fluorescent material. Since the triplet energy of the delayed fluorescent material does not contribute the luminous mechanism with quenching as a non-emission, the luminous efficiency of the EML may be lowered. When the non-emission quenching is increased, stress is applied to the luminous materials in the emitting unit 330 (See, FIG. 2), causing damages to the luminous materials, and thereby reducing the life span of the OLED 300.

On the contrary, when both the EML1 362 and the EML 364 use another host (e.g. a phosphorescent host such as the third compound) having lower HOMO energy level than the HOMO energy levels of the fluorescent or phosphorescent material and the delayed fluorescent material, the holes can be trapped by the fluorescent or phosphorescent material having the higher HOMO energy level than the host in the EML1 362.

Holes and electrons cannot be injected into the EML 360 in a balanced manner, i.e. electrons are excessively injected into the EML 360 as compared to the holes, and significant amount of electrons excessively injected into the EML 360 cannot be recombined with holes, and quenched without forming excitons. In addition, as electrons are rapidly injected into the EML 360 compared to holes, holes and electrons cannot recombine in the luminous materials within the EML 360, but recombine at an interface between the EML 360 and the HTL 350. As a result, not only the luminous efficiency of the OLED 300 is lowered but also a high voltage is required in order to realize desired light emission, and thereby, increasing power consumption and reducing the life span of the OLED 300.

Moreover, when the EML1 362, which is disposed adjacently to the first electrode 310, includes the third compound, which may be the second host having relatively low HOMO energy level compared to the first compound, and the fourth compound, which may be the delayed fluorescent material, and the EML2 364 includes the first compound, which may be the first host having relatively high HOMO energy level compared to the third compound and the second compound, which may be the fluorescent or phosphorescent material, an energy level bandgap between an HOMO energy level of the HTL 350 or the EBL 355 and the HOMO energy level of the EML1 362 becomes excessively large. Accordingly, hole injection into the EML1 362 may be delayed.

Moreover, a LUMO energy level bandgap between a LUMO energy level of the ETL 370 or the HBL 375 and the LUMO energy level of the EML2 364 also becomes too large. Accordingly, electron injection into the EML2 364 may also be delayed. As a result, as the injections of holes and electrons into the EML 360 are delayed, the driving voltage of the OLED 300 rises and the luminous efficiency and life span of the OLED 300 may be reduced due to the charge balance reductions.

On the contrary, the EML1 362, which is disposed adjacently to the first electrode 310 (see, FIG. 2), uses the first compound having relatively high HOMO energy level $HOMO^{H1}$ as compared to the HOMO energy level $HOMO^{FD}$ of the second compound which may be the fluorescent or phosphorescent material, as the first host. Since the HOMO energy level $HOMO^{FD}$ of the second compound as the fluorescent or phosphorescent material is lower or deeper than the HOMO energy level $HOMO^{H1}$ of the first compound as the first host, it is possible to prevent or minimize hole trapping by the second compound in the EML1 362 when holes injected from the first electrode 310 (see, FIG. 2) are transported to the EML2 364 via the EML1 362.

Accordingly, holes and electrons can be injected in a balanced manner into the EML2 364 where the first light emission occurs. As a result, it is possible to reduce the amount of quenched charged without forming excitons in the EML2 364. In addition, holes and electrons are recombined within the EML2 364, thereby improving the luminous efficiency and lowering the driving voltage, and thereby reducing power consumption of the OLED 360.

Moreover, the EML2 364, which is disposed adjacently to the second electrode 320 (See, FIG. 2), uses the third compound having relatively low HOMO energy level $HOMO^{H2}$ as compared to the HOMO energy level $HOMO^{TD}$ of the fourth compound which may be the delayed fluorescent material, as the second host. It is possible to inhibit or minimize exciplex formation between the second compound, which may be the second host and the fourth compound, which may be the delayed fluorescent material, in the EML2 364 by controlling the HOMO energy levels between the third and fourth compounds.

In still another exemplary embodiment, LUMO energy levels of the third and fourth compounds can be adjusted so that electrons cannot be directly transferred to the fourth compound, which may be the delayed fluorescent material, in the EML2 364. As an example, a LUMO energy level $LUMO^{H2}$ of the third compound is higher or shallower than a LUMO energy level $LUMO^{TD}$ of the fourth compound. As such, when a HOMO-LUMO energy level bandgap $Eg^{TD}$ of the fourth compound, which may be the delayed fluorescent material, is set within a HOMO-LUMO energy level bandgap $Eg^{H2}$ of the third compound, which may be the second host, an exciplex between the third compound, which may be the second host and the fourth compound, which may be delayed fluorescent material, is not formed in the EML2 364 regardless of the dopant concentrations. Therefore, the triplet energy of the delayed fluorescent material is not quenched as a non-emission, and thereby improving luminous efficiency and life span of the OLED 300.

Further, the HOMO energy level $HOMO^{H1}$ of the first compound, which may be the first host, in the EML1 362 is higher than the HOMO energy level $HOMO^{H2}$ of the third compound, which may be the second host, in the EML2 364. As a result, holes can be efficiently transferred from the first compound to the third compound.

Moreover, the LUMO energy level $LUMO^{H1}$ of the first compound, which may be the first host, in the EML1 362 is higher than the LUMO energy level $LUMO^{H2}$ of the third compound, which may be the second host, in the EML2 364. Accordingly, electrons injected into the EML2 364 from the ETL 370 (see, FIG. 2) do not transport to the EML1 362, but can be recombined with holes injected into the EML2 364 from the EML1 362 to form excitons, so that the OLED 300 can maximize its the luminous efficiency.

In one exemplary embodiment, an energy level bandgap ($|HOMO^{H2}-HOMO^{TD}|$) between the HOMO energy level $HOMO^{H2}$ of the third compound and the HOMO energy level $HOMO^{TD}$ of the fourth compound, or an energy level bandgap ($|LUMO^{H2}-LUMO^{TD}|$) between the LUMO energy level $LUMO^{H2}$ of the third compound and the LUMO energy level $LUMO^{TD}$ of the fourth compound may be equal to or less than about 0.5 eV, for example, between about 0.1 eV to about 0.5 eV.

In one exemplary embodiment, the first compound, which may be the first host, may have the HOMO energy level $HOMO^{H1}$ of, but are not limited to, about −5.5 eV to about −6.0 eV, preferably about −5.5 eV to about −5.8 eV and have the LUMO energy level $LUMO^{H1}$ of, but are not limited to, about −2.0 eV to about −2.5 eV, preferably about −2.0 eV to about −2.4 eV. The second compound, which may be the fluorescent material, may have the HOMO energy level $HOMO^{FD}$ of, but are not limited to, about −5.5 eV to about −6.2 eV, preferably about −5.7 eV to about −6.1 eV and have a LUMO energy level $LUMO^{FD}$ of, but are not limited to, about −2.6 eV to about −3.4 eV. Also, the second compound, which may be the phosphorescent material, may have a HOMO energy level of, but are not limited to, about −5.6 eV to about −6.0 eV and have a LUMO energy level of, but are not limited to, about −3.0 eV to about −3.3 eV.

Moreover, the third compound, which may be the second host, may have the HOMO energy level $HOMO^{H2}$ of, but are not limited to, about −5.8 eV to about −6.2 eV and have the LUMO energy level $LUMO^{H2}$ of, but are not limited to, about −2.3 eV to about −2.8 eV. The fourth compound, which may be the delayed fluorescent materials, may have the HOMO energy level $HOMO^{FD}$ of, but are not limited to, −5.7 eV to about −6.0 eV and have the LUMO energy level $LUMO^{TD}$ of, but are not limited to, about −2.8 eV to about −3.5 eV, respectively.

It is possible to improve luminous efficiency and life span, lower driving voltage to reduce power consumption and enhance color purity of the OLED 300 where the EML1 362 and EML2 364 include the first to fourth compound as the luminous materials whose energy levels such as singlet energy levels, triplet energy levels, HOMO energy levels and/or LUMO energy levels are controlled within the predetermined ranges.

As described above, the first compound, which may be the first host having the fluorescent property, may be materials having relative high excited sated singlet and triplet energies $S_1^{H1}$ and $T_1^{H1}$ as well as relatively shallow HOMO energy level $HOMO^{H1}$ as compared to the excited state singlet and triplet energy levels $S_1^{FD}$ and $T_1^{FD}$ and the HOMO energy level $HOMO^{FD}$ of the second compound, which may be the fluorescent or phosphorescent material, in the EML1 362, so as to prevent hole traps by the second compound in the EML1 362. As an example, the first compound may include, but are not limited to, an organic compound having the following structure of Chemical Formula 1:

Chemical Formula 1

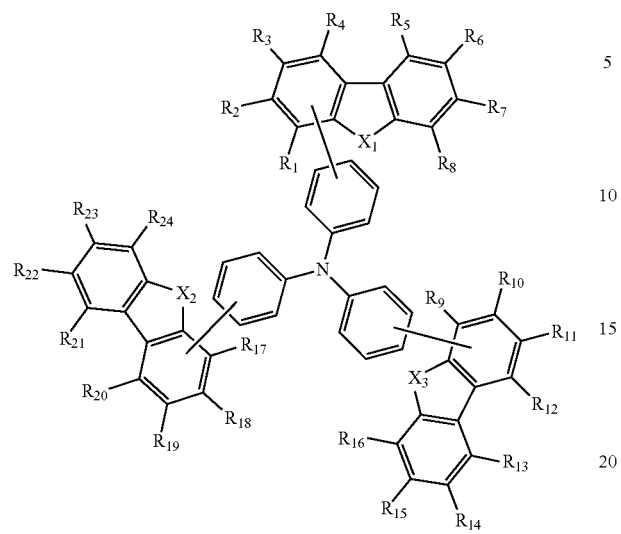

Chemical Formula 2

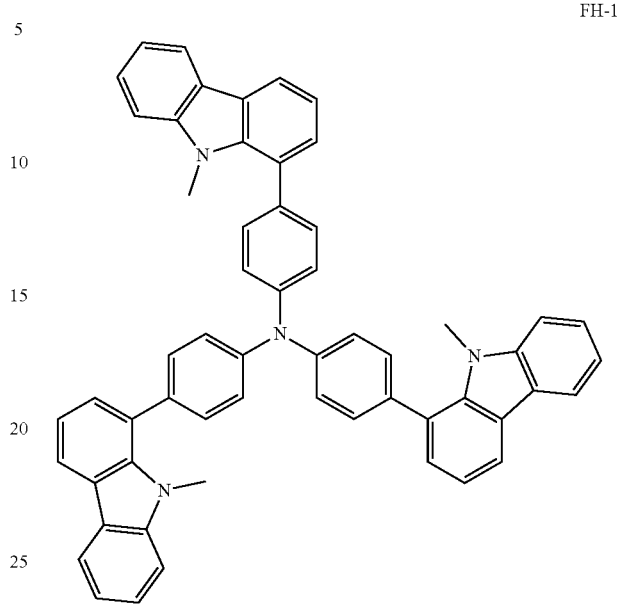

In Chemical Formula 1, each of $R_1$ to $R_{24}$ is independently hydrogen, deuterium, tritium, silyl group, $C_1$~$C_{20}$ alkyl group, $C_1$~$C_{20}$ alkoxy group, $C_1$~$C_{20}$ alkyl amino group, $C_5$~$C_{30}$ aryl group, $C_4$~$C_{30}$ hetero aryl group, $C_5$~$C_{30}$ alkyl aryl group, $C_4$~$C_{30}$ hetero alkyl aryl group, $C_5$~$C_{30}$ aryloxyl group, $C_4$~$C_{30}$ hetero aryloxyl group, $C_5$~$C_{30}$ aryl amino group or $C_4$~$C_{30}$ hetero aryl amino group, respectively. Each of $X_1$, $X_2$ and $X_3$ is independently $CR_{25}R_{26}$, $NR_{27}$, oxygen (O) or sulfur (S), respectively, wherein each of $R_{25}$, $R_{26}$ and $R_{27}$ is independently hydrogen, deuterium, tritium, $C_1$~$C_{20}$ alkyl group or $C_1$~$C_{20}$ alkoxy group.

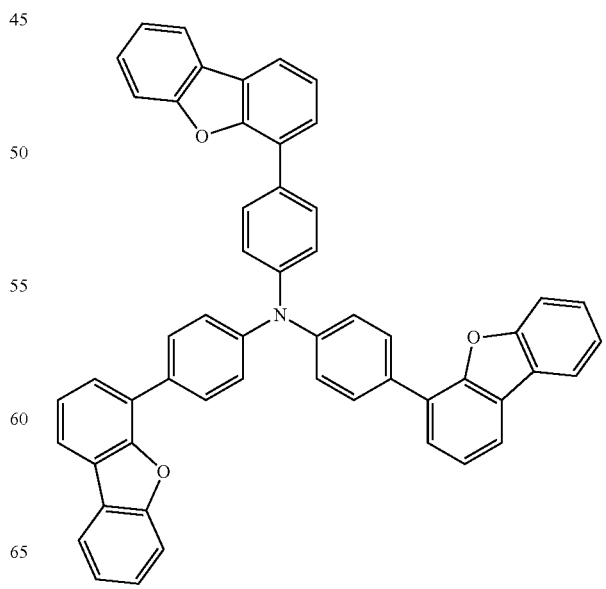

Since the organic compound having the structure of Chemical Formula 1 has a high HOMO energy level and a LUMO energy level, the organic compound may be used as the host in the EML1 362. Particularly, the first compound, which may be the first host, may include anyone of the following structure of Chemical Formula 2.

FH-3
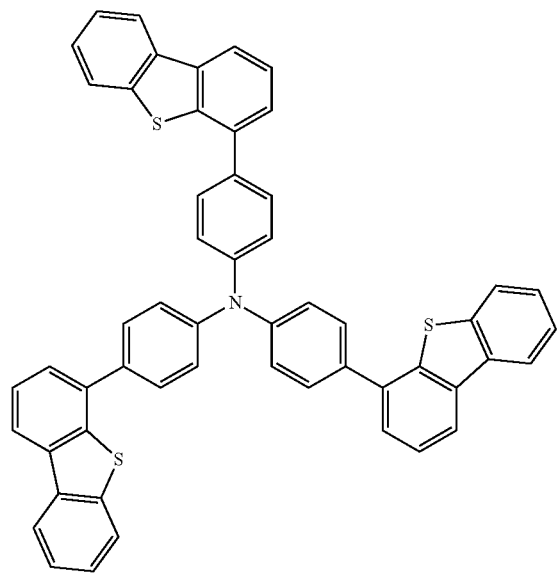
FH-4
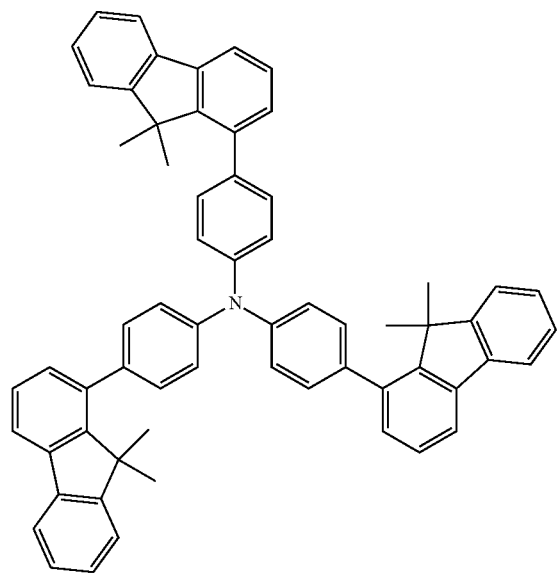
FH-5
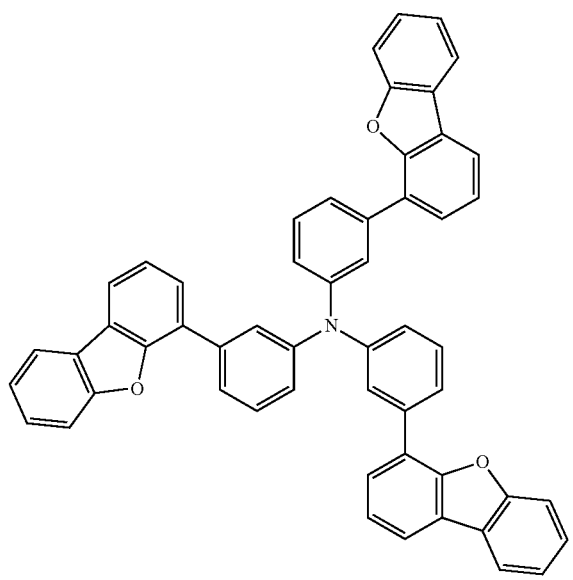
FH-6
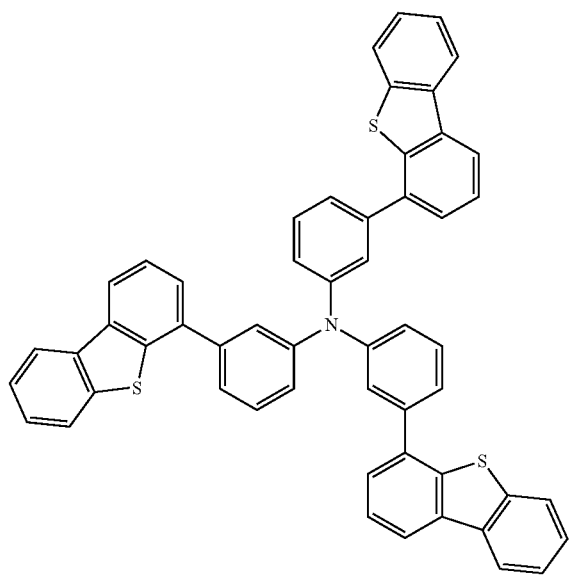

FH-7
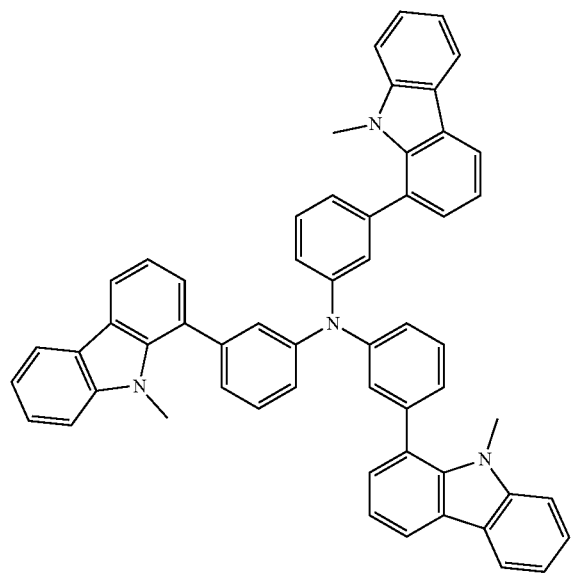
FH-8
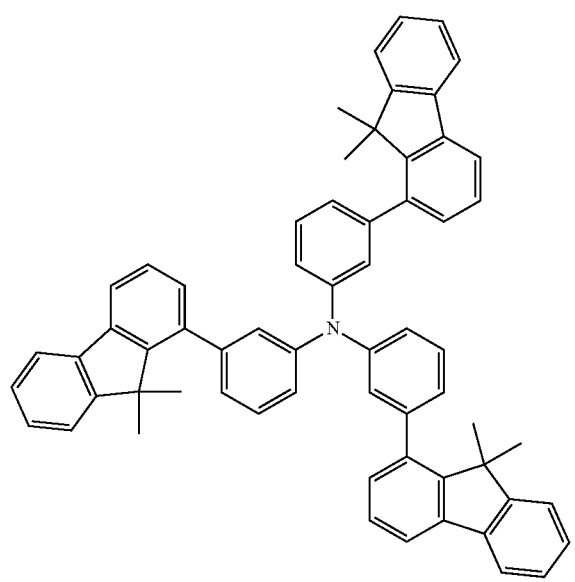
FH-9
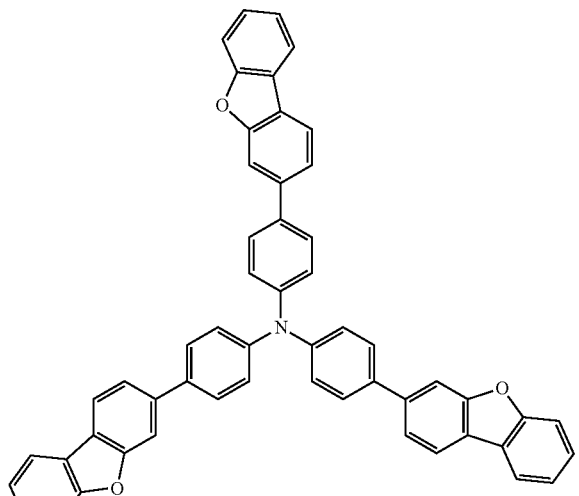
FH-10
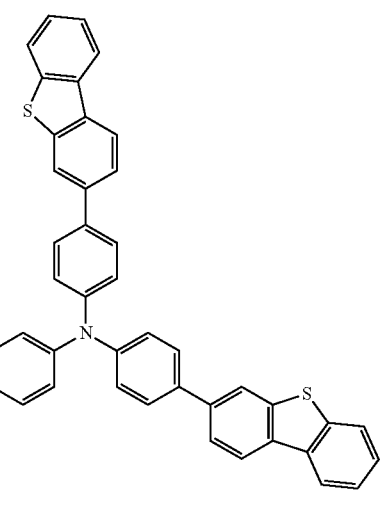
FH-11
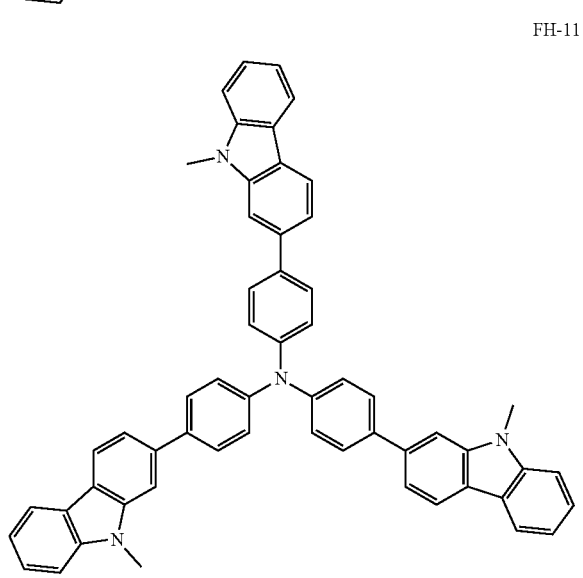

FH-12
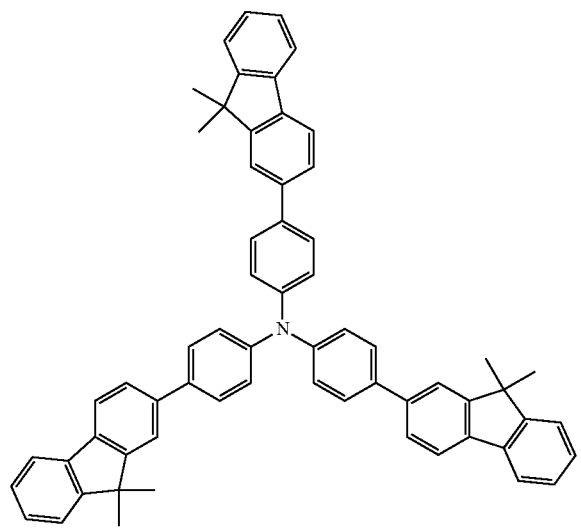
FH-13
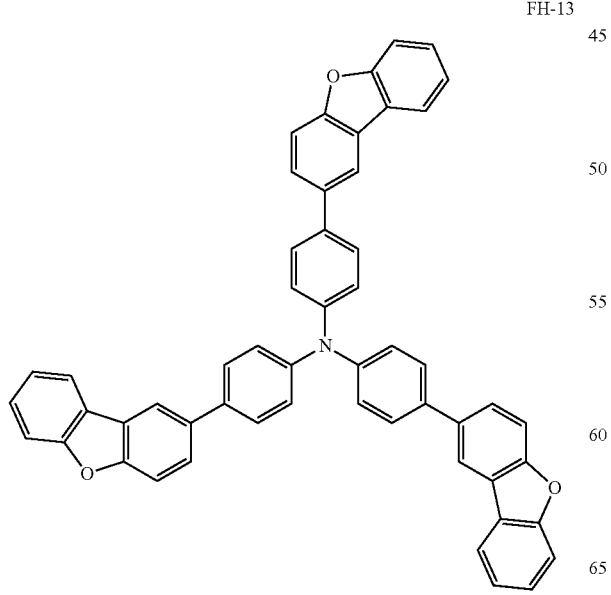
FH-14
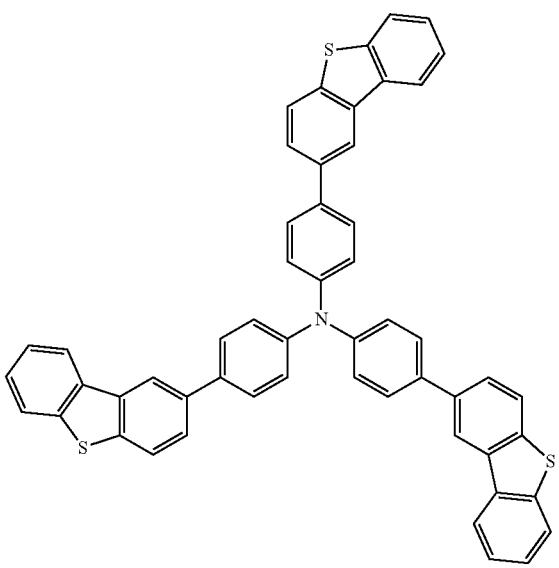
FH-15

FH-16

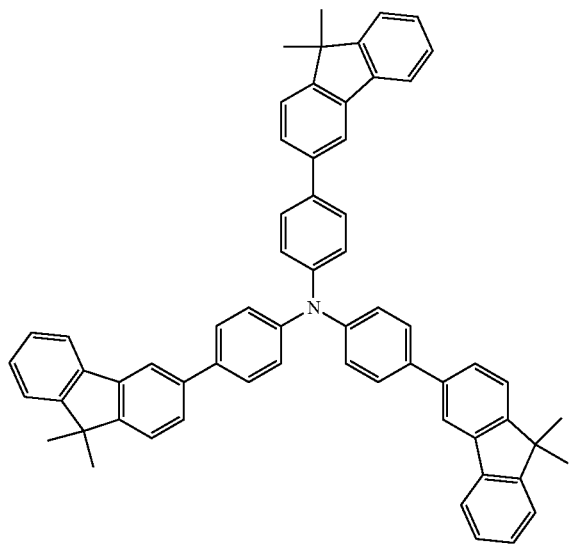

FH-17

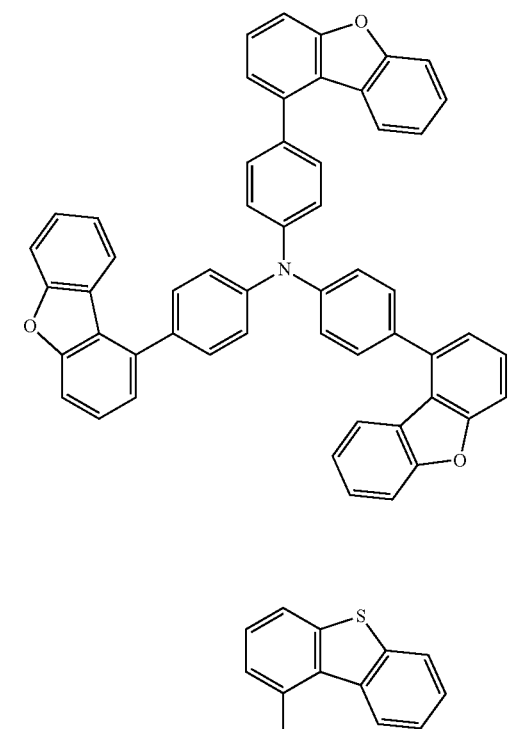

FH-18

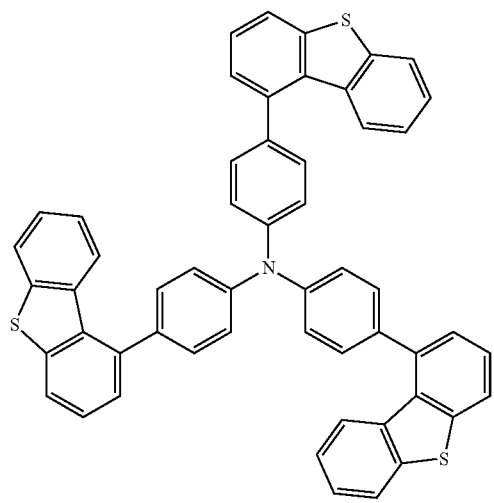

FH-19

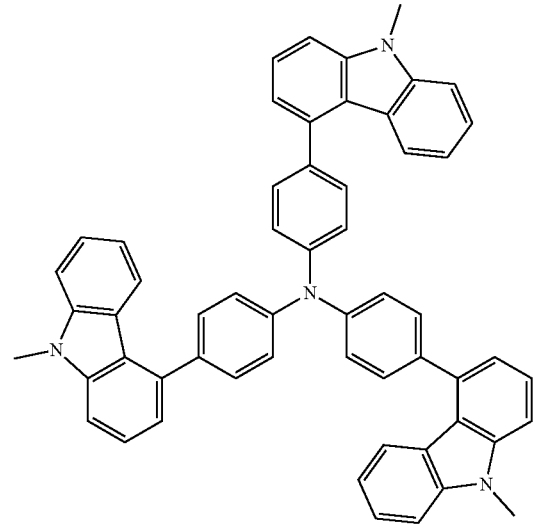

FH-20

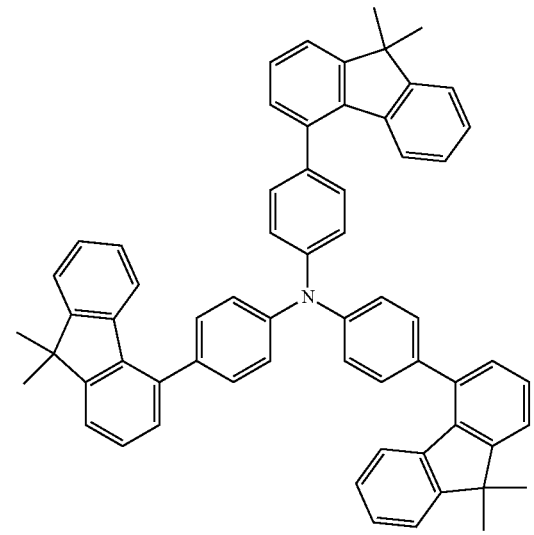

The third compound, which may be used as the second host in the EML2 364, may have relatively high singlet and triplet energy levels $S_1^{H2}$ and $T_1^{H2}$ compared to the singlet and triplet energy levels $S_1^{TD}$ and $T_1^{TD}$ of the fourth compound, which may be the delayed fluorescent material in the EML2 364, relatively lower HOMO energy level $HOMO^{H2}$ compared to the HOMO energy level $HOMO^{TD}$ of the fourth compound, and optionally higher LUMO energy level $LUMO^{H2}$ compared to the LUMO energy level $LUMO^{TD}$ of the fourth compound. As such, an exciplex between the third and fourth compound cannot be formed in the EML2 364. In one exemplary embodiment, the third compound may include, but are not limited to, an organic compound having the following structure of Chemical Formula 3:

Chemical Formula 3

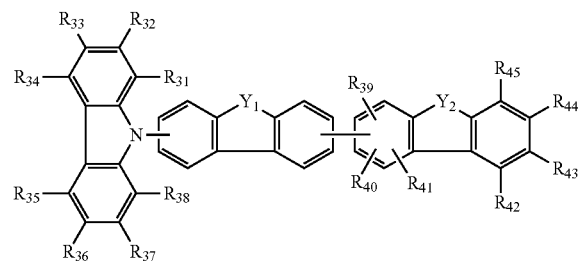

In Chemical Formula 3, each of $R_{31}$ to $R_{45}$ is independently hydrogen, deuterium, tritium, silyl group, $C_1$~$C_{10}$ alkyl group, $C_1$~$C_{10}$ alkoxy group, $C_1$~$C_{10}$ alkyl amino group, $C_5$~$C_{30}$ aryl group, $C_4$~$C_{30}$ hetero aryl group, $C_5$~$C_{30}$ alkyl aryl group, $C_4$~$C_{30}$ hetero alkyl aryl group, $C_5$~$C_{30}$ aryloxyl group, $C_4$~$C_{30}$ hetero aryloxyl group, $C_5$~$C_{30}$ aryl amino group or $C_4$~$C_{30}$ hetero aryl amino group, or two adjacent groups among $R_{31}$ to $R_{45}$ forms a fused aryl ring or a fused hetero aryl ring each of which is unsubstituted or substituted with $C_5$~$C_{30}$ aryl group or $C_4$~$C_{30}$ hetero aryl group. Each of $Y_1$ and $Y_2$ is independently $NR_{46}$, oxygen (O) or sulfur (S), wherein $R_{46}$ is hydrogen, deuterium, tritium, $C_1$~$C_{20}$ alkyl group or $C_1$~$C_{20}$ alkoxy group.

As indicated in Chemical Formula 3, the third compound includes a carbazolyl moiety (having $R_{31}$ to $R_{38}$ groups), and at least two dibenzofuranyl and/or dibenzothiophenyl moieties (each having $Y_1$ and $Y_2$ group). Hereinafter, the central dibenzofuranyl/dibenzothiophenyl moiety linked to the carbazolyl moiety will be refereed as "a first dibenzofuranyl/dibenzothiophenyl moiety" and the side dibenzofuranyl/dibenzothiophenyl moiety linked to the first dibenzofuranyl/dibenzothiophenyl moiety will be referred as "a second dibenzofuranyl/dibenzothiophenyl moiety".

Since the carbazolyl moiety has a p-type property because of its excellent bonding ability with holes, and the first and second dibenzofuranyl/dibenzothiophenyl moieties have an n-type property because of their relatively better bonding abilities with electrons. Therefore, the organic compound having the structure of Chemical Formula 3 may have bi-polar properties.

In one exemplary embodiment, each of $R_1$ to $R_{27}$ in Chemical Formula 1 and $R_{31}$ to $R_{45}$ in Chemical Formula 3 may be independently hydrogen, deuterium or tritium, respectively. In another exemplary embodiment, each of $R_1$ to $R_{27}$ in Chemical Formula 1 and $R_{31}$ to $R_{45}$ in Chemical Formula 3 may be independently linear or branched $C_1$~$C_{20}$ alkyl group, preferably $C_1$~$C_{10}$ alkyl group or $C_1$~$C_{20}$ alkoxy group, preferably $C_1$~$C_{10}$ alkoxy group.

In still another exemplary embodiment, each of $R_1$ to $R_{27}$ in Chemical Formula 1 and $R_{31}$ to $R_{45}$ in Chemical Formula 3 may be independently aromatic or hetero aromatic group. As an example, when each of $R_1$ to $R_{27}$ in Chemical Formula 1 and $R_{31}$ to $R_{45}$ in Chemical Formula 3 is $C_5$~$C_{30}$ aryl group, each of $R_1$ to $R_{27}$ in Chemical Formula 1 and $R_{31}$ to $R_{45}$ in Chemical Formula 3 may independently be, but are not limited to, unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyreneyl, fluoranthenyl, triphenylenyl, chrysenyl, tetraphenyl, tetracenyl, pleiadenyl, picenyl, pentaphenyl, pentacenyl, fluorenyl, indeno-fluorenyl or spiro-fluorenyl.

In an alternative embodiment, when each of $R_1$ to $R_{27}$ in Chemical Formula 1 and $R_{31}$ to $R_{45}$ in Chemical Formula 3 is $C_4$~$C_{30}$ hetero aryl group, each of $R_1$ to $R_{27}$ in Chemical Formula 1 and $R_{31}$ to $R_{45}$ in Chemical Formula 3 may independently be, but are not limited to, unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, bezno-carbazolyl, dibenzo-carbazolyl, indolo-carbazolyl, indeno-carbazolyl, benzofuro-carbazolyl, benzothieno-carbazolyl, quinolinyl, iso-quinolinyl, phtalazinyl, quinoxalinyl, cinnolinyl, quinazolinyl, quinozolinyl, quinolizinyl, benzo-quinazolinyl, benzo-quinoxalinyl, acridinyl, phenanthrolinyl, perimidinyl, phenanthridinyl, pteridinyl, cinnolinyl, naphththyridinyl, furanyl, pyranyl, oxazinyl, oxazolyl, oxadiazolyl, triazolyl, dioxinyl, benzofurnaly, dibenzo-furanyl, thiopyranyl, xanthenyl, chromenyl, iso-chromenyl, thioazinyl, thiophenyl, benzo-thiophenyl, dibenzo-thiophenyl, difuro-pyrazinyl, benzofuro-dibenzo-furanyl, benzothieno-benzo-thiophenyl, benzothieno-dibenzo-furanyl, benzothieno-benzo-furanyl, benzothieno-dibenzo-furanyl or N-substituted spiro-fluorenyl.

In one exemplary embodiment, when each of $R_1$ to $R_{27}$ in Chemical Formula 1 and $R_{31}$ to $R_{45}$ in Chemical Formula 3 is aryl or hetero aryl group, the aryl or hetero aryl group may consist of 1 to 3 aromatic rings. When the number of the aromatic or hetero aromatic rings constituting each of each of $R_1$ to $R_{27}$ in Chemical Formula 1 and $R_{31}$ to $R_{45}$ in Chemical Formula 3 is increased, the conjugated structure in the entire organic compound becomes excessively long, so that the bandgap of the organic compound may be excessively reduced. As an example, when each of $R_1$ to $R_{27}$ in Chemical Formula 1 and $R_{31}$ to $R_{45}$ in Chemical Formula 3 is aromatic or hetero aromatic group, each of $R_1$ to $R_{27}$ in Chemical Formula 1 and $R_{31}$ to $R_{45}$ in Chemical Formula 3 may independently be, but are not limited to, phenyl, biphenyl, pyrrolyl, triazinyl, imidazolyl, pyrazolyl, pyridinyl, pyrazinyl, pyrimidinyl, pyridazinyl, furanyl, benzo-furanyl, dibenzo-furanyl, thiophenyl, benzo-thiophenyl, dibenzo-thiophenyl or carbazolyl.

In another exemplary embodiment, adjacent two groups among $R_{31}$ to $R_{45}$ in Chemical Formula 3 may form fused aromatic or hetero aromatic ring unsubstituted or substituted with at least one of $C_5$~$C_{30}$ aryl group and $C_4$~$C_{30}$ hetero aryl group. When adjacent two groups among $R_{31}$ to $R_{45}$ forms the fused aromatic or hetero aromatic ring, the $C_5$~$C_{30}$ aryl group and $C_4$~$C_{30}$ hetero aryl group, each of which may be substituted to the aromatic or hetero aromatic ring, may consist of 1 or 2 aromatic or hetero aromatic rings. In this case, the organic compound having the structure of Chemical Formula 3 may have an energy level bandgap suitable for use in the EML 360. As an example, when adjacent two groups among $R_{31}$ to $R_{45}$ form fused aromatic or hetero aromatic ring, the aromatic or hetero aromatic group, which may be substituted to the aromatic or hetero aromatic ring, may be, but are not limited to, phenyl, biphenyl, pyrrolyl, imidazolyl, pyrazolyl, pyridinyl, pyrazinyl, pyrimidinyl, pyridazinyl, furanyl or thiophenyl, preferably phenyl.

As an example, adjacent two groups among $R_{31}$ to $R_{38}$ constituting the carbazolyl moiety forms fused ring, the carbazolyl moiety may form, but are not limited to, a benzo-carbazolyl moiety, a dibenzo-carbazolyl moiety, a benzofuro-carbazolyl moiety, a benzothieno-carbazolyl moiety, an indeno-carbazolyl moiety, an indolo-carbazolyl moiety and the likes, each of which is unsubstituted or substituted with linear or branched $C_1$~$C_{20}$ alkyl group, preferably linear or branched $C_1$~$C_{10}$ alkyl group, $C_5$~$C_{30}$ aryl group, preferably $C_5$~$C_{20}$ aryl group (e.g. phenyl and/or naphthyl), $C_4$~$C_{30}$ hetero aryl group, preferably $C_4$~$C_{20}$ hetero aryl group (e.g. pyridyl, pyrimidyl and/or carbazolyl) and combination thereof, respectively.

In another embodiment, adjacent two groups among $R_{39}$ to $R_{45}$ constituting the second dibenzofuranyl/dibenzothiophenyl moiety forms fused ring, the second dibenzofuranyl/dibenzothiophenyl moiety may form, but are not limited to, a pyrido-dibenzofuranyl moiety, a pyrido-dibenzothiophenyl moiety, an indeno-dibenzofuranyl moiety, an indeno-dibenzothiophenyl moiety, an indolo-dibenzofuranyl moiety, an indolo-dibenzothiophenyl moiety and the likes, each of which is unsubstituted or substituted with linear or branched $C_1$~$C_{20}$ alkyl group, preferably linear or branched $C_1$~$C_{10}$ alkyl group, $C_5$~$C_{30}$ aryl group, preferably $C_5$~$C_{20}$ aryl group (e.g. phenyl and/or naphthyl), $C_4$~$C_{30}$ hetero aryl group, preferably $C_4$~$C_{20}$ hetero aryl group (e.g. pyridyl, pyrimidyl and/or carbazolyl) and combination thereof, respectively.

Since the third compound having the structured of Chemical Formula 3 includes the carbazolyl moiety having p-type property as well as dibenzofuranyl/dibenzothiophenyl moieties having n-type property, the first compound has excellent affinity to the holes and electrons. Accordingly, when the second compound having the structure of Chemical 3 is applied to the EML 360 of the OLED 300, a recombination zone where holes and electrons form an exciton is formed in the middle of the EML 360, not in the interface between the EML 360 and the ETL 370.

In addition, the second compound having the structure of Chemical Formula 1 includes the carbazolyl moiety and dibenzofuranyl/dibenzothiophenyl moieties, each of which has a central 5-membered ring connected to both sides of 6-membered rings. Since the carbazolyl moiety as well as the dibenzofuranyl/dibenzothiophenyl has a rigid conformational structure, the first compound having the structure of Chemical Formula 3 may be excellent in heat resistance property. Accordingly, the third compound having the structure of Chemical 3 is not deteriorated by Joule's heat generated in driving the OLED 300. Therefore, the third compound having the structure of Chemical Formula 3 can be applied to the OLED 300, and thereby realizing excellent luminous efficiency and improving luminous life span of the OLED 300.

Moreover, the third compound having the structure of Chemical Formula 3 multiple dibenzofuranyl/dibenzothiophenyl moieties, each of which has a central 5-membered ring connected to both sides of 6-membered rings. Accordingly, the third compound having the structured of Chemical Formula 3 may have a HOMO energy level and a LUMO energy level suitable for use as luminous material, for example, as the host in the EML2 364. In particular, when the third compound is used together with a delayed fluorescent material in the EML2 364, the driving voltage of the OLED 360 may be lowered to reduce the power consumption. Accordingly, the stress applied to the OLED 300 owing to the increase in driving voltage is reduced, thereby improving luminous efficiency and the luminous life span of the OLED 300.

In one exemplary embodiment, the third compound of the present disclosure may include, but are not limited to, an organic compound having the following structure of Chemical Formula 4 or Chemical Formula 5:

Chemical Formula 4

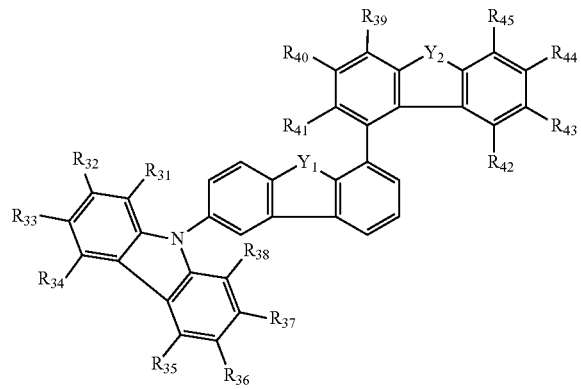

Chemical Formula 4

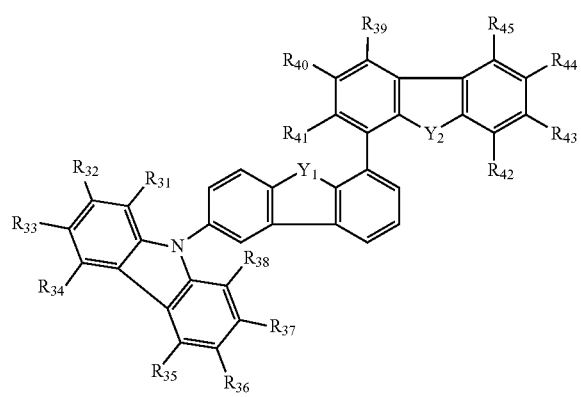

In Chemical Formula 4 and Chemical Formula 5, each of $R_{31}$ to $R_{45}$, $Y_1$ and $Y_2$ is identical as defined in Chemical Formula 3, respectively.

Particularly, the third compound may include, but are not limited to, anyone of the following structure of Chemical Formula 6.

Chemical Formula 6

TH-1

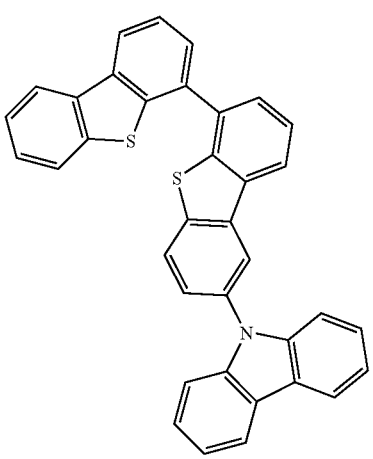

TH-2
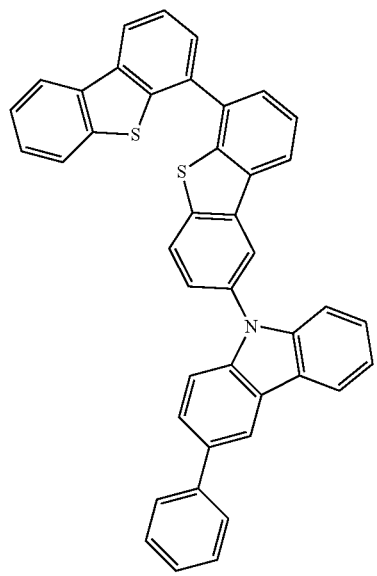
TH-3
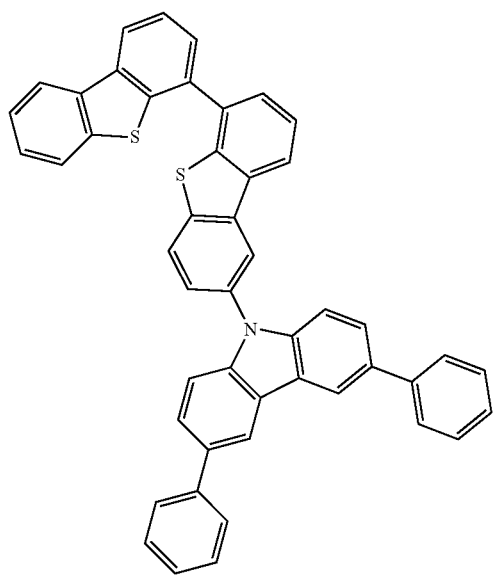
TH-4
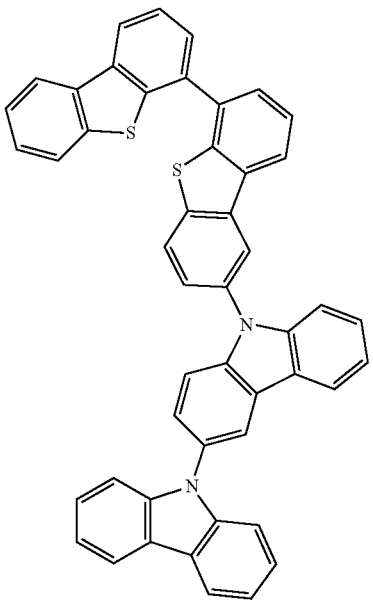
TH-5
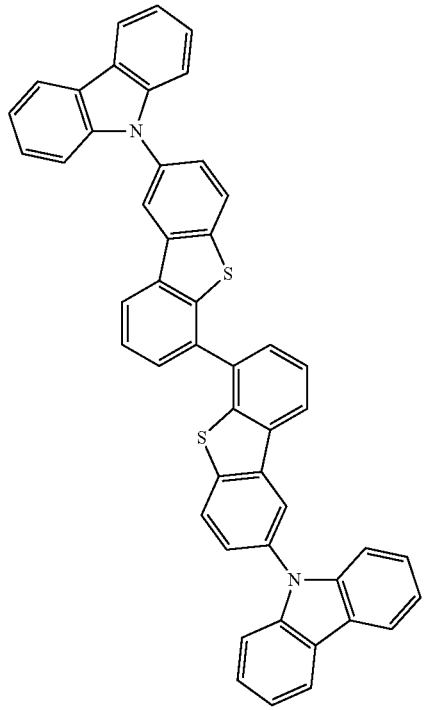

TH-6
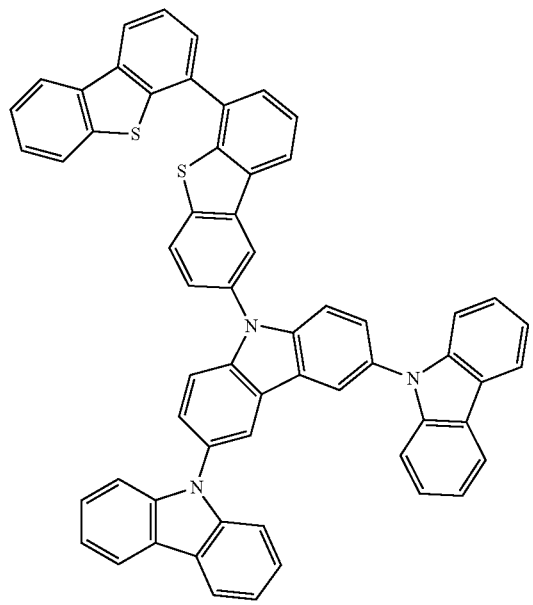
TH-7
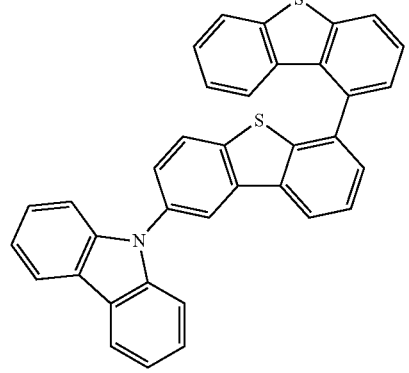
TH-8
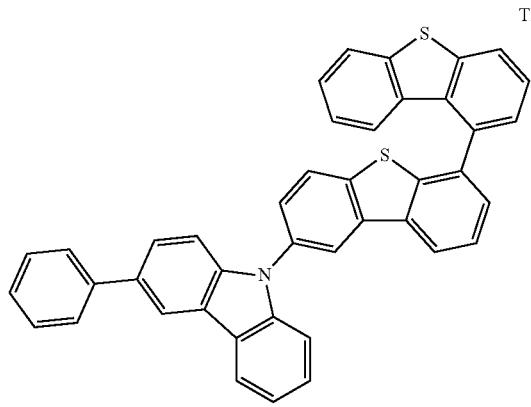
TH-9
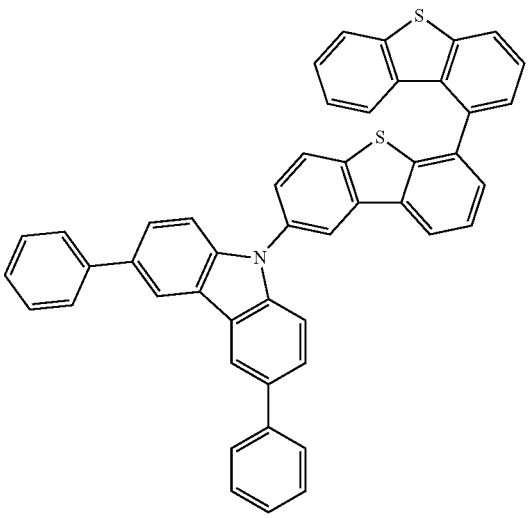
TH-10
TH-11
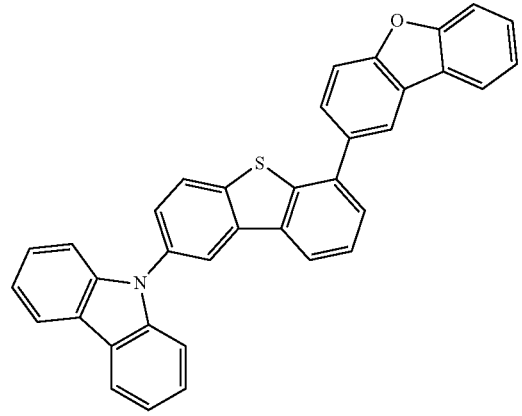

TH-12
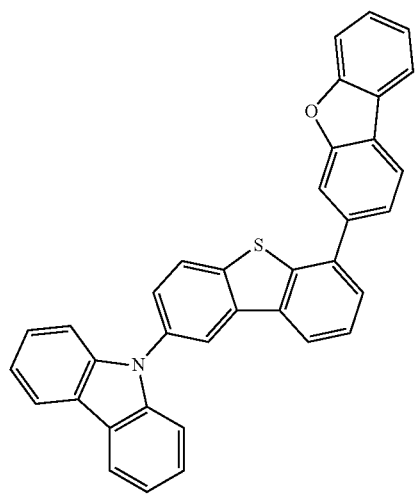
TH-13
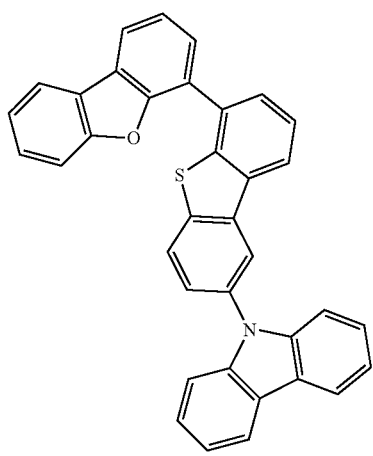
TH-14
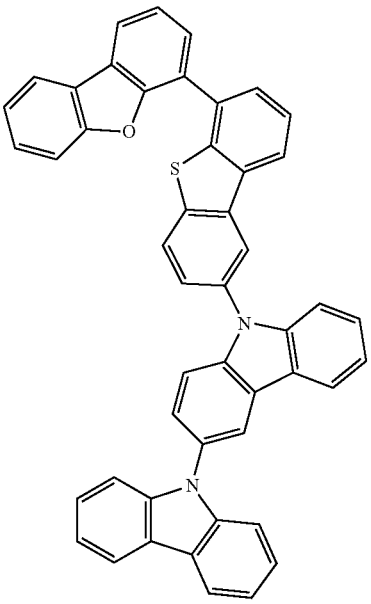
TH-15
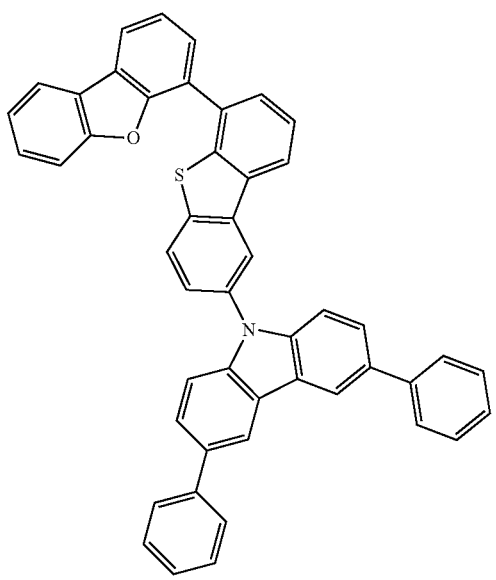
TH-16

TH-17
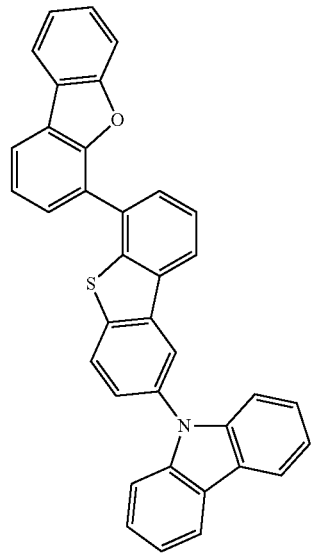
TH-18
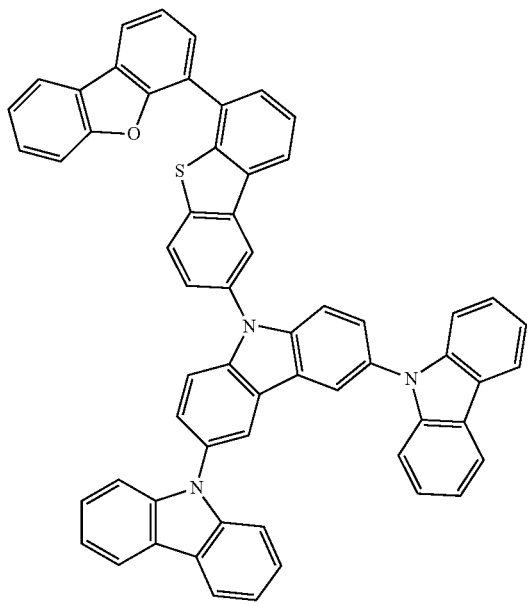
TH-19
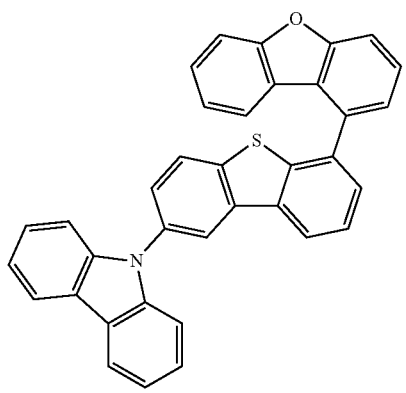
TH-20
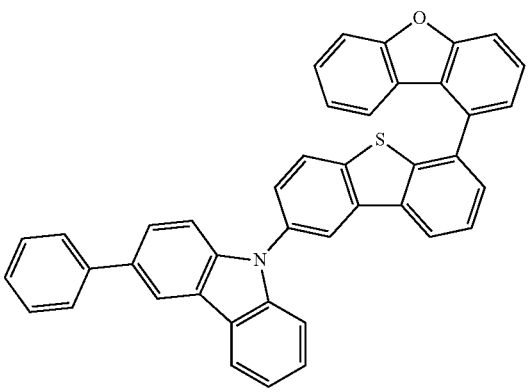
TH-21
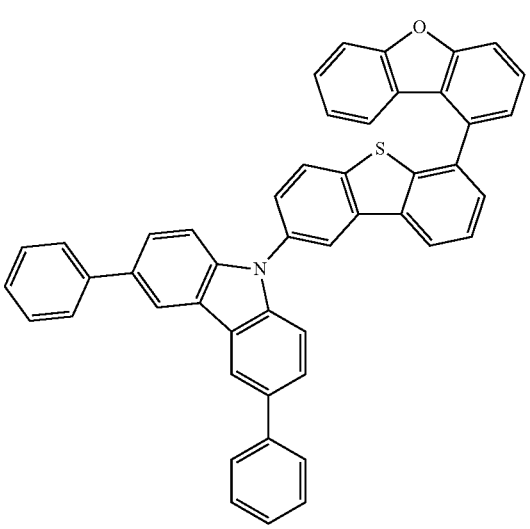
TH-22
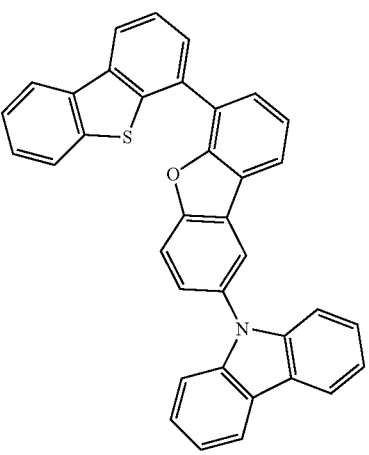

TH-23
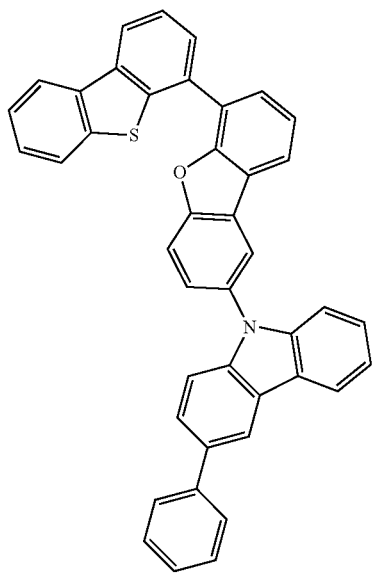
TH-25
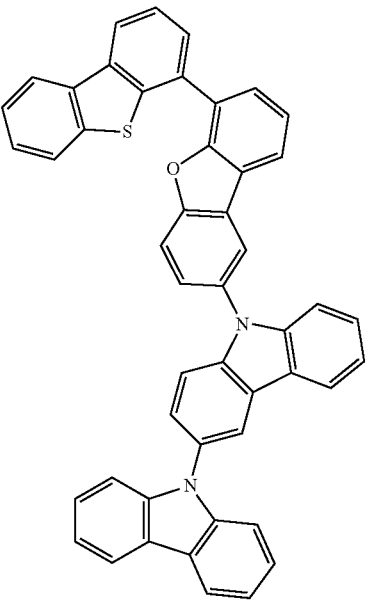
TH-24
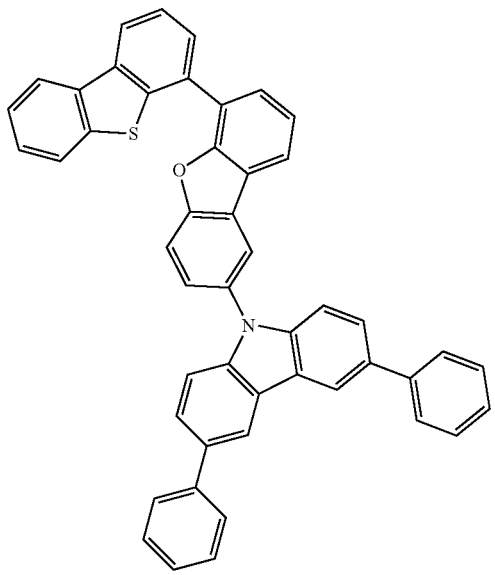
TH-26
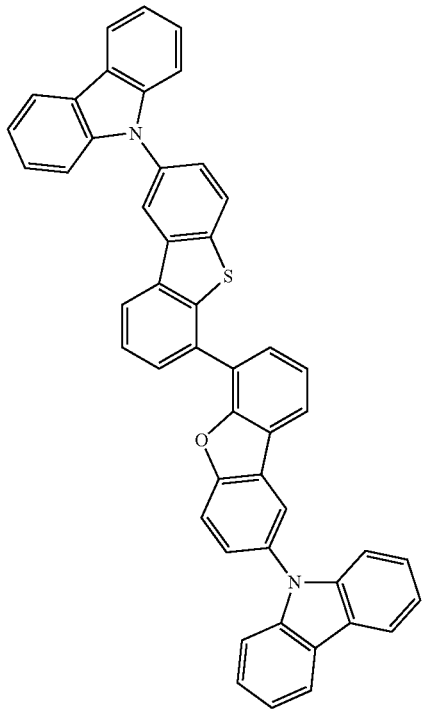

TH-27
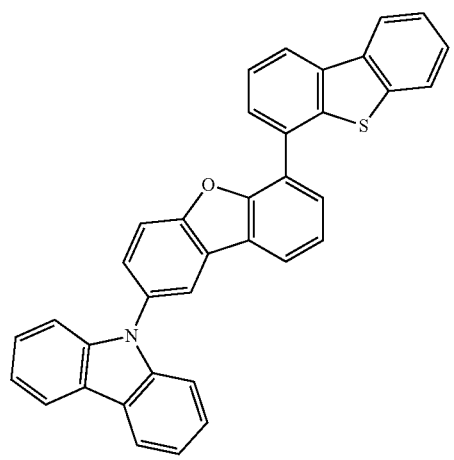
TH-28
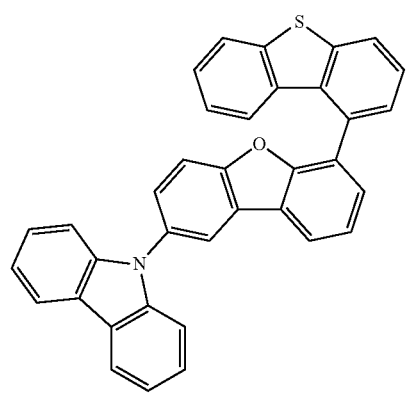
TH-29
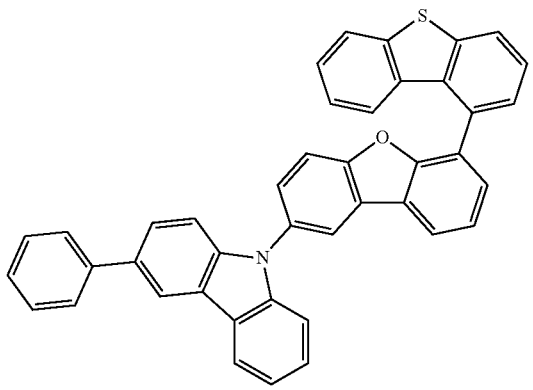
TH-30
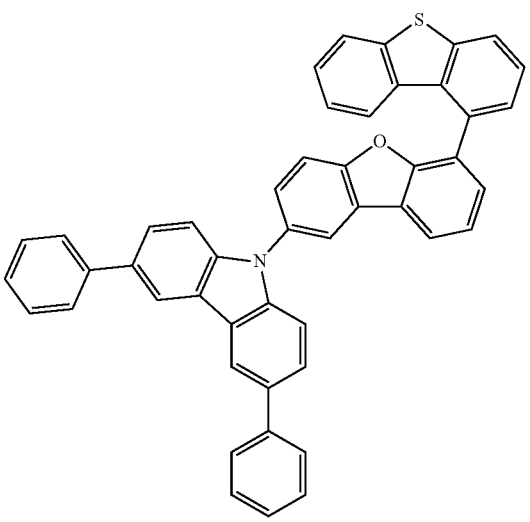
TH-31
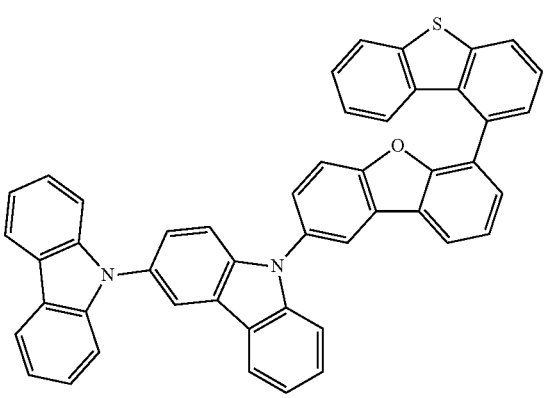
TH-32
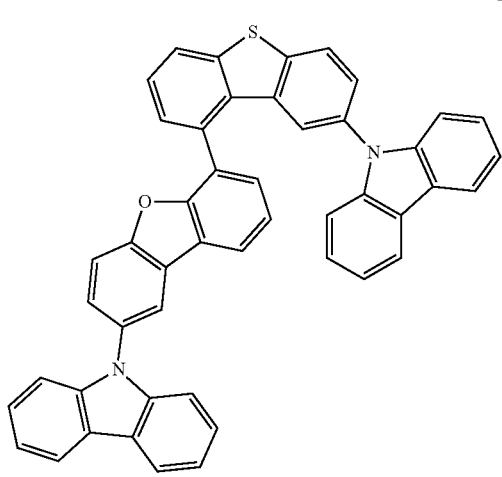

TH-33
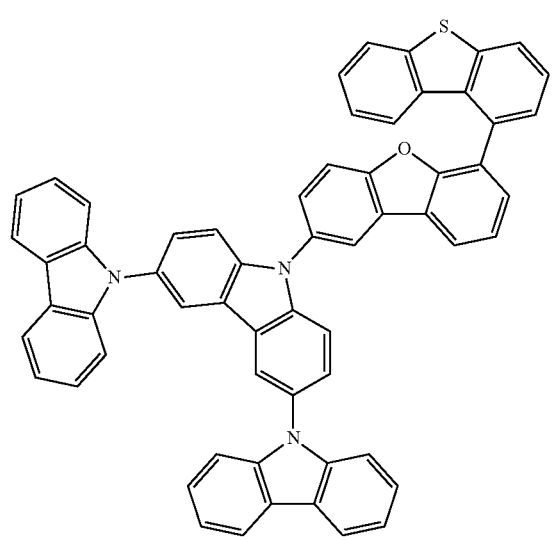
TH-34
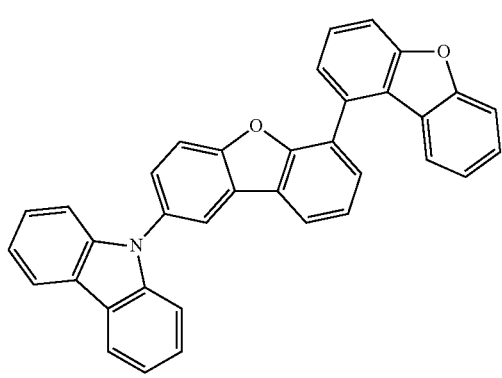
TH-35
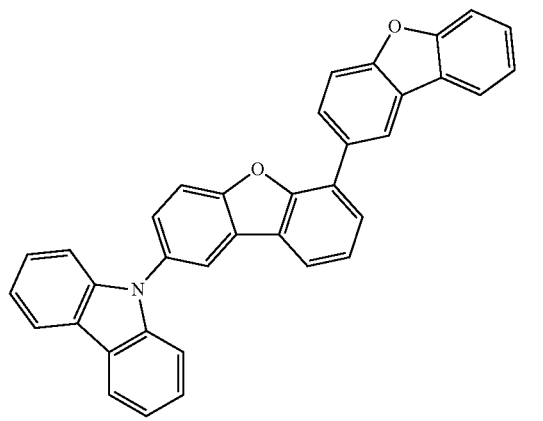
TH-36
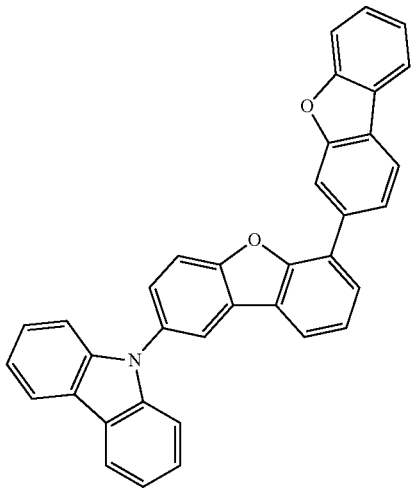
TH-37
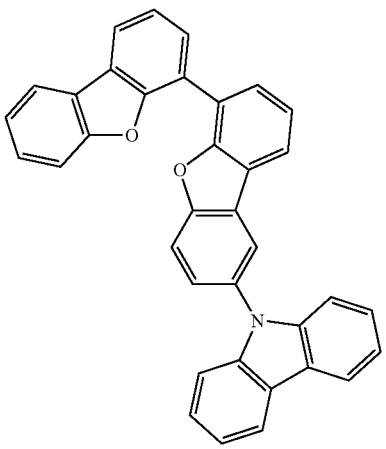
TH-38
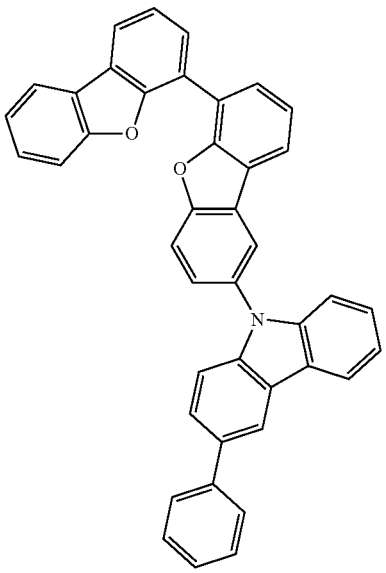

TH-39
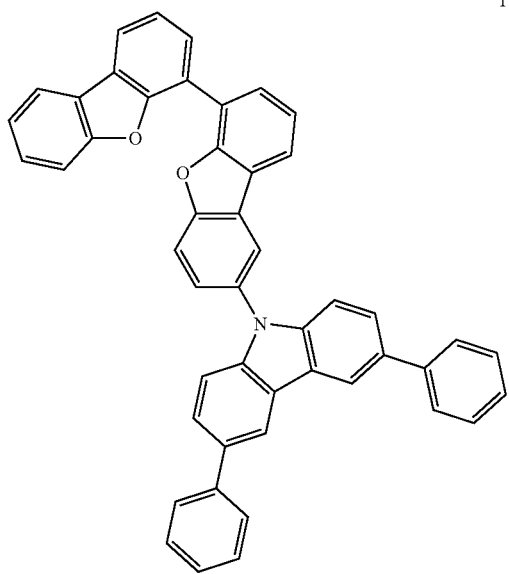
TH-40
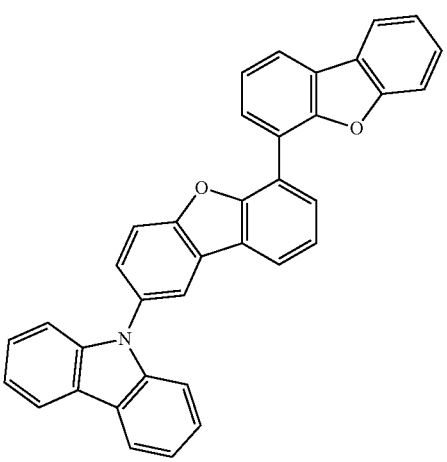
TH-41
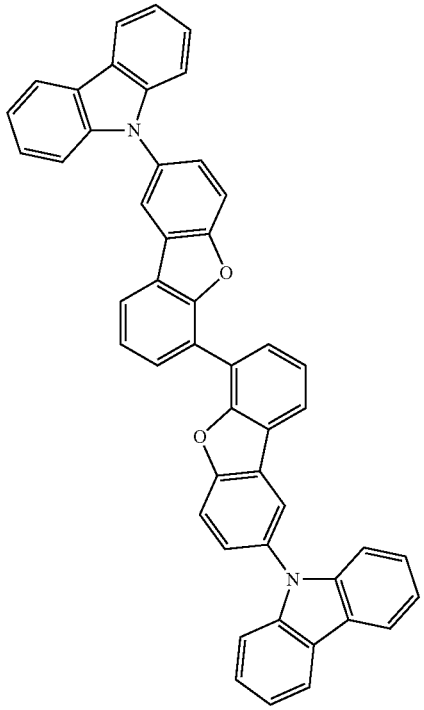
TH-42
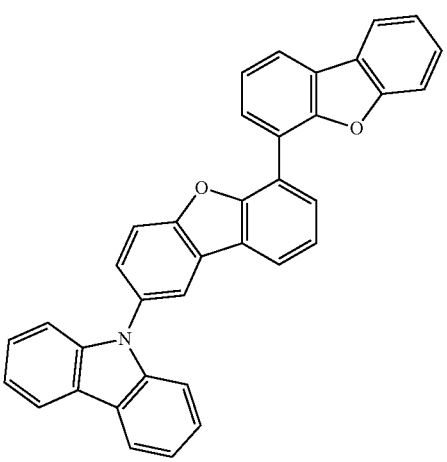
TH-43
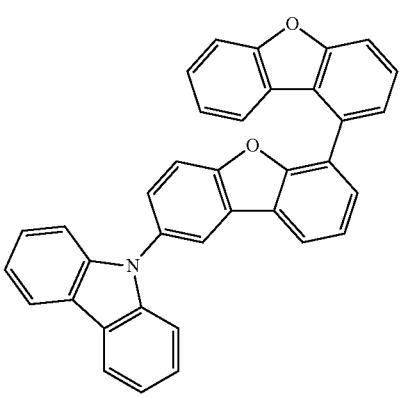

-continued
TH-44
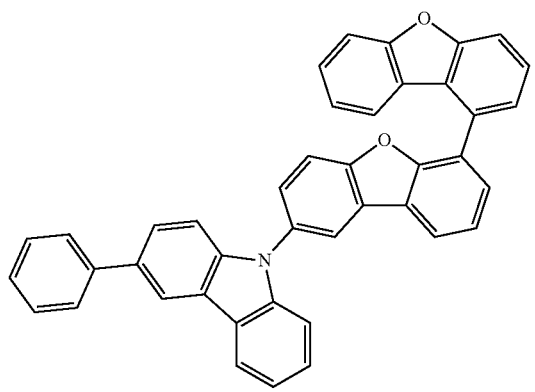
TH-45
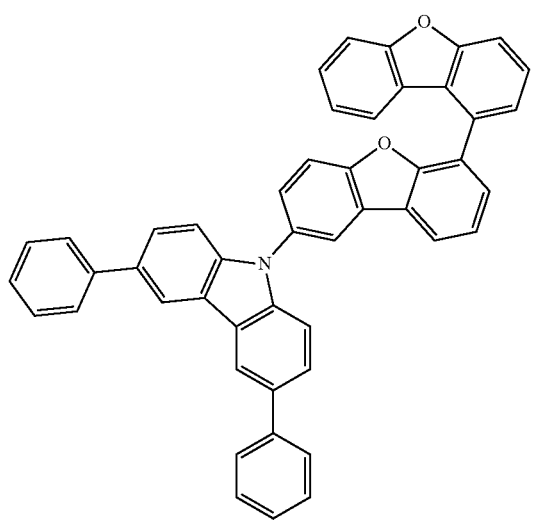
TH-46
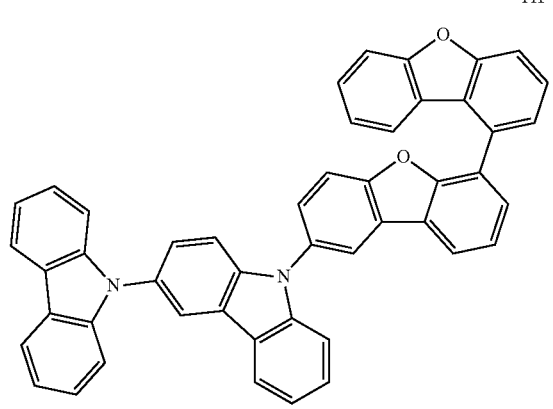
-continued
TH-47
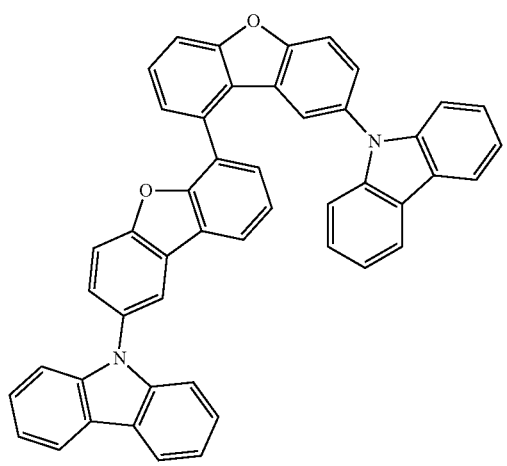
TH-48
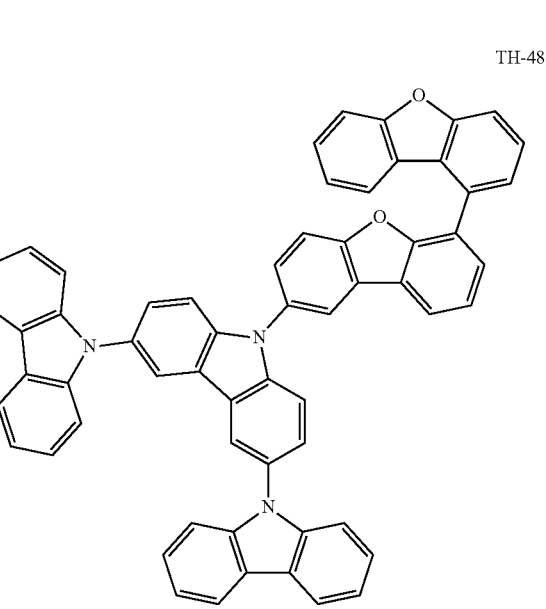
TH-49
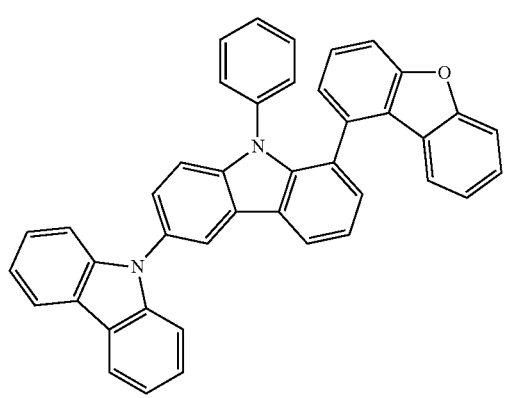

-continued

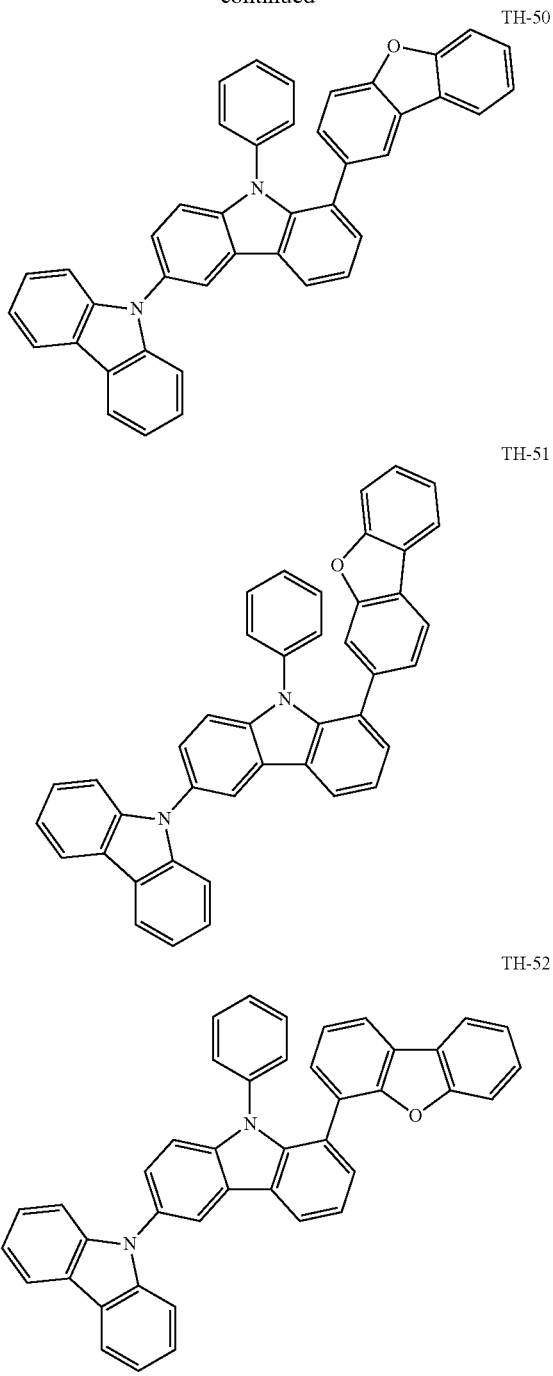

TH-50

TH-51

TH-52

The third compound having the structure of anyone in Chemical Formulae 4 to 6 includes the carbazolyl moiety linked to the central first dibenzofuranyl/dibenzothiophenyl moiety and having p-type property, and the second dibenzofuranyl/dibenzothiophenyl moiety linked to the first dibenzofuranyl/dibenzothiophenyl moiety and having n-type property, and the carbazolyl moiety and the second dibenzofuranyl/dibenzothiophenyl moiety are linked to the first dibenzofuranyl/dibenzothiophenyl moiety asymmetrically.

In other words, each of the carbazolyl moiety having p-type property and the second dibenzofuranyl/dibenzothiophenyl moiety having n-type property is bonded to an asymmetrical position in each side benzene ring constituting the first dibenzofuranyl/dibenzothiophenyl moiety, so that the third compound having the structure of anyone in Chemical Formulae 4 to 6 may exhibit more amorphous property so as to substantially improve heat resistance. Accordingly, the crystallization caused by Joule's heat in driving the OLED 300 is prevented, and the structure of the OLED 300 is not destroyed.

Moreover, since the third compound having the structure of anyone in Chemical Formulae 4 to 6 includes the carbazolyl moiety and dibenzofuranyl/dibenzothiophenyl moieties, each of which includes two benzene rings, the first compound has a HOMO energy level and a LUMO energy level proper for use as the host in the EML 360. Particularly, when the third compound is used together with a delayed fluorescent material and a fluorescent material in the EML 360, it is possible to transfer exciton energy to the fluorescent material without energy loss during the emission process.

In other words, the third compound having the structure of any one in Chemical Formulae 3 to 6 can be used as the host in the EML2 364 of the OLED 300 to enhance luminous efficiency, to lower driving voltage and to improve the luminous life span of the OLED 300. As an example, when the third compound having the structure of anyone in Chemical Formulae 3 to 6 is used as the host in the EML2 364, it is possible to minimize exciton quenching owing to an interaction between the exciton in the host and a peripheral polaron and to prevent the luminous life span of the OLED 300 being lowered due to electro-oxidation and photo-oxidation.

Moreover, the third compound having the structure of any one in Chemical Formulae 3 to 6 has excellent heat resistance property and a large energy level bandgap and high triplet energy level. Accordingly, when the third compound having the structure of any one in Chemical Formulae 3 to 6 is used as the host in the EML2 364, the third compound call transfer efficiently exciton energy to the luminous material so that the OLED 300 may have enhanced luminous efficiency. In addition, the third compound in the EML2 364 is not deteriorated by heat, so that the OLED 300 having a long life span and excellent color purity can be realized.

The EML1 362 further includes the second compound which may be the fluorescent or phosphorescent material and the EML2 364 further includes the fourth compound which may be the delayed fluorescent material in which the first luminescence occurs. As described above, since the delayed fluorescent material can exhibit 100% internal quantum efficiency in theory, it can realize high luminous efficiency as the conventional phosphorescent material including the heavy metal. However, due to the bond conformation between the electron acceptor-electron donor and the sterical twists in the delayed fluorescent material, and additional charge transfer transition (CT transition) caused by them. In other words, the delayed fluorescent material emits light based upon CT luminescence mechanism.

Since the delayed fluorescent material shows emission wavelength having very broad FWHM due to the luminescence property attributed to the CT luminescence mechanism, it has a limit to be applied to a display device in terms of color purity. In other words, since the delayed fluorescent material such as TADF uses triplet exciton energy, it has a short luminous life spat. In addition, since the delayed fluorescent material emits light by the CT luminescence mechanism, its FWHM is very wide, which limit the color purity. Moreover, since the delayed fluorescent material uses triplet energy as well as singlet energy during the emission process, its luminous life span is very short.

To solve the limitations of the delayed fluorescent material, the hyper-fluorescence uses the delayed fluorescent material to increase the ratio of singlet-exciton generation in the fluorescent material capable of utilizing only the singlet exciton. Since the delayed fluorescent material can utilize the triplet energy as well as the singlet energy, when the exciton energy of the delayed fluorescent material is released, the fluorescent material absorbs the exciton energy, and then the fluorescent material utilized the absorbed exciton energy with generating only 100% singlet excitons. Accordingly, energy transfer from the delayed fluorescent material to the fluorescent material is most important in order to improve the luminous efficiency of the diode including the fluorescent material where ultimate luminescence occurs during the hyper-fluorescence mechanism. The EML1 362 may include the second compound, which may be the fluorescent or phosphorescent material, so as to prevent the color purity and life span being lowered when the delayed fluorescent material is used, and thereby, realizing hyper-fluorescence or hyper-phosphorescence.

In one exemplary embodiment, when the second compound is the fluorescent material, each of the excited state singlet energy levels $S_1^{FD}$ and the excited stat triplet energy levels $T_1^{FD}$ of the second compound in the EML1 362 is lower than each of the excited state singlet energy level $S_1^{TD}$ and the excited state triplet energy level $T_1^{TD}$ of the fourth compound, which may be the delayed fluorescent material, in the EML2 364. When the second and fourth compound satisfy the singlet and triplet energy levels, the triplet energy of the fourth compound, which may be the delayed fluorescent material, is converted to the singlet energy by RISC mechanism, and the converted singlet energy of the fourth compound in the EML2 364 can be efficiently transferred to the second compound in the EML1 362, which is disposed adjacently to the EML2 364, via FRET mechanism.

In an alternative exemplary embodiment, when the second compound is the phosphorescent material, the excited state singlet energy level $S_1^{TD}$ of the fourth compound, which may be the delayed fluorescent material, may not be higher than an excited state singlet energy level of the second compound. However, the excited state triplet energy level $T_1^{TD}$ of the fourth compound may be higher than the excited state singlet energy level of the fourth compound as the phosphorescent material.

In one exemplary embodiment, the second compound, which may be the fluorescent or phosphorescent material, may be a compound having an absorption wavelength range that has a large spectral overlap with an emission wavelength range of the fourth compound, which may be the delayed fluorescent material. In this case, the energy transfer efficiency from the delayed fluorescent material to the fluorescent or phosphorescent material is improved, thereby maximizing the luminous efficiency of the OLED 300. In addition, since the final luminescence in the EML 360 occurs as the second compound transitions from the excited state to the ground state, it may be preferable to use a compound having a narrow FWHM as the second compound.

In one exemplary embodiment, the second compound as the fluorescent material may include, but are not limited to, anyone of the following structure of Chemical Formula 7.

Chemical Formula 7

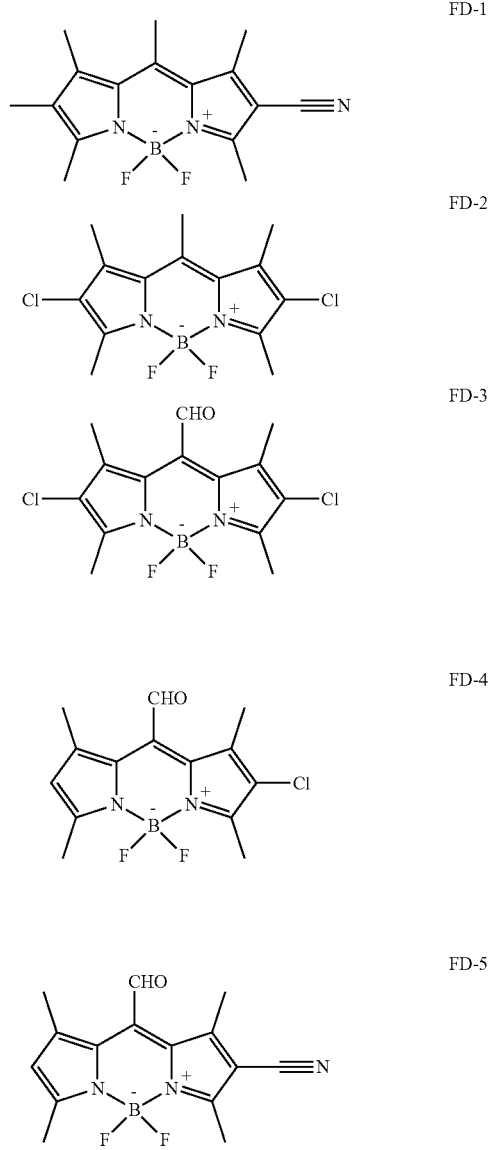

Each of the organic compounds having the structure of Chemical Formula 6 has energy levels as follows: FD-1 (LUMO: −3.0 eV; HOMO: −6.0 eV; $S_1$: 2.5 eV; $T_1$: 2.3 eV); FD-2 (LUMO: −2.7 eV; HOMO: −5.7 eV; $S_1$: 2.5 eV; $T_1$: 2.3 eV); FD-3 (LUMO: −3.3 eV; HOMO: −5.9 eV; $S_1$: 2.4 eV, $T_1$: 2.2 eV); FD-4 (LUMO: −3.2 eV; HOMO: −5.8 eV; $S_1$: 2.5 eV; $T_1$: 2.3 eV); and FD-5 (LUMO: −3.4 eV; HOMO: −6.1 eV; $S_1$: 2.6 eV; $T_1$: 2.4 eV).

In an alternative embodiment, the second compound as the phosphorescent material may include any metal complex capable of emitting green light. As an example, the second compound as the phosphorescent material may include, but are not limited to, anyone of the following structure of Chemical Formula 8.

Chemical Formula 8

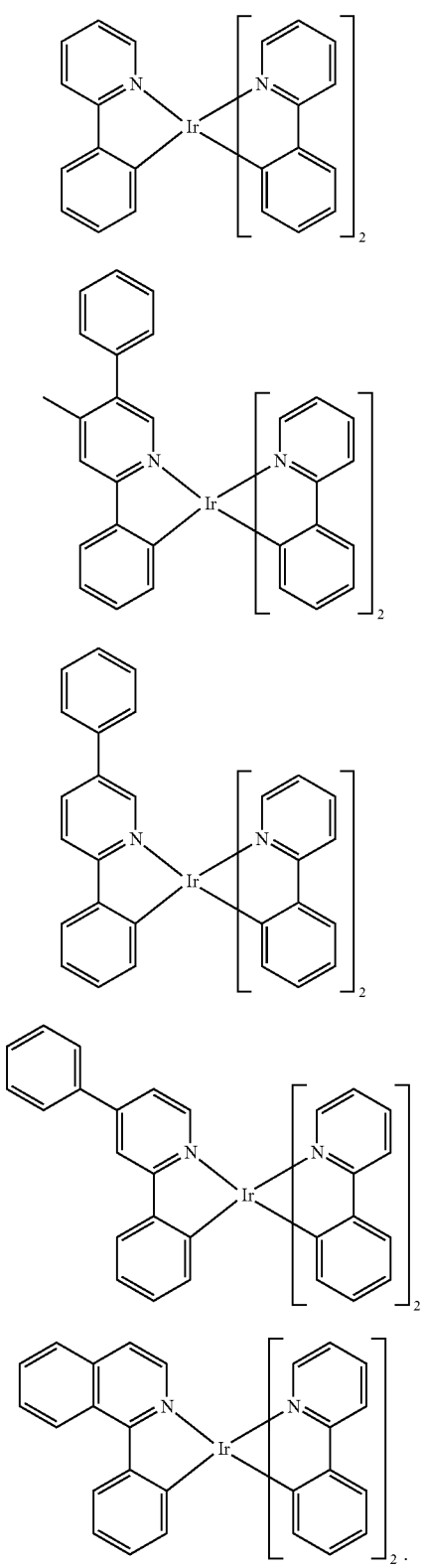

Each of the compounds having the structure of Chemical Formula 8 has energy levels as follows: PD-1 (LUMO: −3.0 eV; HOMO: −6.0 eV; $S_1$: 2.8 eV; $T_1$: 2.4 eV); PD-2 (LUMO: −3.0 eV; HOMO: −5.9 eV; $S_1$: 2.6 eV; $T_1$: 2.4 eV); PD-3 (LUMO: −3.2 eV; HOMO: −5.8 eV; $S_1$: 2.6 eV; $T_1$: 2.3 eV); PD-4 (LUMO: −3.1 eV; HOMO: −5.8 eV; $S_1$: 2.4 eV; $T_1$: 2.2 eV); and PD-5 (LUMO: −3.2 eV; HOMO: −5.6 eV; $S_1$: 2.3 eV; $T_1$: 2.0 eV).

The EML2 364 includes the fourth compound, which may be the delayed fluorescent material. The fourth compound may have proper energy levels as compared to the first to third compounds. As an example, the fourth compound having the delayed fluorescent property may include an electron acceptor moiety and an electron donor moiety separated from the electron acceptor moiety via proper linkers (e.g. arylene or hetero arylene group such as phenylene group and the likes). In one exemplary embodiment, the fourth compound may include a triazine moiety and/or an aromatic or hetero aromatic moiety substituted with at least one cyano group. As an example, the fourth compound may include, but are not limited to, anyone of the following structure of Chemical Formula 9.

Chemical Formula 9

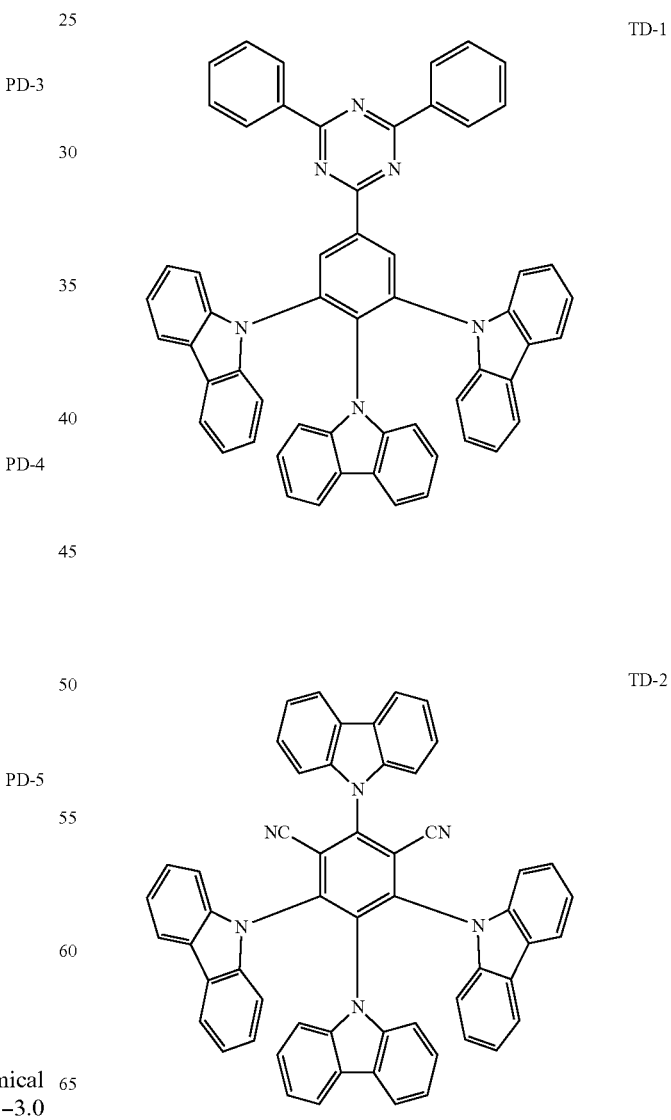

-continued

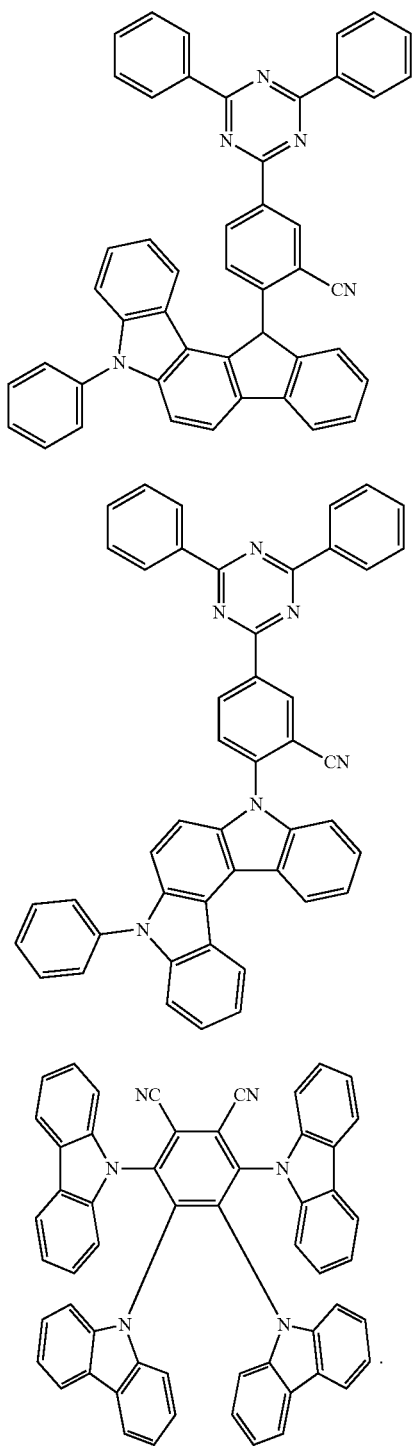

Each of the organic compounds having the structure of Chemical Formula 9 has energy levels as follows: TD-1 (TczTrz; 9,9',9''-(5-(4,6-diphenyl-1,3,5-triazin-2-yl)benzene-1,2,3-triyl) tris(9H-carbazole); LUMO: −2.8 eV; HOMO: −5.8 eV; $S_1$: 3.0 eV; $T_1$: 2.8 eV); TD-2 (4CzIPN; 2,4,5,6-Tetra(9H-carbazol-9-yl)isophthalonitrile; LUMO: −3.4 eV; HOMO: −5.9 eV; $S_1$: 2.7 eV; $T_1$: 2.6 eV); TD-3 (LUMO: −3.2 eV; HOMO: −5.8 eV; $S_1$: 2.6 eV; $T_1$: 2.5 eV); TD-4 (LUMO: −3.2 eV; HOMO: −5.8 eV; $S_1$: 2.4 eV; $T_1$: 2.2 eV), and TD-5 (LUMO: −3.4 eV; HOMO: −5.8 eV; $S_1$: 2.3 eV; $T_1$: 2.1 eV).

In one exemplary embodiment, the weight ratio of the first compound may be larger than the weight ratio of the second compound in the EML1 362. As an example, the EML1 362 may include the first compound by about 70 to about 99 wt %, preferably about 90 to about 99 wt %, and the second compound by about 1 to about 30 wt %, preferably about 1 to about 10 wt %.

In contrast, the weight ratio of the third compound may be equal to or larger than the weight ratio of the fourth compound in the EML2 364. As an example, the EML2 may include the third compound by about 50 to about 95 wt %, preferably about 60 to about 80 wt %, and the fourth compound by about 5 to about 50 wt %, preferably about 20 to about 40 wt %.

In alternative embodiment, the weight ratio of the fourth compound, which may be the delayed fluorescent material, in the EML2 364 may be larger than the weight ratio of the second compound, which may be the fluorescent or phosphorescent material, in the EML1 362. In this case, enough exciton energy can be transferred from the fourth compound in the EML2 364 to the second compound in the EML1 362.

In one embodiment, each of the EML1 362 and the EML2 364 may be laminated with a thickness of, but are not limited to, about 5 nm to about 10 nm, preferably about 10 nm to about 30 nm, more preferably about 10 nm to 20 nm.

Referring to FIG. 2, The ETL 370 and the ETL 380 are laminated sequentially between the EML 360 and the second electrode 320. The ETL 370 includes a material having high electron mobility so as to provide electrons stably with the EML 360 by fast electron transportation.

In one exemplary embodiment, the ETL 370 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the likes.

As an example, the ETL 370 may include, but is not limited to, tris-(8-hydroxyquinoline aluminum (Alq$_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthro line (Bphen), 2,9-Bis(naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)] (PFNBr) and/or tris(phenylquinoxaline) (TPQ).

The EIL 380 is disposed between the second electrode 320 and the ETL 370, and can improve physical properties of the second electrode 320 and therefore, can enhance the life span of the OLED 300. In one exemplary embodiment, the EIL 380 may include, but are not limited to, an alkali halide such as LiF, CsF, NaF, BaF$_2$ and the likes, and/or an organic metal compound such as lithium benzoate, sodium stearate, and the like.

In one exemplary embodiment, each of the ETL 370 and the EIL 380 may be respectively laminated with a thickness of, but are not limited to, about 10 nm to about 200 nm, preferably about 10 nm to about 100 nm.

When holes are transferred to the second electrode 320 via the EML 360 and/or electrons are transferred to the first electrode 310 via the EML 360, the OLED 300 may have short lifespan and reduced luminous efficiency. In order to prevent these phenomena, the OLED 300 in accordance with the first embodiment of the present disclosure may have at least one exciton blocking layer adjacent to the EML 360.

For example, the OLED 300 of the exemplary embodiment includes the EBL 355 between the HTL 350 and the EML 360 so as to control and prevent electron transfers. In one exemplary embodiment, the EBL 355 may include, but are not limited to, TCTA, Tris[4-(diethylamino)phenyl]amine, N-(bipnehyl-4-yl)-9,9-dimethyl-N-(4-(9-phenyl-9H-carbazol-3-yl)phenyl)-9H-fluorene-2-amine, TAPC, MTDATA, 1,3-Bis(carbazol-9-yl)benzene (mCP), 3,3'-bis(N-carbazolyl)-1,1'-biphenyl (mCBP), CuPc, N,N'-bis[4-(bis(3-methylphenyl)amino)phenyl]-N,N'-diphenyl-[1,1'-biphenyl]-4,4'-diamine (DNTPD) and/or TDAPB.

In addition, the OLED 300 further includes the HBL 375 as a second exciton blocking layer between the EML 360 and the ETL 370 so that holes cannot be transferred from the EML 360 to the ETL 370. In one exemplary embodiment, the HBL 375 may include, but are not limited to, oxadiazole-based compounds, triazole-based compounds, phenanthroline-based compounds, benzoxazole-based compounds, benzothiazole-based compounds, benzimidazole-based compounds, and triazine-based compounds.

As an example, the EBL 375 may include a compound having a relatively low HOMO energy level compared to the emitting material in EML 360. For example, the HBL 375 may include, but are not limited to, BCP, BAlq, $Alq_3$, PBD, spiro-PBD, Liq, Bis-4,5-(3,5-di-3-pyridylphenyl)-2-methylpyrimidine (B3PYMPM), Oxybis(2,1-phenylene))bis(diphenylphosphine oxide (DPEPO) and combination thereof.

As an example, each of the EBL 355 and the HBL 375 may be respectively laminated with a thickness of, but are not limited to, about 5 nm to about 200 nm, preferably about 10 nm to about 100 nm.

Figure 6:
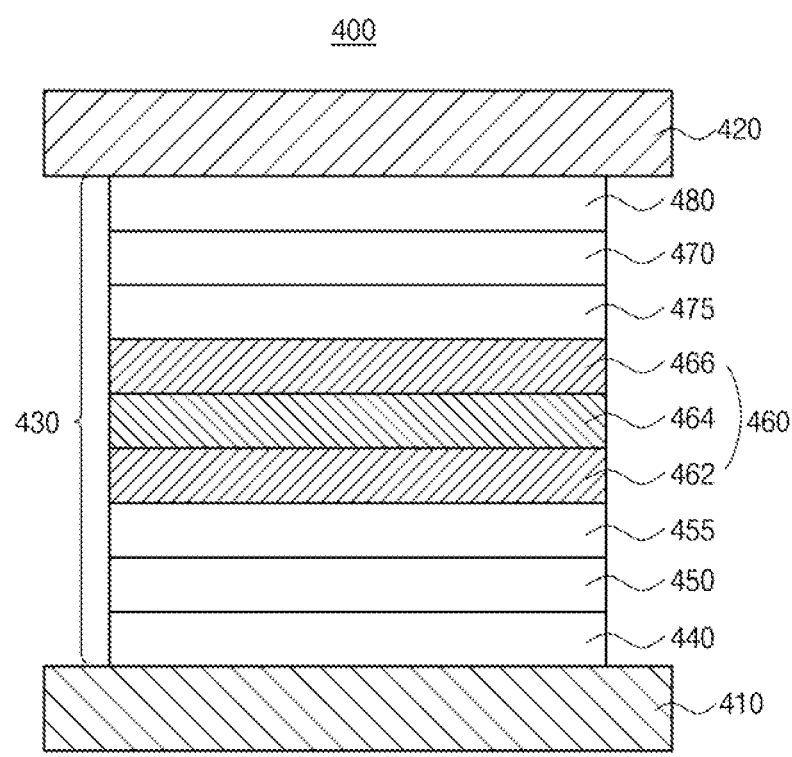
FIG. 6 is a schematic cross-sectional view illustrating an organic light emitting diode in accordance with another exemplary embodiment of the present disclosure.

An OLED may have three or more layered emitting material layers. FIG. 6 is a schematic cross-sectional view illustrating an organic light emitting diode in accordance with another exemplary embodiment of the present disclosure.

As illustrated in FIG. 6, the OLED 400 in accordance with the second embodiment of the present disclosure includes first and second electrodes 410 and 420 facing each other and an emitting unit 430 as an emissive layer disposed between the first and second electrodes 410, 420.

In one exemplary embodiment, the emitting unit 430 includes a HIL 440, a HTL 450, an EML 460, an ETL 470 and an EIL 480 each of which is laminated sequentially from the first electrode 410. Besides, the emitting unit 430 may further include a first exciton blocking layer, i.e. an EBL 455 disposed between the HTL 450 and the EML 460 and/or a second exciton blocking layer, i.e., a HBL 475 disposed between the EML 460 and the ETL 470.

As described above, the first electrode 410 may be an anode and include, but are not limited to, a conductive material having a relatively large work function values such as ITO, IZO, SnO, ZnO, ICO, AZO, and the like. The second electrode 420 may be a cathode and may include, but are not limited to, a conductive material having a relatively small work function values such as Al, Mg, Ca, Ag, alloy thereof or combination thereof. Each of the first and second electrodes 410 and 420 may be laminated with a thickness of, but are not limited to, about 30 nm to about 300 nm.

The HIL 440 is disposed between the first electrode 410 and the HTL 450. The HIL 440 may include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 440 may be omitted in compliance with the structure of the OLED 400.

The HTL 450 may be disposed adjacently to the EML 460 between the first electrode 410 and the EML 460. The HTL 450 may include, but are not limited to, aromatic amine derivatives such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. In one embodiment, each of the HIL 440 and the HTL 450 may be laminated with a thickness of, but are not limited to, about 5 nm to about 200 nm, preferably about 5 nm to about 100 nm.

The EML 460 includes a first EML (EML1) 462, a second EML (EML2) 464 and a third EML (EML3) 466. The EML1 462 is disposed between the first and second electrodes 410 and 420 and includes a first compound and a second compound. The EML2 464 is disposed on the EML1 462 and includes a third compound and a fourth compound. The EML3 464 is disposed on the EML2 464 and includes a fifth compound and a sixth compound.

In one exemplary embodiment, the first compound may be a first host and the second compound may be a fluorescent or phosphorescent material in the EML1 462. The third compound may be a second host and the fourth compound may be a delayed fluorescent material in the EML2 464. The fifth compound may be a third host and the sixth compound may be a fluorescent or phosphorescent material in the EML3 466. As an example, each of the first and fifth compounds may be a fluorescent host, respectively, and the third compound may be a phosphorescent host.

It is possible to lower driving voltage, thereby reducing power consumption, to improve luminous efficiency and color purity, and to enhance luminous life span of the OLED 400, by using first to sixth compounds, as the luminous materials, whose energy levels are controlled within predetermined ranges. Hereinafter, The OLED 400, where the first compound is the first host, the second and sixth compounds are fluorescent dopant (FD), the third compound is the second host, the fourth compound is the delayed fluorescent dopant (TD), and the fifth compound is the third host, will be explained in detail.

The EML2 464 includes the fourth compound, which may be the delayed fluorescent material. Accordingly, when the triplet exciton energy of the fourth compound in the EML2 464 is converted to its own singlet exciton energy by RISC mechanism, the converted singlet exciton energy of the fourth compound can be transferred to the second and sixth compounds, each of which may be the fluorescent or phosphorescent material, in the EML1 462 and the EML3 466, each of which is disposed adjacently to the EML2 464, via FRET mechanism. Accordingly, the OLED 400 enhances its luminous efficiency and color purity.

Figure 7:
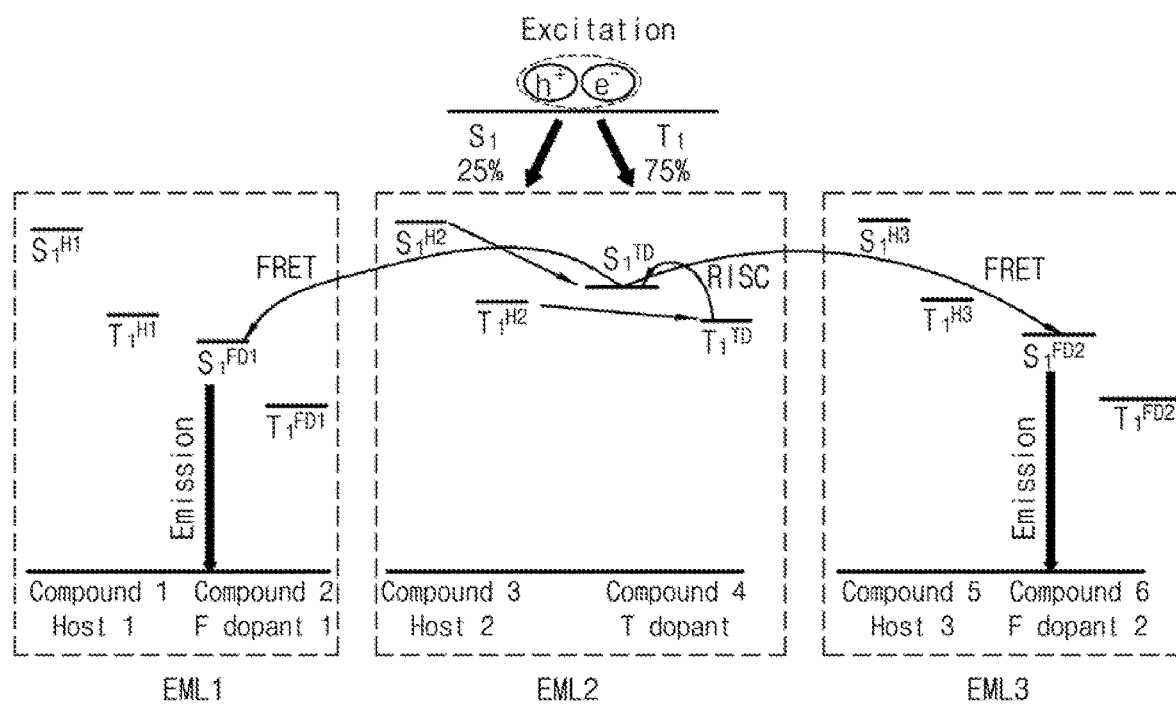
FIG. 7 is a schematic cross-sectional view illustrating an organic light emitting diode in accordance with another exemplary embodiment of the present disclosure.

In order to such an exciton energy transfer mechanism, it is necessary to exciton energies generated in the first, third and fifth compounds, each of which may be the host, can be firstly transferred to the fourth compound, which may be the delayed fluorescent materials, to realize first luminescence. FIG. 7 is a schematic cross-sectional view illustrating an organic light emitting diode in accordance with another exemplary embodiment of the present disclosure.

As illustrated in FIG. 7, each of excited state singlet energy levels $S_1^{H1}$, $S_1^{H2}$ and $S_1^{H3}$ and excited state triplet energy levels $T_1^{H1}$, $T_1^{H2}$ and $T_1^{H3}$ of the first, third and fifth compounds, each of which may be the first, second and third host, respectively, should be higher than each of an excited state singlet energy level $S_1^{TD}$ and an excited state triplet energy level $T_1^{TD}$ of the fourth compound, which may be the delayed fluorescent materials, respectively.

As an example, when the excited state triplet energy level $T_1^{H1}$ of the first compound, the excited state triplet energy level $T_1^{H2}$ of the third compound and the excited state triplet energy level $T_1^{H3}$ of the fifth compound are not sufficiently higher than the excited state triplet energy level $T_1^{TD}$ of the fourth compound, the excitons of the triplet state $T_1^{TD}$ of the fourth compound, which may be the delayed fluorescent material, can be reversely transferred to the excited state triplet energy levels $T_1^{H1}$, $T_1^{H2}$ and $T_1^{H3}$ of the first, third and fifth compounds, each of which may be the host. Accordingly, the excitons of the triplet state $T_1^{TD}$ of the fourth compound may be quenched as a non-emission in the first, third and fifth compounds, which cannot use the triplet exciton energy, and therefore, the triplet exciton energy generated in the fourth compound cannot be involved in the emission process. For example, each of the excited state triplet energy levels $T_1^{H1}$, $T_1^{H2}$ and $T_1^{H3}$ of the first, third and fifth compounds may be high by at least 0.2 eV compared to the excited state triplet energy level $T_1^{TD}$ of the fourth compound.

In addition, each of the excited state triplet energy level $T_1^{H1}$ of the first compound, which may be the first host, and the excited state triplet energy level $T_1^{H3}$ of the fifth compound, which may be the third host, may be higher than the excited state triplet energy level $T_1^{H2}$ of the third compound, which may be the second host. In this case, the exciton energy generated in the third compound may be efficiently transferred to the fourth compound, which may be the delayed fluorescent material, without being transferred to the first and fifth compounds where the exciton energies are quenched as a non-emission.

In addition, it may be necessary to transfer energy from the fourth compound, i.e. the delayed fluorescent material, in which excitons of singlet and triplet energy levels are converted to the ICT state by RISC, in the EML2 464 to the second and sixth compounds, each of which may be the fluorescent or phosphorescent material, in the EML1 462 and in the EML3 466 so as to realize an OLED having high luminous efficiency and color purity. In order to implement such an OLED, each of the excited state singlet energy level $S_1^{TD}$ and the excited state triplet energy level $T_1^{TD}$ of the fourth compound, which may be delayed fluorescent materials, in the EML2 464 is higher than each of the excited state singlet energy levels $S_1^{FD1}$ and $S_1^{FD2}$ and the excited stat triplet energy levels $T_1^{FD1}$ and $T_1^{FD2}$ of the second and sixth compounds, each of which is the fluorescent material, in the EML1 462 and in the EML3 466, respectively.

Alternatively, when each of the second in the EML1 462 and the sixth compound in the EML2 466 is a phosphorescent material, the excited state singlet energy level $S_1^{TD}$ of the fourth compound, which may be the delayed fluorescent material, may not be higher than each of excited state singlet energy levels of the second and sixth compounds. However, the excited state triplet energy level $T_1^{TD}$ of the fourth compound may be higher than each of the excited state singlet energy levels of the second and sixth compounds as the phosphorescent material.

Moreover, each of the excited state singlet energy level $S_1H^1$ of the first compound, which may be the first host, and the excited state singlet energy level $S_1^{H3}$ of the fifth compound, which may be the third host, is higher than each of the excited state singlet energy levels $S_1^{FD1}$ and $S_1^{FD2}$ of the second and sixth compounds, each of which may be the fluorescent material, respectively, in order to prevent the exciton energy transferred from the fourth compound to the second and sixth compounds from being transferred to the first and fifth compounds and to realize efficient luminescence. In an exemplary embodiment, each of the excited state triplet energy levels $T_1^{H1}$ and $T_1^{H3}$ of the first and fifth compound may be higher than each of the excited state triplet energy levels $T_1^{FD1}$ and $T_1^{FD2}$ of the second and sixth compounds, respectively. The fourth compound must have an energy level bandgap $\Delta E_{ST}^{TD}$ between the excited stated singlet energy level $S_1^{TD}$ and the excited state triplet energy level $T_1^{TD}$ equal to or less than about 0.3 eV in order to realized delayed fluorescence (see, FIG. 3).

Figure 8:
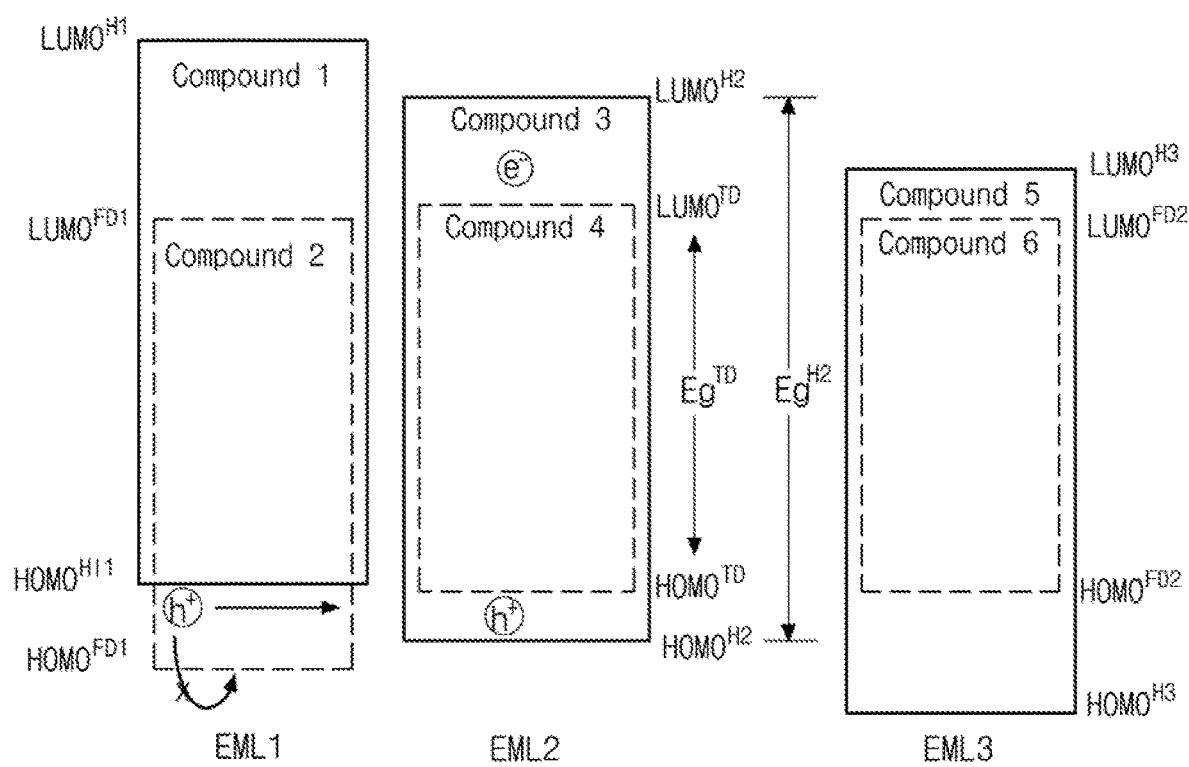
FIG. 8 is a schematic diagram illustrating HOMO energy levels and LUMO energy levels among the luminous materials in the EML in accordance with another exemplary embodiment of the present disclosure.

Moreover, it may be necessary to adjust the HOMO energy levels and/or LUMO energy levels of the luminous materials, i.e. the first to sixth compounds in the EML1 462, the EML2 464 and the EML3 466 in order to prevent excitons from not being formed when holes and electrons cannot be injected in the EML 460 in a balance manner, and to prevent non-emissive quenching of the formed excitons when an exciplex between the host and the dopant is formed. FIG. 8 is a schematic diagram illustrating HOMO energy levels and LUMO energy levels among the luminous materials in the EML in accordance with another exemplary embodiment of the present disclosure.

As illustrated in FIG. 8, a HOMO energy level HOMO$^{H1}$ of the first compound, which may be the first host having a fluorescent property, is higher or shallower than a HOMO energy level HOMO$^{FD1}$ of the second compound, which may be the fluorescent or phosphorescent material, in the EML1 462. Accordingly, when holes injected from the first electrode 410 (See, FIG. 6) are transported to the EML2 464 via the EML1 462, hole trapping by the second compound in the EML1 462 is prevented. As a result, holes and electrons are injected into the EML2 464 in a balanced manner to reduce amounts of the non-emissive quenched charges.

In contrast, a HOMO energy level HOMO$^{H2}$ of the third compound, which may be the second host having a phosphorescent property, is lower or deeper than a HOMO energy level HOMO$^{TD}$ of the fourth compound, which may be the delayed fluorescent material. Optionally, a LUMO energy level LUMO$^{H2}$ of the third compound is higher than a LUMO energy level LUMO$^{TD}$ of the fourth compound. Since an exciplex between the third compound, which may be the second host, and the fourth compound, which may be the delayed fluorescent material, is not formed, the triple exciton energy of the fourth compound cannot be quenched as a non-emission.

In addition, the HOMO energy level HOMO$^{H1}$ of the first compound, which may be the first host included in the EML1 462, is higher than the HOMO energy level HOMO$^{H2}$ of the third compound, which may be the second host included in the EML2 464. As a result, holes can be efficiently transferred from the first compound in the EML1 462 to the third compound in the EML2 464.

Moreover, the LUMO energy level LUMO$^{H1}$ of the first compound, which may be the first host included in the EML1 462, is higher than the LUMO energy level LUMO$^{H2}$ of the third compound, which may be the second host in the EML2 464. Accordingly, electrons injected into the EML2 464 from the ETL 470 (see, FIG. 6) do not transport to the EML1 462.

Particularly, the EML3 464 disposed on the EML2 462 may have the fifth and sixth compounds whose energy levels are controlled within predetermined ranges. As an example, a HOMO energy level HOMO$^{H3}$ of the fifth compound, which may be the third host in the EML3 466, is lower or deeper than a HOMO energy level HOMO$^{FD2}$ of the sixth compound, which may be the fluorescent or phosphorescent material. Optionally, a LUMO energy level LUMO$^{H3}$ of the fifth compound is higher or shallower than a LUMO energy level LUMO$^{FD2}$ of the sixth compound.

Moreover, the HOMO energy level HOMO$^{H3}$ of the fifth compound, which may the third host, is lower than the HOMO energy level HOMO$^{H2}$ of the third compound, which may be the second host. When the HOMO energy level HOMO$^{H3}$ of the fifth compound is higher than the HOMO energy level HOMO$^{H2}$ of the third compound, holes are leaked into the EML3 466 from the EML2 462, so that light emission occurs only in the sixth compound as the fluorescent material. Accordingly, the OLED 400 may have reduced luminous efficiency because the fluorescent material has only 25% internal quantum efficiency.

On the other hand, since the HOMO energy level HOMO$^{H3}$ of the fifth compound is less than the HOMO energy level HOMO$^{H2}$ of the third compound, holes injected into the EML2 464 is not leaked to the EML3 466. In this case, since the fourth compound, which may be the delayed fluorescent material having 100% internal quantum efficiency in theory, can perform luminescence, the OLED 400 may maximize its luminous efficiency. As an example, the fifth compound may be formed as the same material as the HBL 475 (see, FIG. 6). In this case, the HBL 475 may be omitted.

In addition, the LUMO energy level LUMO$^{H3}$ of the fifth compound in the EML3 466 is lower than the LUMO energy level LUMO$^{H2}$ of the third compound in the EML2 464. When the LUMO energy level LUMO$^{H3}$ of the fifth compound is higher than the LUMO energy level LUMO$^{H2}$ of the third compound, electron injection from the ETL 470 (see, FIG. 6) to the EML3 466 may be delayed. In this case, holes and electrons are not injected in the EML2 462 in a balanced manner, so that the luminous efficiency and life span of the OLED 300 may be reduced.

In one exemplary embodiment, the first compound, which may be the first host, may include, but are not limited to, any organic compound having the structure of Chemical Formulae 1 and 2. The second compound, which may be the second host, may include, but are not limited to, any organic compound having the structure of Chemical Formulae 3 to 6. Each of the second and sixth compounds may independently include, but are not limited to, a fluorescent material having the BODIPY core and/or the quinolino-acridine core, for example, any one of the fluorescent material having the structure of Chemical Formula 7 and/or any one of the phosphorescent material having the structure of Chemical Formula 8. Also, the fourth compound, which may be the delayed fluorescent material, may include, but are not limited to, any one of the organic compound having the structure of Chemical Formula 9.

In one exemplary embodiment, the fifth compound, which may be the second host, may also be the same as the HBL 475. As an example, the fifth compound may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. For example, the fifth compound may include, but are not limited to, a compound having relatively low HOMO energy level as compared to the third compound in the EML2 464, such as BCP, BAlq, Alq3, PBD, spiro-PBD, LIQ, B3PYMPY, DPEPO and combination thereof.

As an example, each of the weight ratio of the first compound in the EML1 462 and the weight ratio of the fifth compound in the EML3 466 may be larger than each of the weight ratio of the second and sixth compounds in the same EMLs, respectively. As an example, each of the EML1 462 and the EML3 466 may include each of the first and fifth compounds by about 70 to about 99 wt %, preferably about 90 to about 99 wt %, and each of the second and sixth compounds by about 1 to about 30 wt %, preferably about 1 to about 10 wt %, respectively.

In contrast, the weight ratio of the third compound may be equal to or larger than the weight ratio of the fourth compound in the EML2 464. As an example, the EML2 may include the third compound by about 50 to about 95 wt %, preferably about 60 to about 80 wt %, and the fourth compound by about 5 to about 50 wt %, preferably about 20 to about 40 wt %.

In an alternative embodiment, the weight ratio of the fourth compound, which may be the delayed fluorescent material, in the EML2 464 may be larger than the weight ratio of the second and sixth compounds, each of which may be the fluorescent or phosphorescent material, in the EML1 462 or in the EML3 466. In this case, enough exciton energy can be transferred from the fourth compound in the EML2 464 to the second compound in the EML1 462 and the sixth compound in the EML3 466.

In one embodiment, each of the EML1 462 and the EML2 464 may be laminated with a thickness of, but are not limited to, about 5 nm to about 10 nm, preferably about 10 nm to about 30 nm, more preferably about 10 nm to 20 nm. In contrast, the EML3 466 may be laminated with a thickness of, but is not limited to, about 2 nm to about 30 nm, preferably about 2 nm to about 20 nm.

Referring to FIG. 6, the ETL 470 is disposed between the EML 460 and the EIL 480. For example, the ETL 470 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. For example, the ETL 470 may include, but is not limited to, Alq$_3$, PBD, spiro-PBD, Liq, TPBi, BAlq, Bphen, NBphen, BCP, TAZ, NTAZ, TpPyPB, TmPPPyTz, PFNBr, and/or TPQ.

The EIL 480 is disposed between the second electrode 420 and the ETL 470. The ETL 480 may include, but is not limited to, an alkali halide such as LiF, CsF, NaF, BaF$_2$ and the like, and/or an organic metal compound such as lithium benzoate, sodium stearate, and the like. As an example, each of the ETL 470 and the EIL 480 may be laminated with a thickness of, but are not limited to, about 10 nm to about 200 nm, preferably about 10 nm to about 100 nm.

Moreover, the OLED 400 may further include at least one exciton blocking layer such as the EBL 455 and the HBL 475 each of which is disposed adjacently to the EML 460.

As an example, the EBL 455 may include, but is not limited to, TCTA, Tris[4-(diethylamino)phenyl]amine, N-(bipnehyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD and/or TDAPB.

The HBL 475 may include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 475 may include, but are not limited to, BCP, BAlq, Alq$_3$, PBD, spiro-PBD, Liq, B3PYMPM, DPEPO and combination thereof. As an example, each of the EBL 455 and the HBL 475 may be laminated with a thickness of, but are not limited to, about 5 nm to about 200 nm, preferably about 10 nm to about 100 nm.

Synthesis Example 1: Synthesis of Compound TH-17

(1) Synthesis of Intermediate 1-1

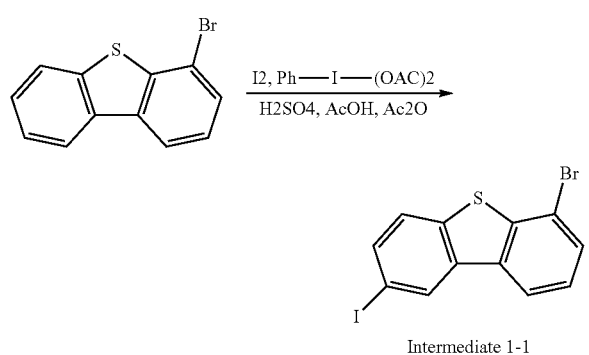

Intermediate 1-1

10.0 g (38.0 mmol) of 4-bromo dibenzothiophene, 4.8 g (19.0 mmol) of iodine and 6.2 g (19.0 mmol) of phenyl iodide diacetate were placed in a mixed solvent of 150 mL of acetic acid and 150 mL of acetic anhydride under nitrogen atmosphere. Three drops of sulfuric acid was added dropwise in the solution and then stirred 10 hours at room temperature. After the reaction was completed, ethyl acetate was added into the mixed solution, and then the solution was washed with water to separate an organic layer from an aqueous layer. Anhydrous magnesium sulfate was added to the organic solution and the organic solution was stirred again. After the solution was filtered with a silica pad, the solution was concentrated under reduced pressure and purified by column chromatography to give an Intermediate 1-1 (yield: 65%).

(2) Synthesis of Intermediate 1-2

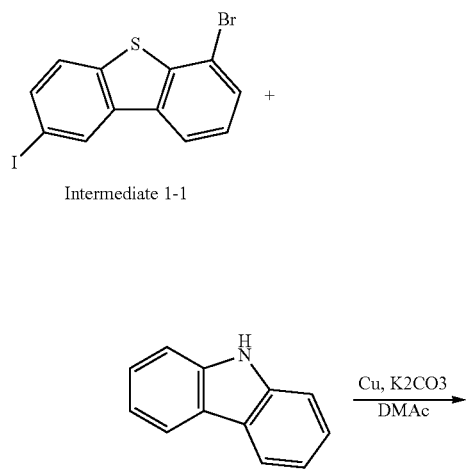

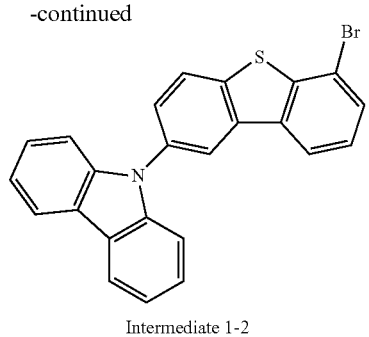

Intermediate 1-2

9.6 g (24.7 mmol) of Intermediate 1-1, 2.1 g (12.3 mmol) of carbazole, 1.9 g (30.5 mmol) of copper powder and 3.6 g (24.7 mmol) of potassium carbonate was added into 70 mL of dimethyl acetoamide, and the solution was stirred for 24 hours at 130° C. After the reaction was completed, the temperature was dropped to room temperature. The solution was filtered with silica pad to remove copper powder. The obtained solution was washed with water to separate an organic layer from an aqueous layer. Anhydrous magnesium sulfate was added into the organic solution and the solution was stirred again. After the solution was filtered with silica pad, the solution was concentrated under reduced pressure and purified by column chromatography to give an Intermediate 1-2 (yield: 70%).

(3) Synthesis of Compound TH-17

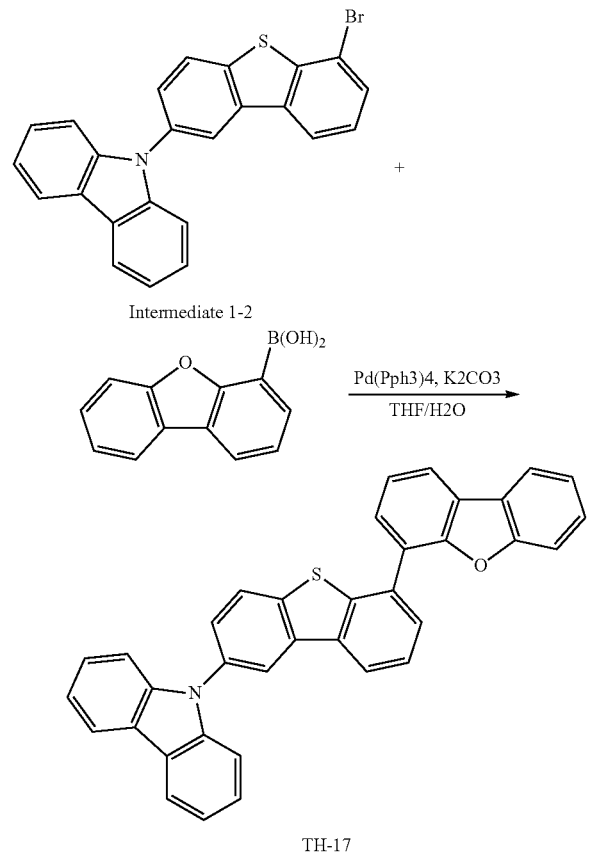

TH-17

7.3 g (17.0 mmol) of Intermediate 1-2, 4.0 g (18.7 mmol) of 4-dibenzothienyl-boronic acid and 2 mol % of Tetrakis (triphenylphosphine) palladium (Pd(PPh₃)₄) was added into 50 mL of tetrahydrofuran. 40.86 mmol of potassium carbonate was dissolved in 25 mL of water and the aqueous solution was mixed with the organic solution. The mixed solution was stirred for 12 hours at 80° C. After the reaction was completed, and then the temperature was dropped to room temperature to separate an organic layer from an aqueous layer. Anhydrous magnesium sulfate was added into the organic layer and the organic solution was stirred again. After the organic solution was filtered with silica pad, the solution was concentrated under reduced pressure and purified by column chromatography to give Compound TH-17 (yield: 70%).

Synthesis Example 2: Synthesis of Compound TH-27

(1) Synthesis of Intermediate 2-1

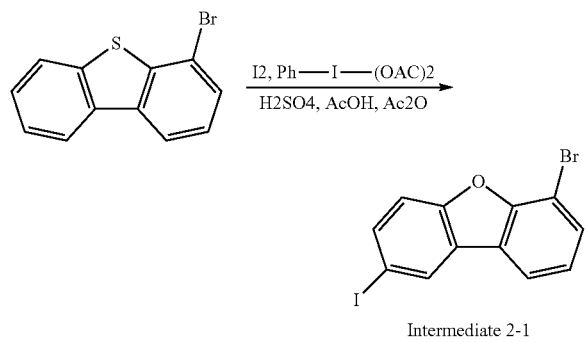

Intermediate 2-1

10.0 g (40.65 mmol) of 4-bromo dibenzofuran, 5.1 g (20.32 mmol) of iodine and 6.6 g (20.32.mmol) of phenyl iodide diacetate were placed in a mixed solvent of 150 mL of acetic acid and 150 mL of acetic anhydride under nitrogen atmosphere. Three drops of sulfuric acid was added drop wisely in the solution and then stirred 10 hours at room temperature. After the reaction was completed, ethyl acetate was added into the mixed solution, and then the solution was washed with water to separate an organic layer from an aqueous layer. Anhydrous magnesium sulfate was added to the organic solution and the organic solution was stirred again. After the solution was filtered with silica pad, the solution was concentrated under reduced pressure and purified by column chromatography to give an Intermediate 2-1 (yield: 65%).

(2) Synthesis of Intermediate 2-2

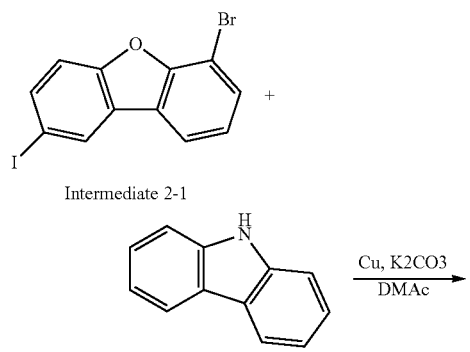

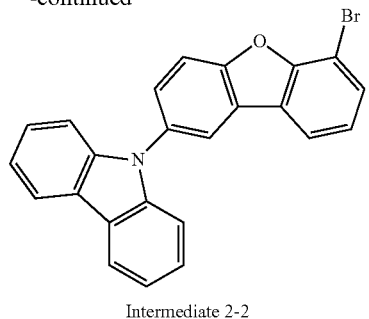

Intermediate 2-2

9.8 g (26.35 mmol) of Intermediate 2-1, 2.2 g (13.18 mmol) of carbazole, 2.0 g (32.53 mmol) of copper powder and 3.6 g (26.35 mmol) of potassium carbonate was added into 70 mL of dimethyl acetoamide, and the solution was stirred for 24 hours at 130° C. After the reaction was completed, the temperature was dropped to room temperature. The solution was filtered with a silica pad to remove copper powder. The obtained solution was washed with water to separate an organic layer from an aqueous layer. Anhydrous magnesium sulfate was added into the organic solution and the solution was stirred again. After the solution was filtered with silica pad, the solution was concentrated under reduced pressure and purified by column chromatography to give an Intermediate 2-2 (yield: 78%).

(3) Synthesis of Compound TH-27

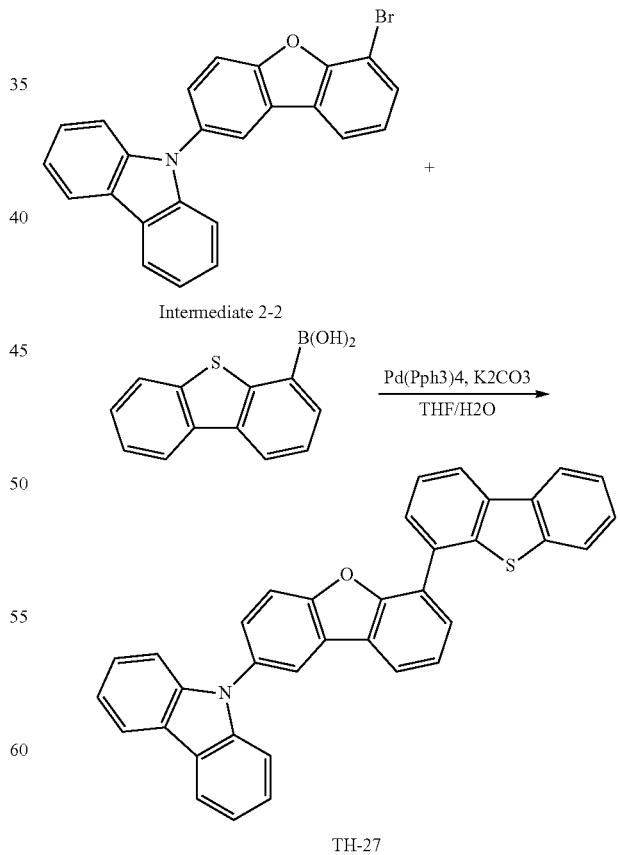

TH-27

Synthetic reaction was performed as the same process and condition as Example 1, except using 8.4 g (20.43 mmol) of Intermediate 2-2 and 5.12 g (22.47 mmol) of dibenzo[b,d]thiophene-4-yl-bornic acid as reactants to give Compound TH-27 (yield 60%).

Synthesis Example 3: Synthesis of Compound TH-34

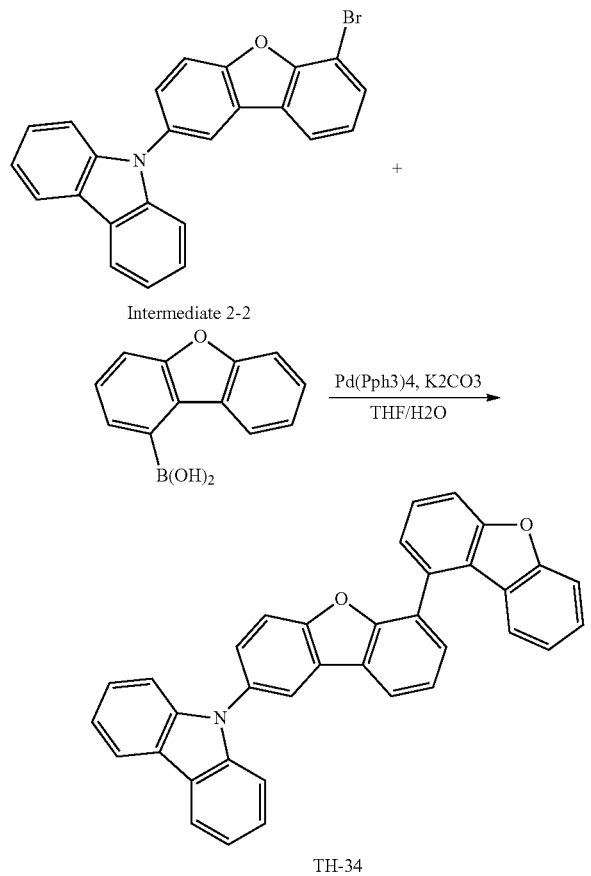

TH-34

Synthetic reaction was performed as the same process and condition as Example 1 except that 8.4 g (20.43 mmol) of Intermediated 2-2 and 4.76 g (22.47 mmol) of dibenzo[b,d]thiophen-1-yl-bornic acid were used as reactants to give Compound TH-34 (yield: 57%).

Synthesis Example 4: Synthesis of Compound TH-42

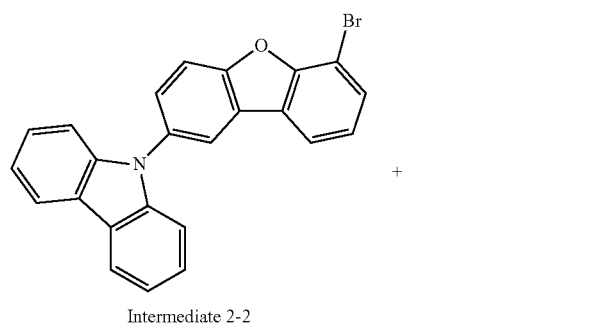

Intermediate 2-2

-continued

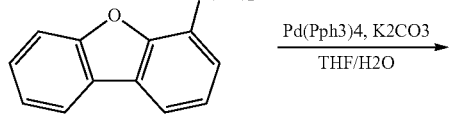

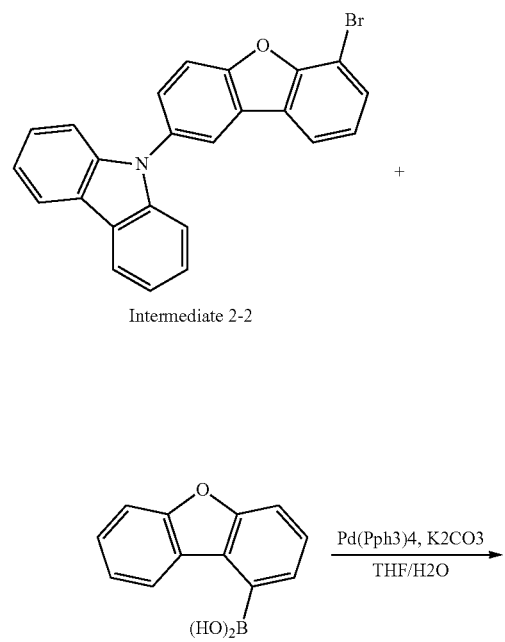

TH-42

Synthetic reaction was performed as the same process and condition as Example 1 except that 8.4 g (20.43 mmol) of Intermediated 2-2 and 4.76 g (22.47 mmol) of dibenzo[b,d]fruan-4-yl-bornic acid were used as reactants to give Compound TH-42 (yield: 60%).

Synthesis Example 5: Synthesis of Compound TH-43

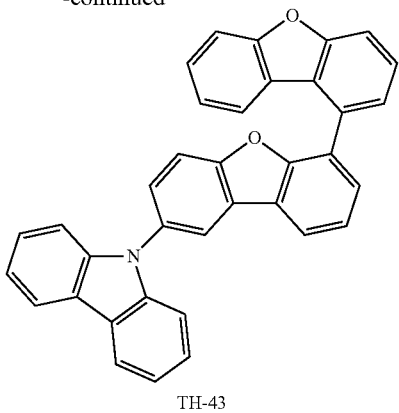

TH-43

Synthesis reaction was performed as the same process and condition as Example 1 except that 8.4 g (20.43 mmol) of Intermediate 2-2 and 4.76 g (22.47 mmol) of dibenzo[b,d]fruan-1-yl-bornic acid were used as reactants to give Compound TH-42 (yield: 60%).

Synthetic reaction was performed as the same process and condition as Example 1 except that 4.0 g (6.94 mmol) of Intermediate 5-1 and 1.62 g (7.63 mmol) of dibenzo[b,d]furan-4-yl-boronic acid were used as reactants to give Compound 5 (yield: 64%).

Experimental Example 1: Measurement of Energy Levels of Organic Compound

LUMO energy levels, HOMO energy levels, singlet energy levels $S_1$ and triplet energy levels $T_1$ were measured each for FH-1, FH2 and FH-3 in Chemical Formula 2, each of which may be used as the first compound in EML; TH-17, TH-27 and TH-42, each of which was synthesized respectively in Examples 1, 2 and 4 and may be used as the third compound in EML; FD-1 to FD-5 in Chemical Formula 7 and PD-1 to PD-5 in Chemical Formula 8 each of which may be used as the second compound in EML; and TD-1 to TD-5 in Chemical Formula 8 each of which may be used as the fourth compound in EML. Also, HOMO energy levels and LUMO energy levels were measured each for the reference compounds "Ref.1", "Ref.2", "Ref.3" and "Ref.4" as indicated below. Table 1 indicates the measurement results.

[Reference Compounds]

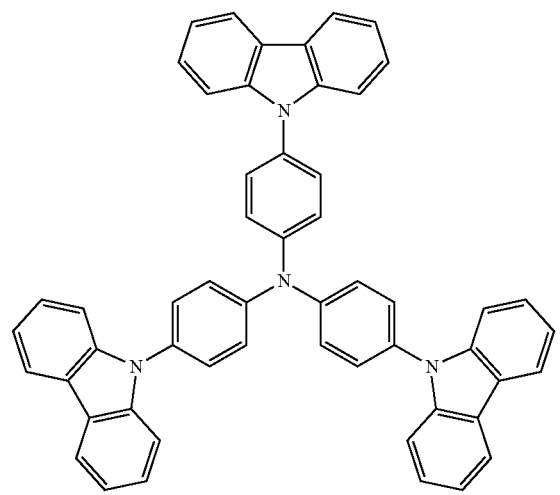

Ref.1

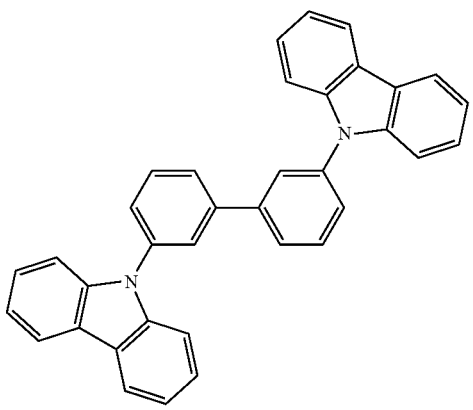

Ref.2

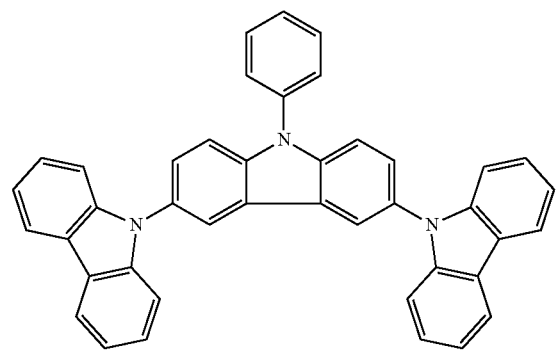

Ref.3

-continued

Ref.4

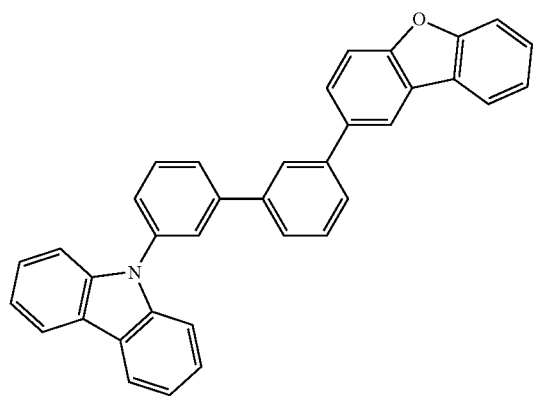

TABLE 1

| Energy Level of Organic Compounds | | | | |
|---|---|---|---|---|
| Compound | HOMO (eV) | LUMO (eV) | $S_1$ (eV) | $T_1$ (eV) |
| FH-1 | −5.6 | −2.2 | 3.4 | 2.8 |
| FH-2 | −5.6 | −2.3 | 3.2 | 2.9 |
| FH-3 | −5.6 | −2.3 | 3.2 | 2.8 |
| TH-17 | −6.0 | −2.4 | 3.2 | 2.9 |
| TH-27 | −6.0 | −2.3 | 3.1 | 2.8 |
| TH-42 | −6.0 | −2.5 | 3.1 | 2.9 |
| FD-1 | −6.0 | −3.0 | 2.5 | 2.3 |
| FD-2 | −5.7 | −2.7 | 2.5 | 2.3 |
| FD-3 | −5.9 | −3.3 | 2.4 | 2.2 |
| FD-4 | −5.8 | −3.2 | 2.5 | 2.3 |
| FD-5 | −6.1 | −3.4 | 2.6 | 2.4 |
| PD-1 | −6.0 | −3.0 | 2.8 | 2.4 |
| PD-2 | −5.9 | −3.0 | 2.7 | 2.4 |
| PD-3 | −5.8 | −3.2 | 2.6 | 2.3 |
| PD-4 | −5.8 | −3.1 | 2.4 | 2.2 |
| PD-5 | −5.6 | −3.2 | 2.3 | 2.0 |
| TD-1 | −5.8 | −2.8 | 3.0 | 2.8 |
| TD-2 | −5.9 | −3.4 | 2.7 | 2.6 |
| TD-3 | −5.8 | −3.2 | 2.6 | 2.5 |
| TD-4 | −5.8 | −3.2 | 2.4 | 2.2 |
| TD-5 | −5.8 | −3.4 | 2.3 | 2.1 |
| Ref. 1 | −5.6 | −2.2 | — | — |
| Ref. 2 | −5.6 | −2.2 | — | — |
| Ref. 3 | −6.1 | −2.5 | — | — |
| Ref. 4 | −6.0 | −2.5 | — | — |

HOMO: Film (100 nm/ITO), by AC3.
LUMP: Calculated at Film absorption edge.

Example 1: Manufacture of Organic Light Emitting Diode (OLED)

An organic light emitting diode was manufactured using "FH-1" as a first host ($1^{st}$ compound) and "FD-1" in Chemical 6 as a fluorescent material ($2^{nd}$ compound) in EML1, "TH-17" as a second host ($3^{rd}$ compound) and "TD-2", i.e. 4CzIPN as a delayed fluorescent material ($4^{th}$ compound) in EML2, and B3PYPM as a third host ($5^{th}$ compound) and "FD-1" as a fluorescent material ($6^{th}$ compound) in EML3.

A glass substrate, to which ITO electrode (including a reflective plate) was attached and which has a size of 40 nm×40 nm×0.5 mm, was washed by ultra-sonication using isopropyl alcohol, acetone and DI (distilled water) as a cleaning solvent for 5 minutes and dried in an oven at 100° C. After cleaning the substrate, the substrate was treated $O_2$ plasma for 2 minutes and was transferred to a vacuum chamber for depositing emitting layer. Subsequently, an emissive layer and a cathode were deposited by evaporation from a heating boat under $10^{-7}$ Torr vacuum condition as the following order:

A hole injection layer (HIL) (HAT-CN; 7 nm); a hole transport layer (HTL) (NPB, 78 nm); an electron blocking layer (EBL) (TAPC; 15 nm); a first emitting material layer (EML1) (FH-1 99 wt %, FD-1 1 wt %; 10 nm); a second emitting material layer (EML2) (TH-17 70 wt %, 4CzIPN 30 wt %; 20 nm); a third emitting material layer (EML3) (B3PYMPM 99 wt %, FD-1 1 wt %; 5 nm; S 1: 4.01 eV); a hole blocking layer (HBL) (B3PYMPM; 10 nm); an electron transport layer (ETL) (TPBi; 30 nm); an electron injection layer (EIL) (LiF; 0.8 nm); and a cathode (Al; 100 nm).

And then, cappling layer (CPL) was deposited over the cathode and the device was encapsualted by glass. After deposition of emissve layer and the cathode, the OLED was transferred from the depostion chamber to a dry box for film formation, followed by encapsulation using UV-curable epoxy and moisture getter. The manufacture organic light emitting diode had an emision area of 9 mm².

Example 2: Manufacture of OLED

An OLED was manufactured as the same process and the same material as Example 1, except that "TH-27" was used in place of "TH-17" as the second host in the EML2.

Example 3: Manufacture of OLED

An OLED was manufactured as the same process and the same material as Example 1, except that "TH-42" was used in place of "TH-17" as the second host in the EML2.

Example 4: Manufacture of OLED

An OLED was manufactured as the same process and the same material as Example 1, except that "FH-2" was used in place of "FH-1" as the first host in the EML1.

Example 5: Manufacture of OLED

An OLED was manufactured as the same process and the same material as Example 1, except that "FH-2" was used in place of "FH-1" as the first host in the EML1 and "TH-27" was used in place of "TH-17" as the second host in the EML2.

Example 6: Manufacture of OLED

An OLED was manufactured as the same process and the same material as Example 1, except that "FH-2" was used in place of "FH-1" as the first host in the EML1 and "TH-42" was used in place of "TH-17" as the second host in the EML2.

Example 7: Manufacture of OLED

An OLED was manufactured as the same process and the same material as Example 1, except that "FH-3" was used in place of "FH-1" as the first host in the EML1.

Example 8: Manufacture of OLED

An OLED was manufactured as the same process and the same material as Example 1, except that "FH-3" was used in place of "FH-1" as the first host in the EML1 and "TH-27" was used in place of "TH-17" as the second host in the EML2.

Example 9: Manufacture of OLED

An OLED was manufactured as the same process and the same material as Example 1, except that "FH-3" was used in place of "FH-1" as the first host in the EML1 and "TH-42" was used in place of "TH-17" as the second host in the EML2.

Comparative Example 1: Manufacture of OLED

An OLED was manufactured as the same process and the same material as Example 1, except that "Ref. 1" was used in place of "FH-1" as the first host in the EML1 and "Ref. 2" was used in place of "TH-17" as the second host in the EML2.

Comparative Example 2: Manufacture of OLED

An OLED was manufactured as the same process and the same material as Example 1, except that "Ref. 3" was used in place of "FH-1" as the first host in the EML1 and "Ref. 4" was used in place of "TH-17" as the second host in the EML2.

Comparative Example 3: Manufacture of OLED

An OLED was manufactured as the same process and the same material as Example 1, except that "Ref. 3" was used in place of "FH-1" as the first host in the EML1 and "Ref. 1" was used in place of "TH-17" as the second host in the EML2.

Experimental Example 2: Measurement of Luminous Properties of OLED

Each of the OLED manufactured in Examples 1 to 9 and Comparative Examples 1 to 3 was connected to an external power source, and luminous properties of all the diodes were evaluated using a constant current source (KEITHLEY) and a photometer PR650 at room temperature. In particular, driving voltage (V), current efficiency (cd/A), power efficiency (lm/W), external quantum efficiency (EQE; %) and color coordinates at a current density of 10 mA/cm$^2$ and luminous life span, i.e. a time period until brightness is reduced to 95% at 3000 nit of the OLED were measured. The measurement results thereof are indicated in the following Table 2.

TABLE 2

| Sample | Luminous Properties of OLED | | | | | | |
|---|---|---|---|---|---|---|---|
| | @ 10 mA/cm$^2$ | | | | | | @ 3,000 nit |
| | V | cd/A | lm/W | EQE (%) | CIE_x | CIE_y | T$_{95}$ |
| Comparative Example 1 | 3.5 | 4.8 | 4.3 | 2.0 | 0.42 | 0.54 | 3 |
| Comparative Example 2 | 5.1 | 31.8 | 19.5 | 10.1 | 0.27 | 0.66 | 6 |
| Comparative Example 3 | 6.5 | 38.0 | 18.4 | 12.3 | 0.27 | 0.64 | 1 |
| Example 1 | 4.4 | 55.1 | 39.1 | 17.3 | 0.33 | 0.62 | 50 |
| Example 2 | 4.5 | 56.3 | 39.6 | 18.3 | 0.33 | 0.62 | 68 |
| Example 3 | 4.5 | 56.4 | 39.7 | 18.3 | 0.33 | 0.62 | 87 |
| Example 4 | 4.5 | 58.0 | 40.5 | 18.6 | 0.34 | 0.62 | 50 |
| Example 5 | 4.6 | 58.5 | 39.6 | 18.5 | 0.33 | 0.63 | 61 |
| Example 6 | 4.6 | 57.0 | 38.8 | 18.3 | 0.34 | 0.62 | 82 |
| Example 7 | 4.7 | 59.2 | 39.5 | 18.7 | 0.33 | 0.63 | 43 |
| Example 8 | 4.8 | 51.2 | 34.4 | 16.2 | 0.33 | 0.63 | 55 |
| Example 9 | 4.9 | 58.8 | 38.1 | 18.1 | 0.33 | 0.63 | 55 |

As indicated in Table 2, As compared to the OLEDs manufactured in the Comparative Examples, the OLED applying three luminous materials whose energy level was controlled within the predetermined ranges into the EML of Examples 1 to 9 has reduced driving voltage maximally by 6.0%. Besides, compared to the OLEDs in the Comparative Examples 1 to 3, the OLEDs in the Examples 1 to 9 have enhanced current efficiency up to 12.3 times, power efficiency up to 9.2 times, external quantum efficiency up to 9.35 times and luminous life span up to 27.3 times. In addition, it was confirmed that the OLEDs in the Examples 1 to 9 emits light closer to green than the OLEDs in the Comparative Examples in terms of color purity. It is possible to reduce the driving voltage, to improve the luminous efficiency and life span of the OLED by applying a multi-layered EML including two or more hosts and two or more luminous materials whose energy levels are controlled with the predetermined ranges.

Example 10: Manufacture of OLED

An OLED was manufactured as the same process and the same material as Example 3, except that the thickness of the EML1 is changed to 20 nm and the thickness of the EML2 is changed 10 nm.

Example 11: Manufacture of OLED

An OLED was manufactured as the same process and the same material as Example 3, except that the thickness of the EML1 is changed to 15 nm and the thickness of the EML2 is changed to 15 nm.

Example 12: Manufacture of OLED

An OLED was manufactured as the same process and the same material as Example 3, except that the EML2 includes TH-17 by 80 wt % in place of 70 wt % and 4CzIPN 20 wt % in place of 30 wt %.

Example 13: Manufacture of OLED

An OLED was manufactured as the same process and the same material as Example 3, except that the EML2 includes TH-17 by 60 wt % in place of 70 wt % and 4CzIPN 40 wt % in place of 30 wt %.

Experimental Example 3: Measurement of Luminous Properties of OLED

Luminous properties for each of the OLED manufactured in Example 3 and 10-12 were measured as the same process as Experimental Example 2. The measurement results are indicted in the following Table 3. Compared with the case where the EML2 is thicker than the EML1, when the EML2 is thinner that the EML1, the luminous efficiency and the lifespan of the OLED are largely reduced. When the EML1 has a thickness as the same as the EML2, the luminous efficiency and life span of the OLED was slightly reduced. However, all of the OLEDs in Examples 3 and 9 to 13 maintained superior luminous properties compared to the OLEDs in the Comparative Examples. When the doping concentration of the delayed fluorescent material, i.e. 4CzIPN in the EML2 is reduced to 20 wt %, the luminous efficiency and life span of the OLED were greatly reduced. On the other hand, even if the doping concentration of 4CzIPN in the EML2 is increased to 40 wt %, the luminous efficiency was substantially similar to the case in which 4CzIPN is doped to 30 wt % and only the life span of the OLED was slightly reduced.

TABLE 3

Luminous Properties of OLED

@ 10 mA/cm²

| Sample | V | cd/A | lm/W | EQE (%) | CIE_x | CIE_y | @ 3,000 nit $T_{95}$ |
|---|---|---|---|---|---|---|---|
| Example 3 | 4.5 | 56.4 | 39.7 | 18.3 | 0.33 | 0.62 | 87 |
| Example 10 | 4.3 | 40.6 | 29.4 | 12.1 | 0.36 | 0.62 | 30 |
| Example 11 | 4.3 | 49.9 | 36.4 | 15.1 | 0.35 | 0.62 | 41 |
| Example 12 | 4.3 | 25.8 | 18.8 | 7.7 | 0.36 | 0.61 | 20 |
| Example 13 | 4.4 | 52.6 | 37.8 | 17.2 | 0.36 | 0.60 | 57 |

Example 3: EML1 10 nm, EML2 20 nm, 4CzIPN 30 wt % in EML2.
Example 10: EML1 20 nm, EML2 10 nm, 4CzIPN 30 wt % in EML2
Example 11: EML1 15 nm, EML2 15 nm, 4CzIPN 30 wt % in EML2
Example 12: EML1 10 nm, EML2 20 nm, 4CzIPN 20 wt % in EML2
Example 13: EML1 10 nm, EML2 20 nm, 4CzIPN 40 wt % in EML2

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. An organic light emitting diode, comprising:
a first electrode and a second electrode, wherein the first electrode and the second electrode face each other; and
an emitting material layer disposed between the first and second electrodes,
wherein the emitting material layer includes a first emitting material layer and a second emitting material layer, the first emitting material layer including a first compound and a second compound, and the second emitting material layer including a third compound and a fourth compound,
wherein an excited state singlet energy level of the first compound is higher than an excited state singlet energy level of the second compound,
wherein an excited state singlet energy level and an excited state triplet energy level of the third compound are each higher than an excited state singlet energy level and an excited state triplet energy level of the fourth compound, respectively,
wherein a Highest Occupied Molecular Orbital (HOMO) energy level of the first compound is higher than a HOMO energy level of the second compound,
wherein the first compound comprises an organic compound having the following structure of Chemical Formula 1:

Chemical Formula 1

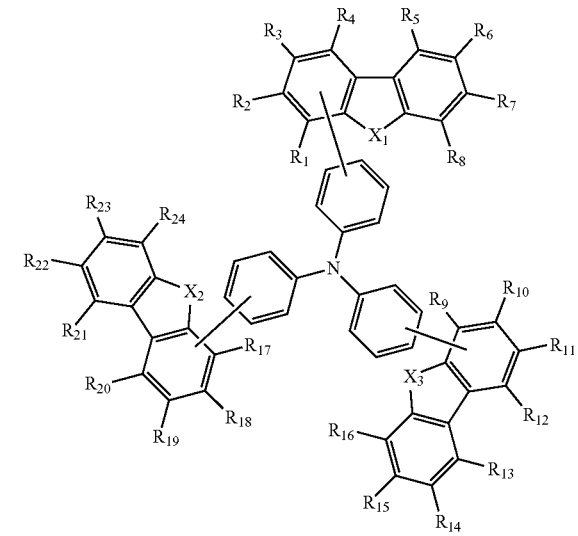

wherein each of $R_1$ to $R_{24}$ is independently hydrogen, deuterium, tritium, silyl group, $C_1$~$C_{20}$ alkyl group, $C_1$~$C_{20}$ alkoxy group, $C_1$~$C_{20}$ alkyl amino group, $C_5$~$C_{30}$ aryl group, $C_4$~$C_{30}$ hetero aryl group, $C_5$~$C_{30}$ alkyl aryl group, $C_4$~$C_{30}$ hetero alkyl aryl group, $C_5$~$C_{30}$ aryloxyl group, $C_4$~$C_{30}$ hetero aryloxyl group, $C_5$~$C_{30}$ aryl amino group or $C_4$~$C_{30}$ hetero aryl amino group, respectively; each of $X_1$, $X_2$ and $X_3$ is independently $CR_{25}R_{26}$, $NR_{27}$, oxygen (O) or sulfur (S), respectively, wherein each of $R_{25}$, $R_{26}$ and $R_{27}$ is independently hydrogen, deuterium, tritium, $C_1$~$C_{20}$ alkyl group or $C_1$~$C_{20}$ alkoxy group,
wherein the second compound comprises any one of the following structures of Chemical Formula 7 or Chemical Formula 8:

Chemical Formula 7
FD-1 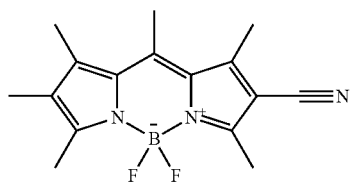
FD-2 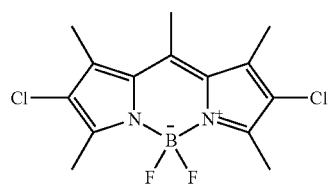
FD-3 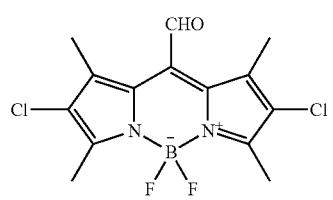
FD-4 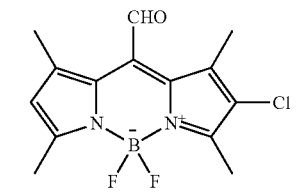
FD-5 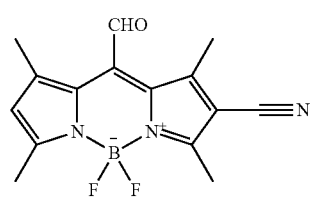
Chemical Formula 8
PD-1 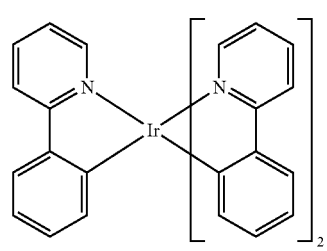
PD-2 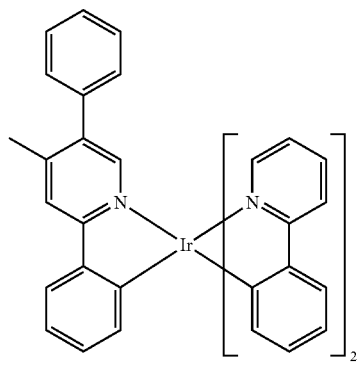
PD-3 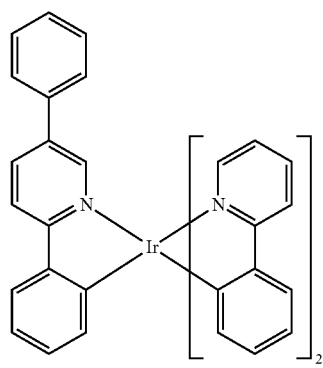
PD-4 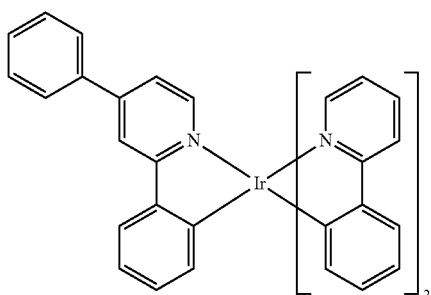
PD-5 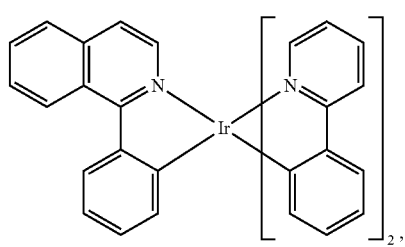
wherein the third compound includes a compound TH-49, TH-50, TH-51 or TH-52, or an organic compound having the following structure of Chemical Formula 3:

TH-49

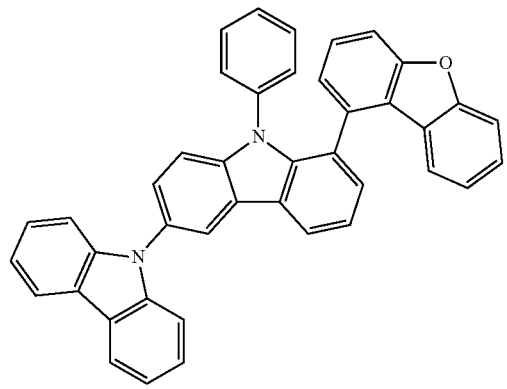

TH-50

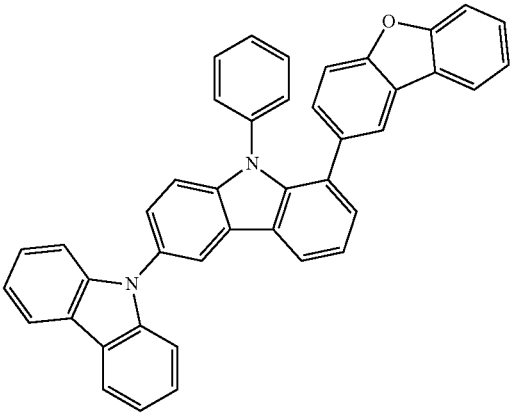

TH-51

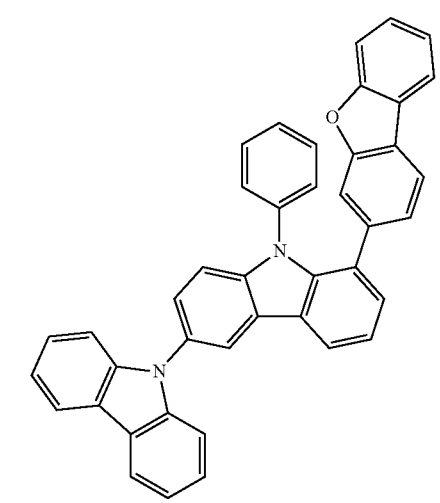

TH-52

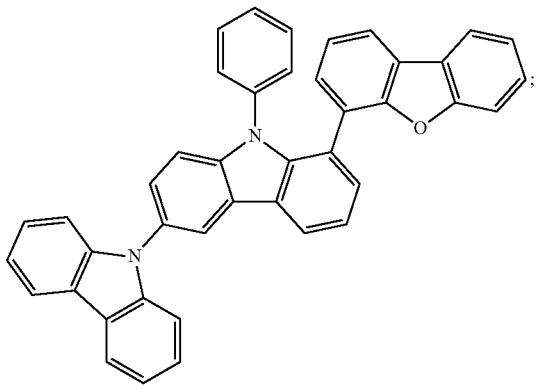

Chemical Formula 3

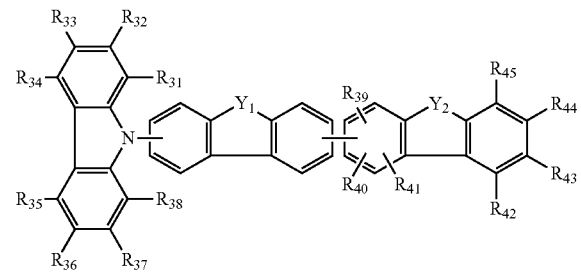

wherein each of $R_{31}$ to $R_{45}$ is independently hydrogen, deuterium, tritium, silyl group, $C_1$~$C_{10}$ alkyl group, $C_1$~$C_{10}$ alkoxy group, $C_1$~$C_{10}$ alkyl amino group, $C_5$~$C_{30}$ aryl group, $C_4$~$C_{30}$ hetero aryl group, $C_5$~$C_{30}$ alkyl aryl group, $C_4$~$C_{30}$ hetero alkyl aryl group, $C_5$~$C_{30}$ aryloxyl group, $C_4$~$C_{30}$ hetero aryloxyl group, $C_5$~$C_{30}$ aryl amino group or $C_4$~$C_{30}$ hetero aryl amino group, or adjacent two groups among $R_{31}$ to $R_{45}$ forms a fused aryl ring or a fused hetero aryl ring each of which is unsubstituted or substituted with $C_5$~$C_{30}$ aryl group or $C_4$~$C_{30}$ hetero aryl group; each of $Y_1$ and $Y_2$ is independently $NR_{46}$, oxygen (O) or sulfur (S), wherein $R_{46}$ is hydrogen, deuterium, tritium, $C_1$~$C_{20}$ alkyl group or $C_1$~$C_{20}$ alkoxy group, and wherein the fourth compound comprises any one of the following structures of Chemical Formula 9:

Chemical Formula 9

TD-1

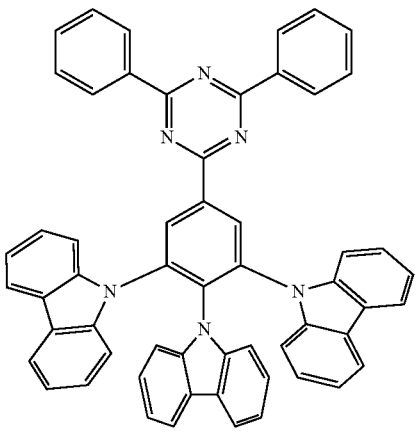

TD-2

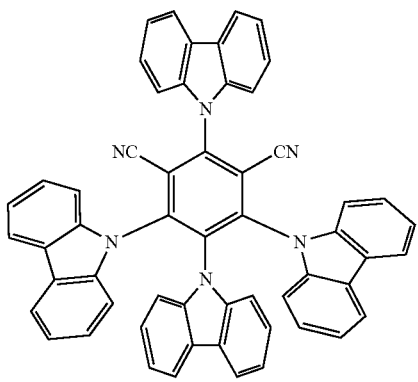

TD-3

TD-4

TD-5

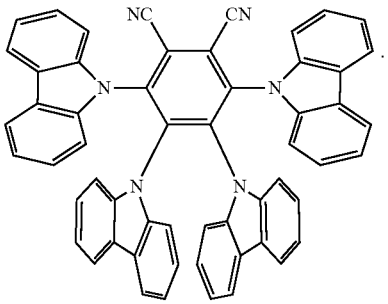

2. The organic light emitting diode of claim 1, wherein a Lowest Unoccupied Molecular Orbital (LUMO) energy level of the third compound is higher than a LUMO energy level of the fourth compound.

3. The organic light emitting diode of claim 2, wherein a HOMO energy level of the third compound is lower than a HOMO energy level of the fourth compound.

4. The organic light emitting diode of claim 1, wherein a HOMO energy level and a Lowest Unoccupied Molecular Orbital (LUMO) energy level of the first compound are each higher than a HOMO energy level and a LUMO energy level of the third compound, respectively.

5. The organic light emitting diode of claim 1, wherein an energy level bandgap between the excited state singlet energy level and the excited state triplet energy level of the fourth compound is equal to or less than about 0.3 eV.

6. The organic light emitting diode of claim 1, further comprising a third emitting material layer disposed between the second emitting material layer and the second electrode, wherein the third emitting material layer comprises a fifth compound and a sixth compound.

7. The organic light emitting diode of claim 6, wherein an excited state singlet energy level of the fifth compound is higher than an excited state singlet energy level of the sixth compound.

8. The organic light emitting diode of claim 1, wherein the third compound comprises an organic compound having the flowing structure of Chemical Formula 4 or Chemical Formula 5:

Chemical Formula 4

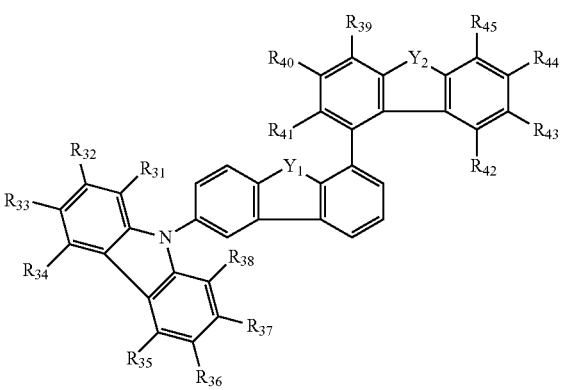

Chemical Formula 5

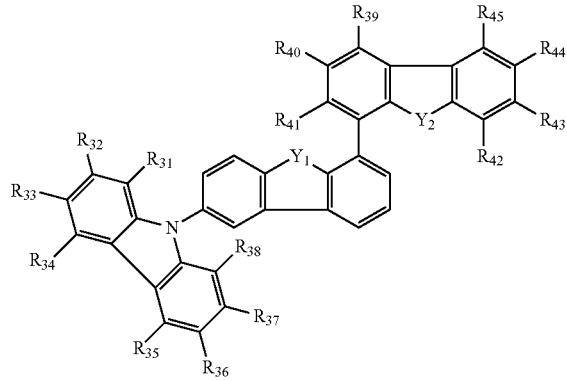

wherein each of $R_{31}$ to $R_{45}$, $Y_1$ and $Y_2$ is identical as defined in Chemical Formula 3, respectively.

9. An organic light emitting device, comprising:
a substrate; and
the organic light emitting diode according to claim 1 disposed over the substrate.

10. The organic light emitting device of claim 9, wherein the organic light emitting device comprises an organic light emitting display device.

11. The organic light emitting diode of claim 1, wherein the first compound is selected from any one of the following structures:

FH-1

FH-2

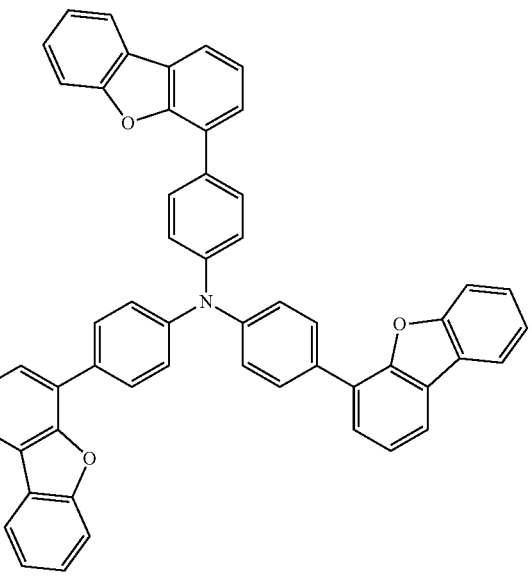

FH-3

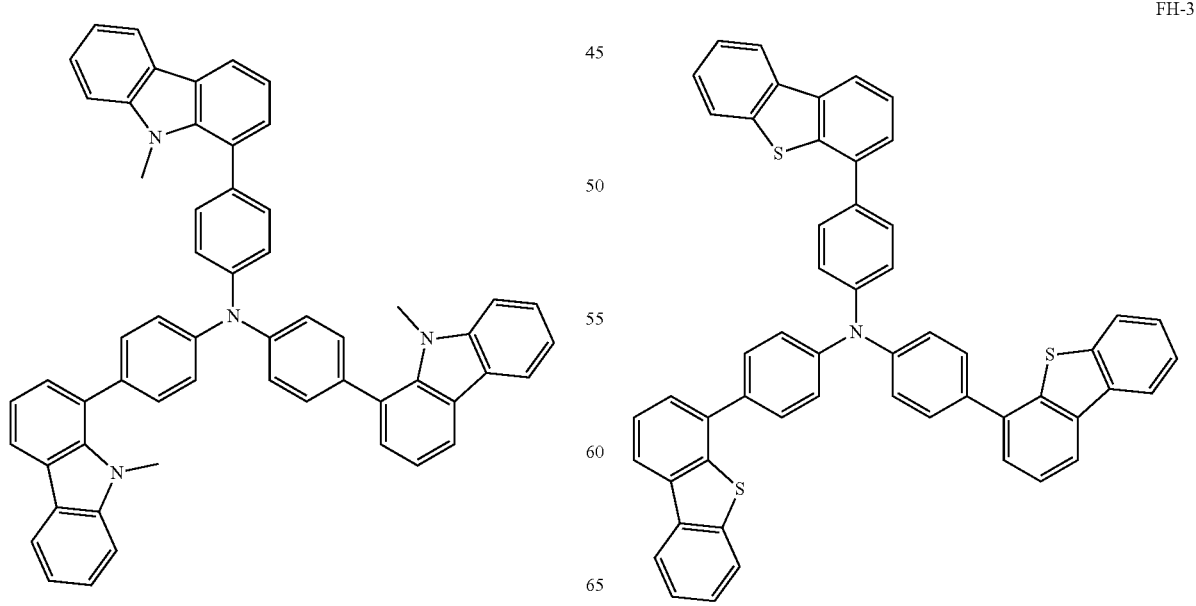

FH-4
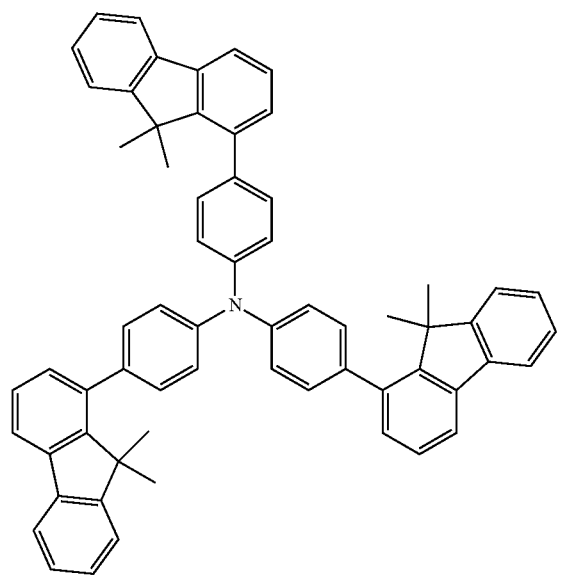
FH-6
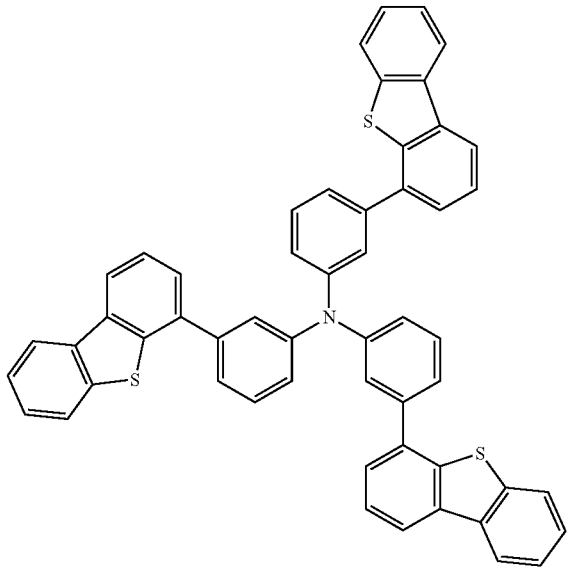
FH-5
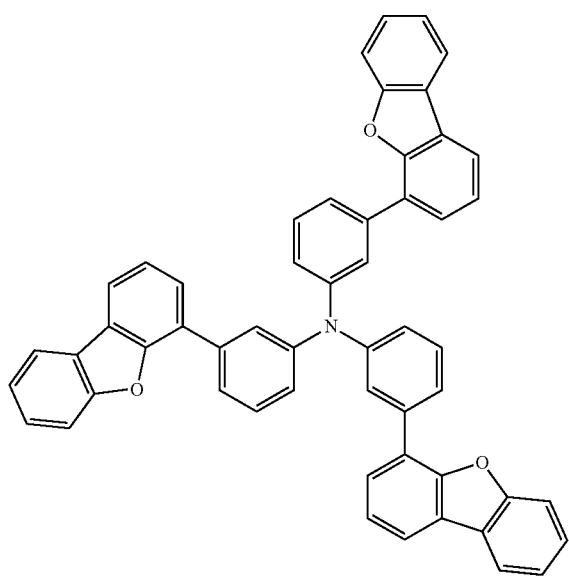
FH-7
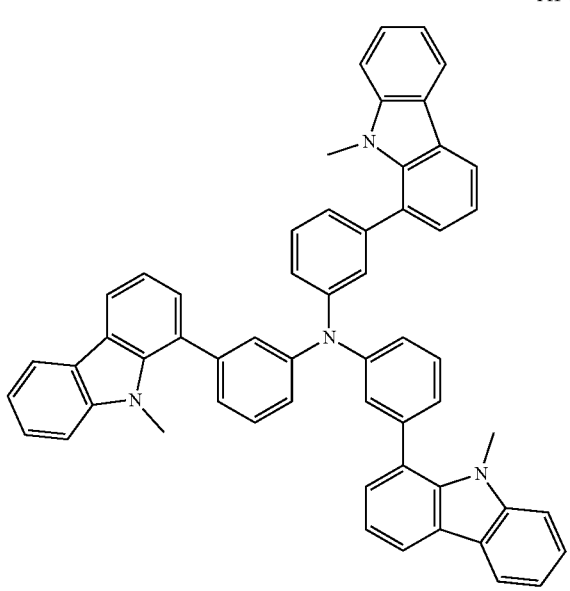

FH-8
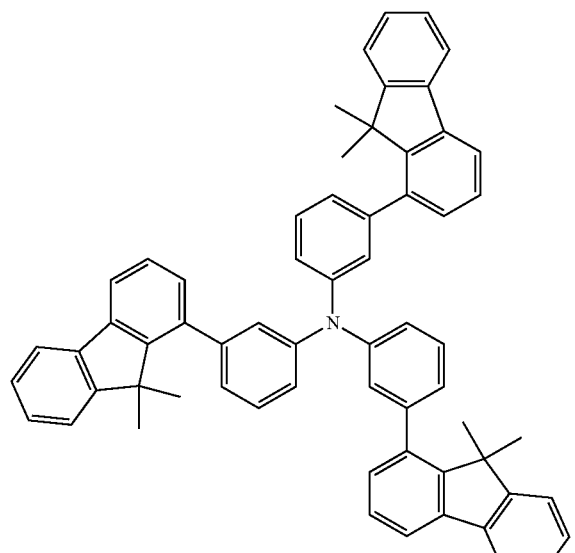
FH-9
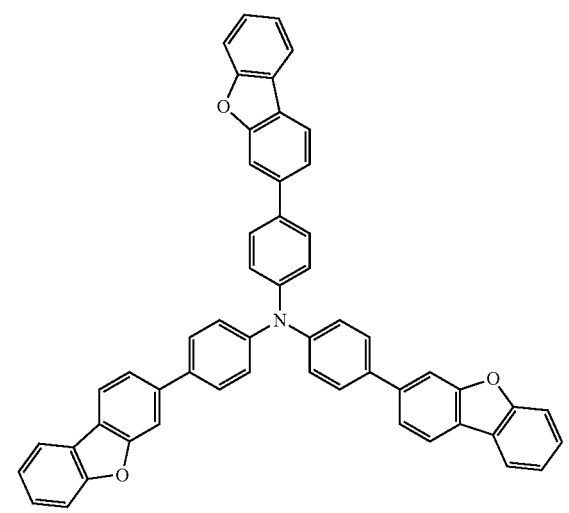
FH-10
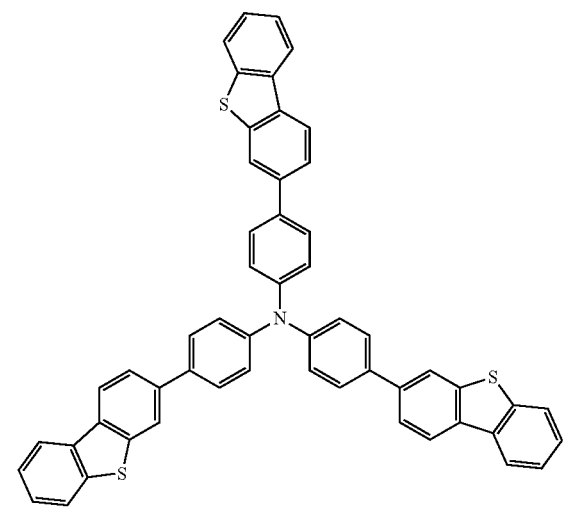
FH-11
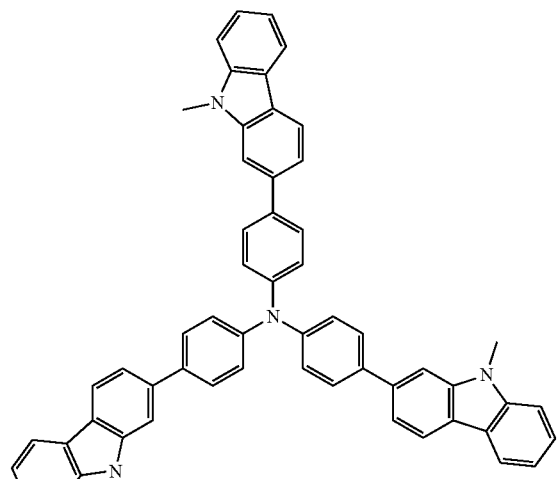
FH-12
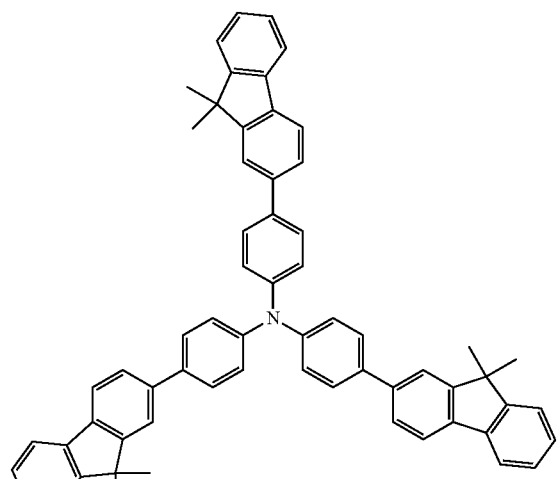
FH-13
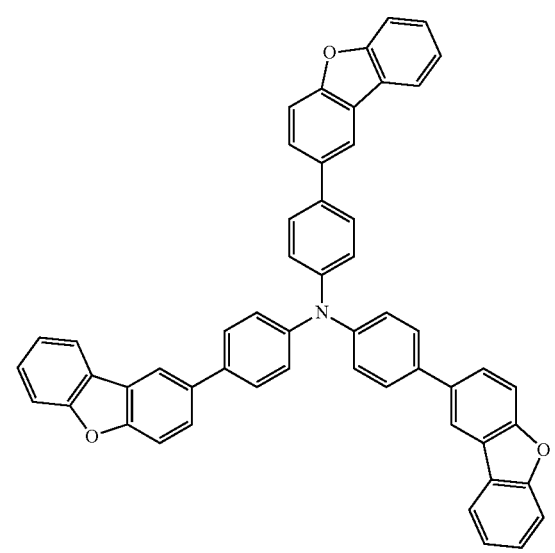

FH-14
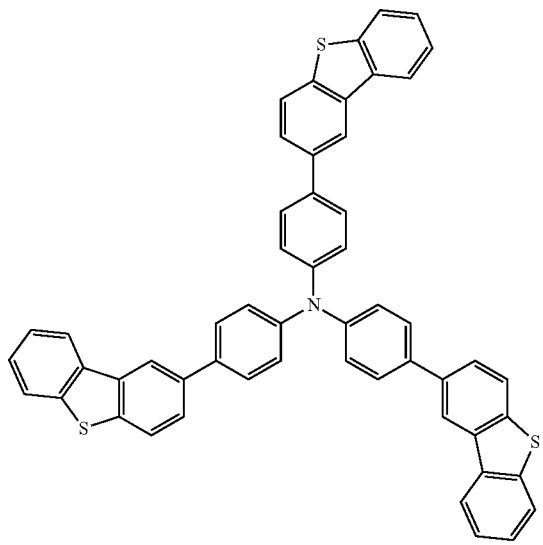
FH-15
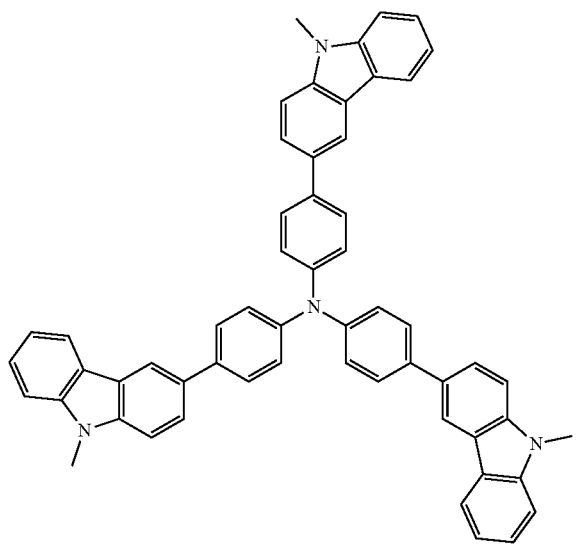
FH-16
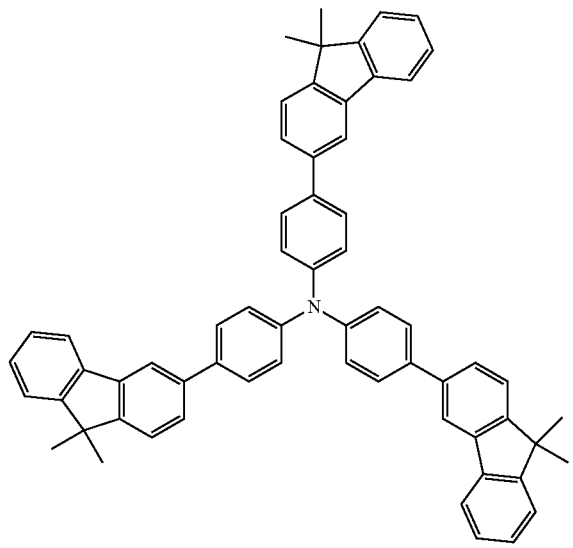
FH-17
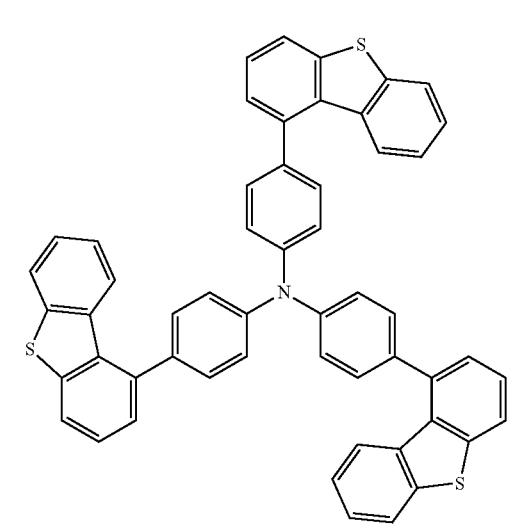
FH-18

FH-19
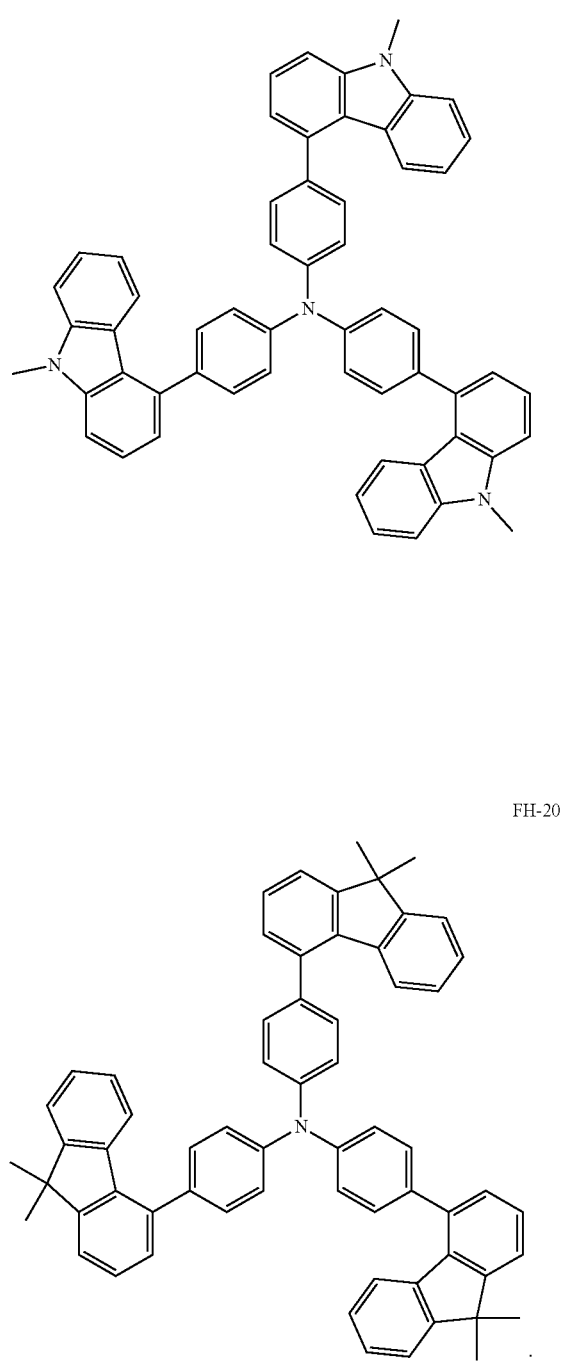
FH-20
TH-1
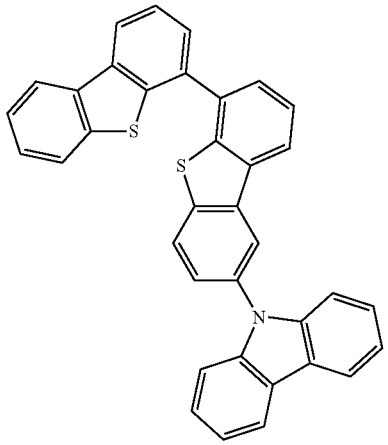
TH-2
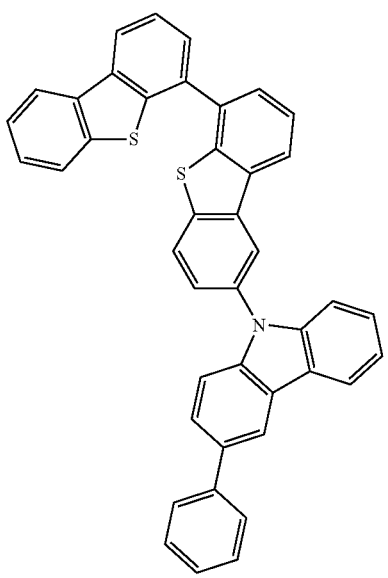
TH-3
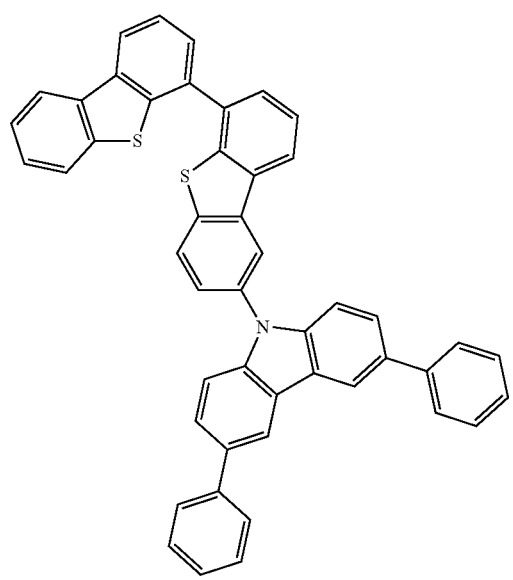
12. The organic light emitting diode of claim 1, wherein the third compound is selected from any one of the following structures:

TH-4
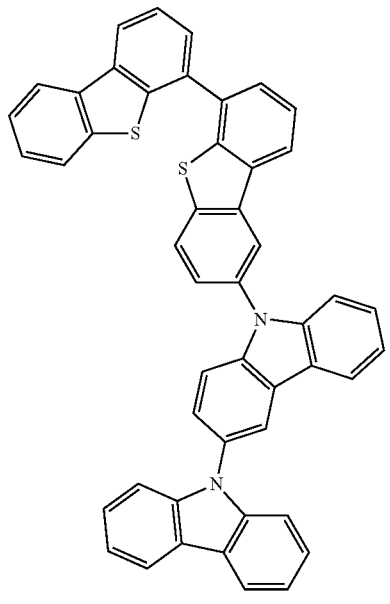
TH-6
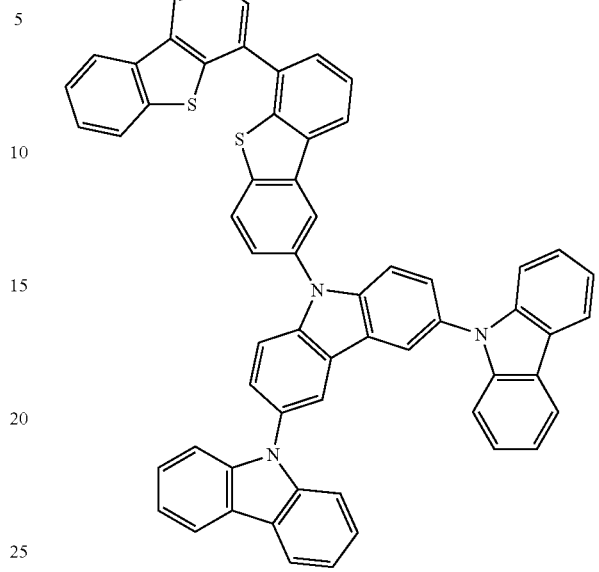
TH-7
TH-5
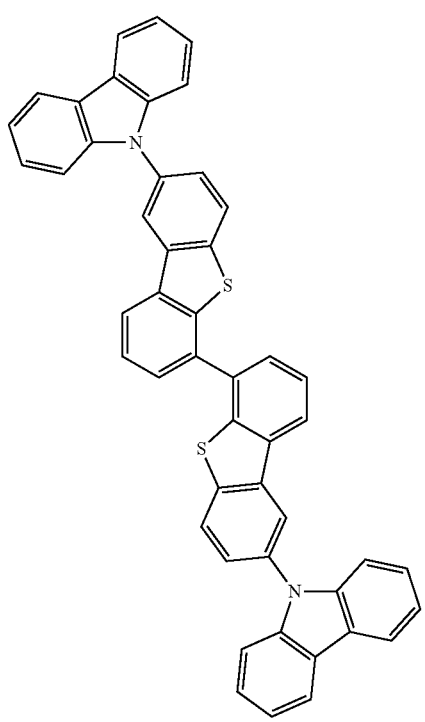
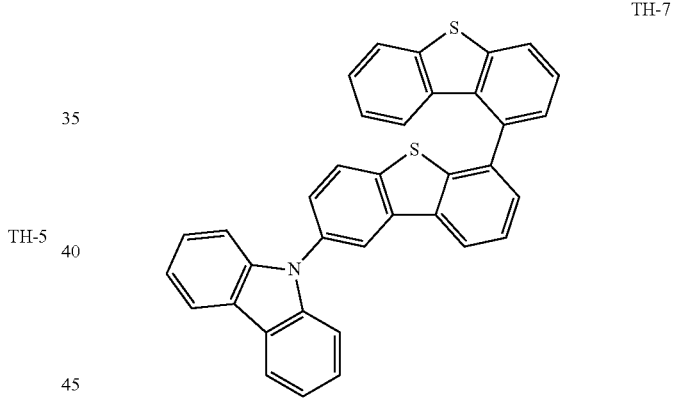
TH-8
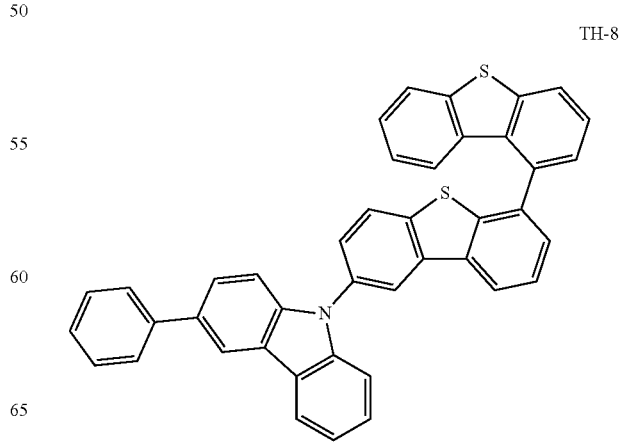

TH-9
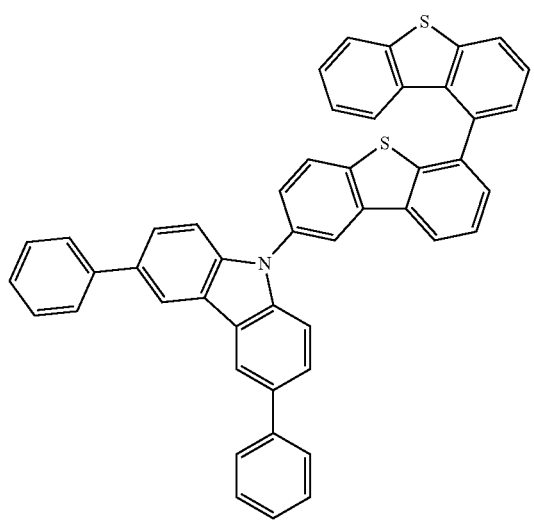
TH-10
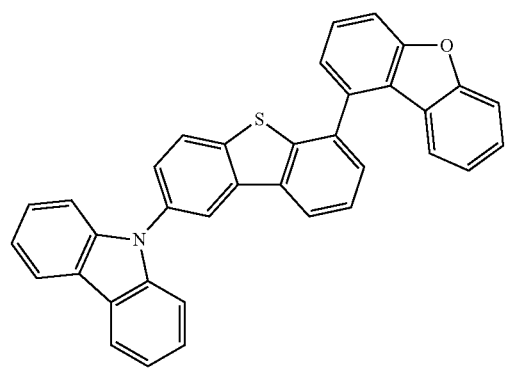
TH-11
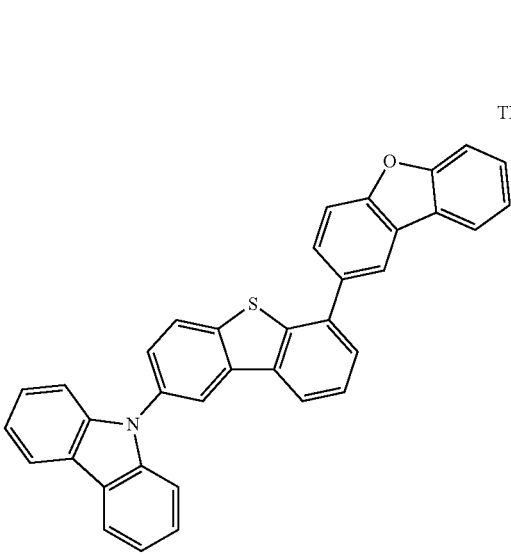
TH-12
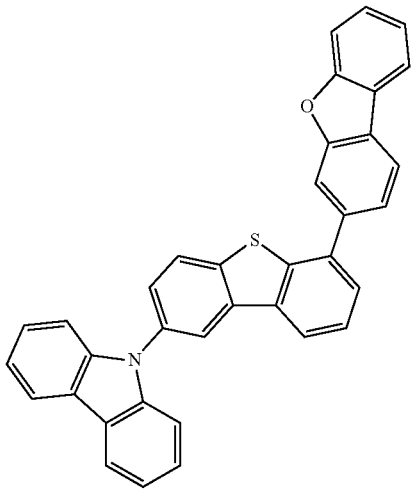
TH-13
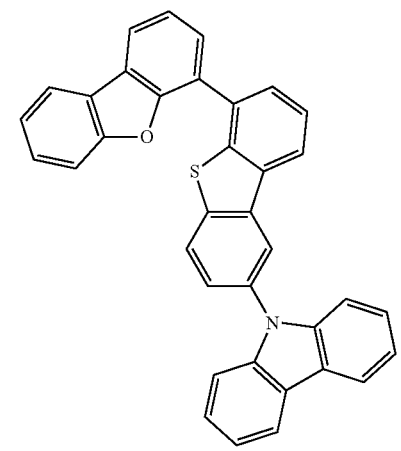
TH-14
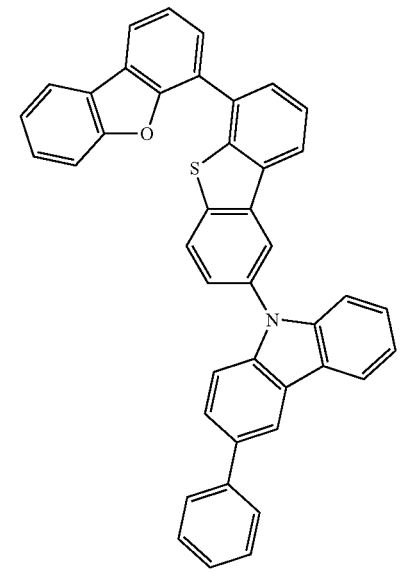

TH-15
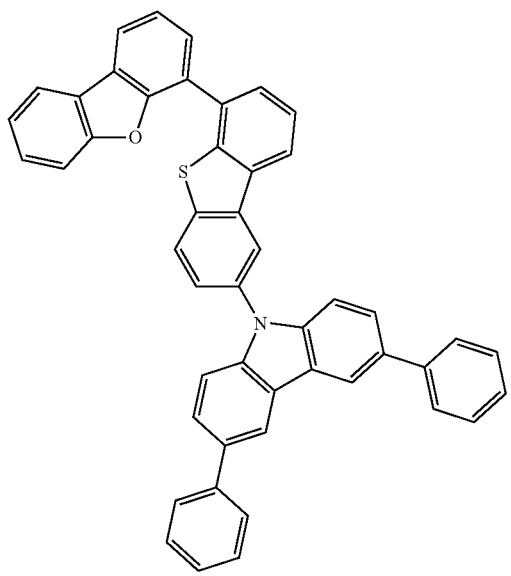
TH-16
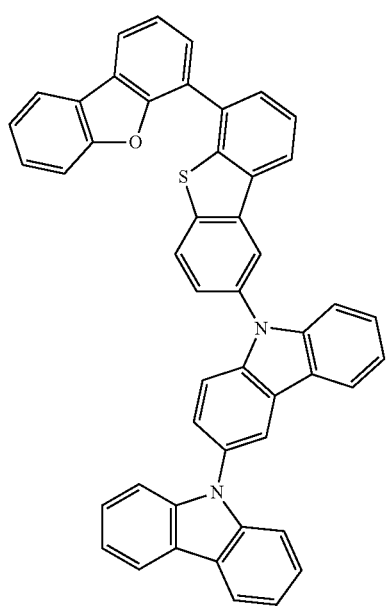
TH-17
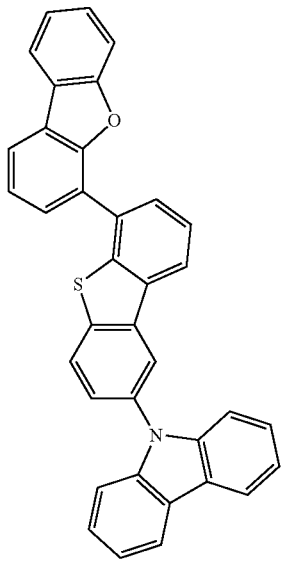
TH-18
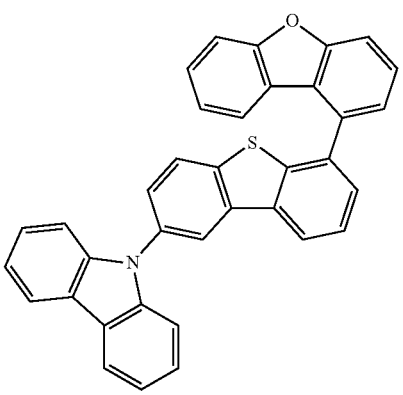
TH-19

TH-20
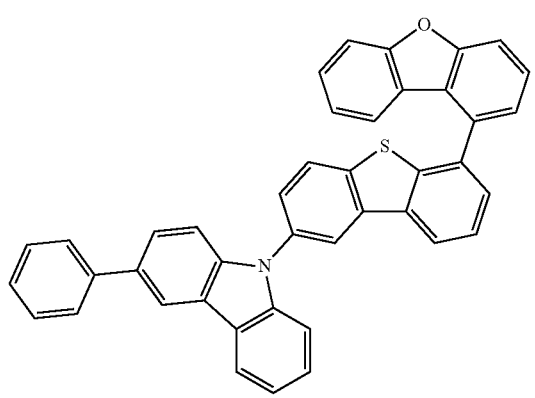
TH-23
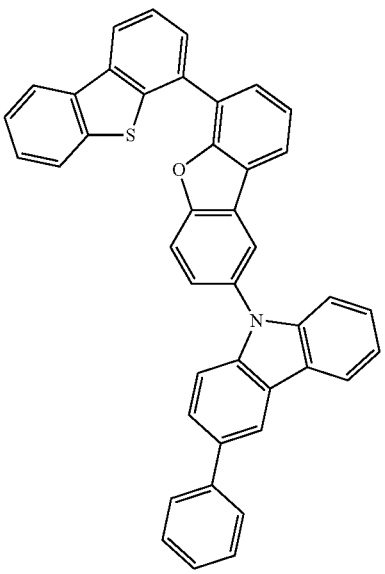
TH-21
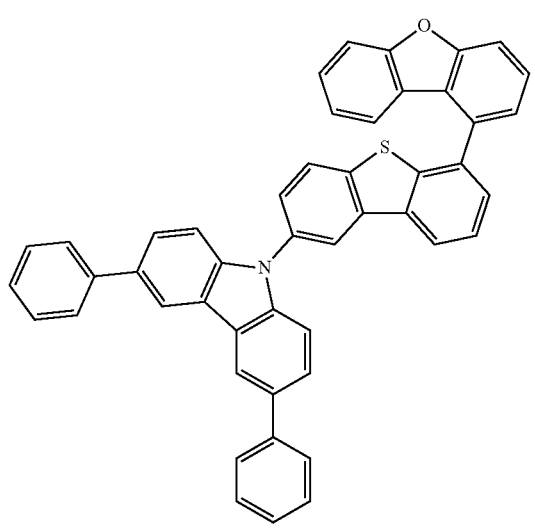
TH-22
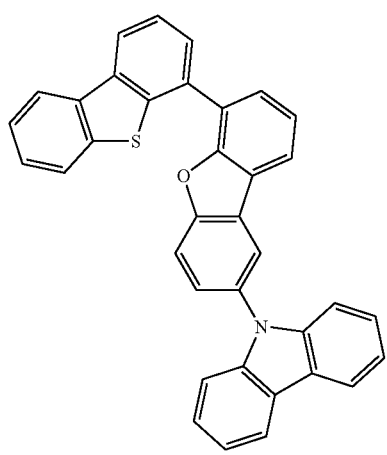
TH-24
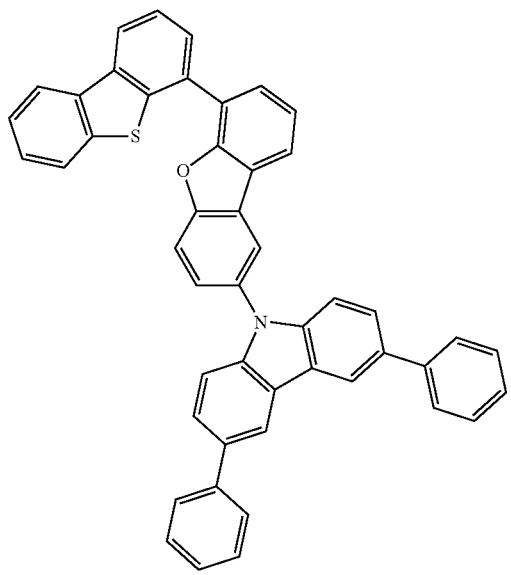

TH-25
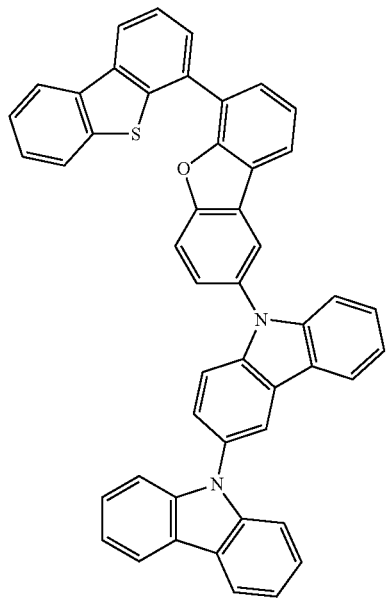
TH-26
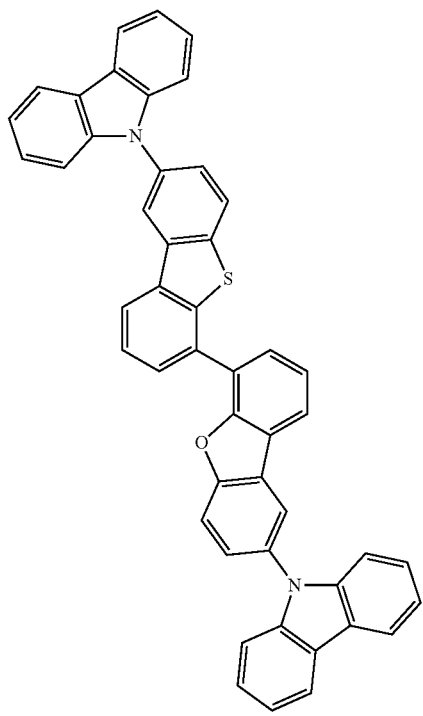
TH-27
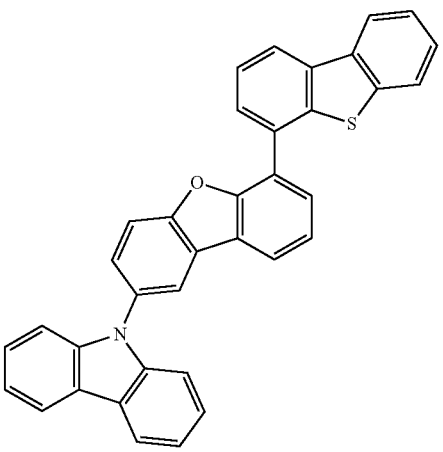
TH-28
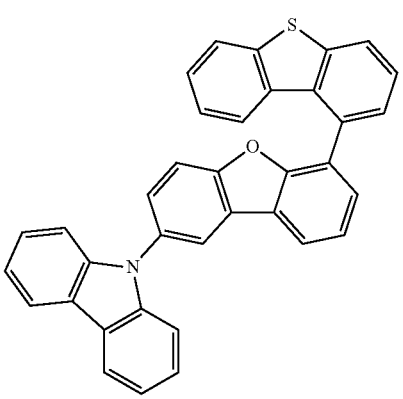
TH-29
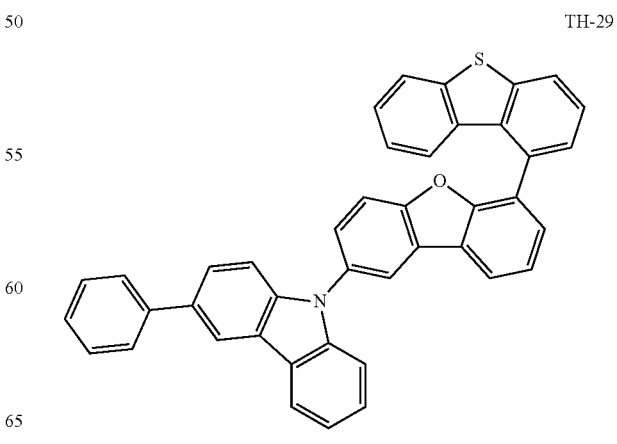

TH-30
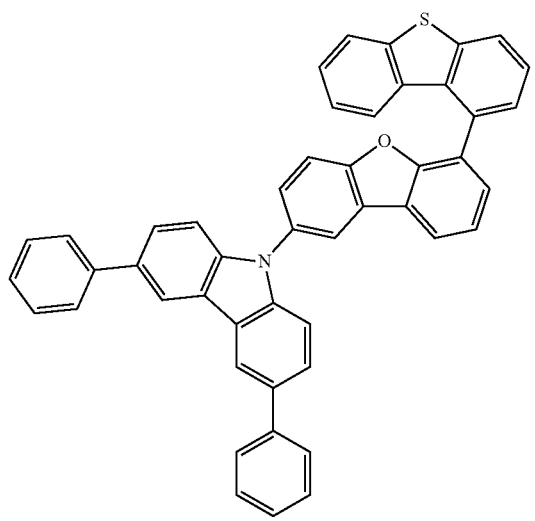
TH-31
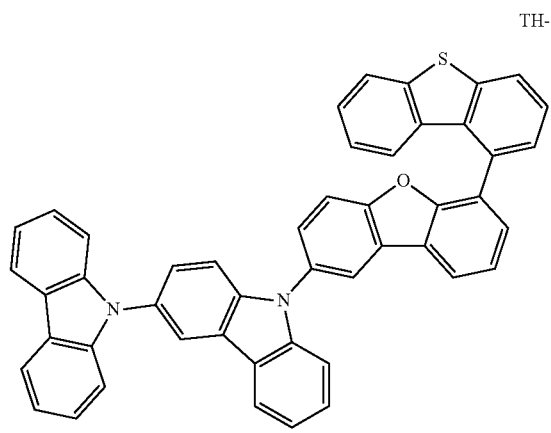
TH-32
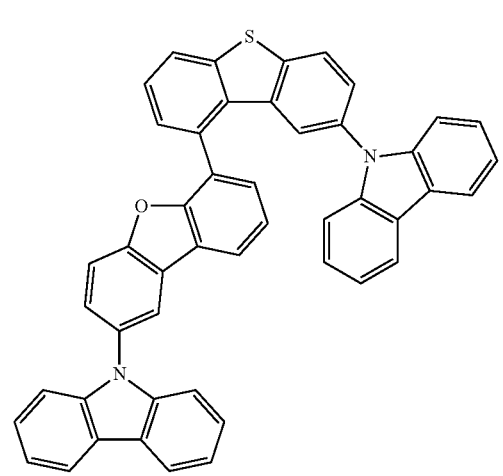
TH-33
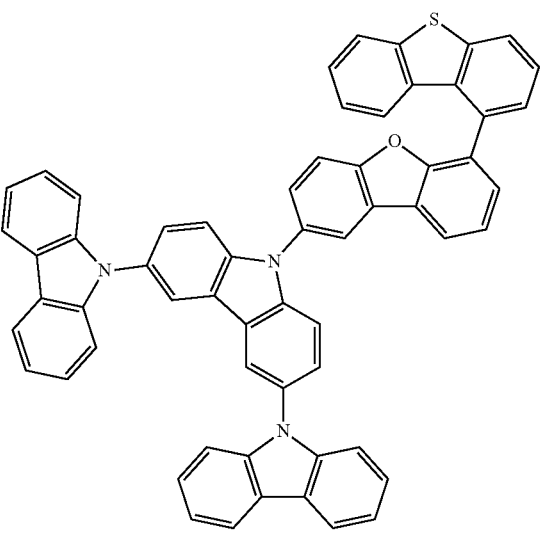
TH-34
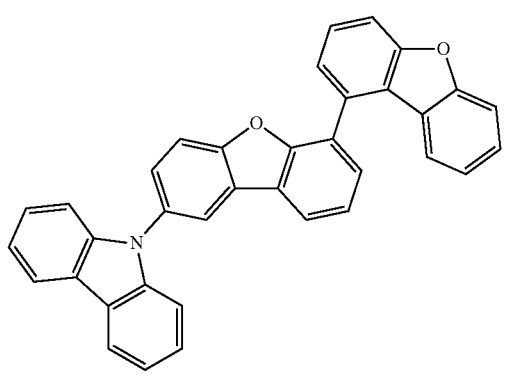
TH-35
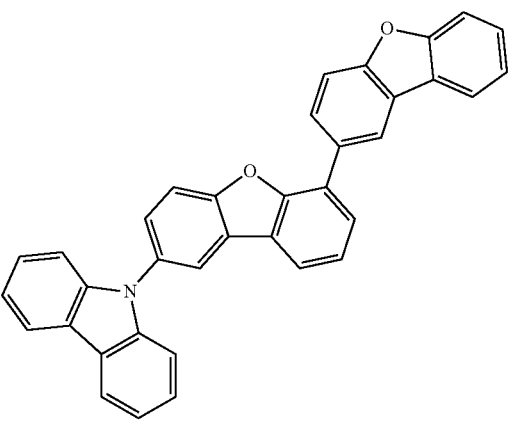

TH-36
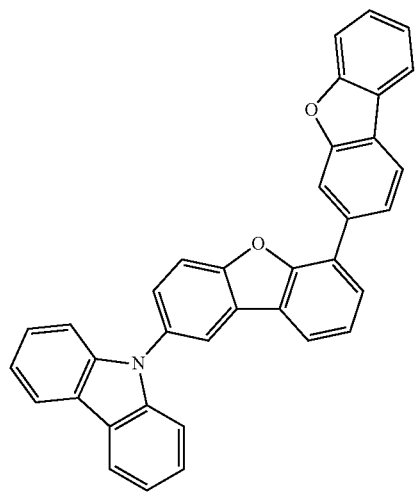
TH-37
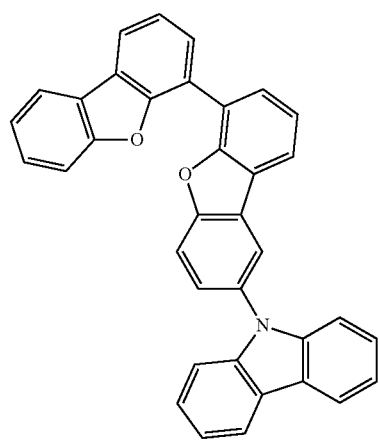
TH-38
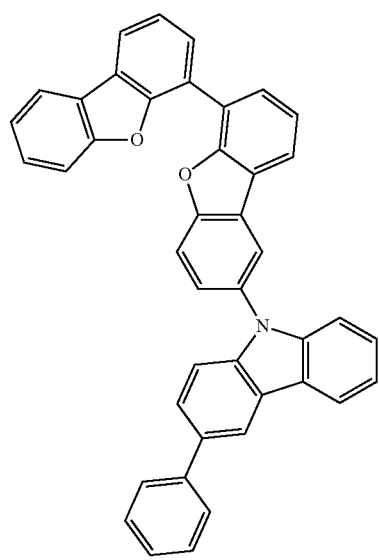
TH-39
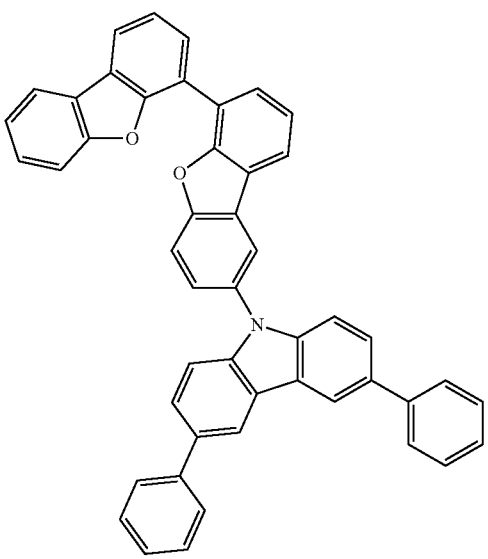
TH-40
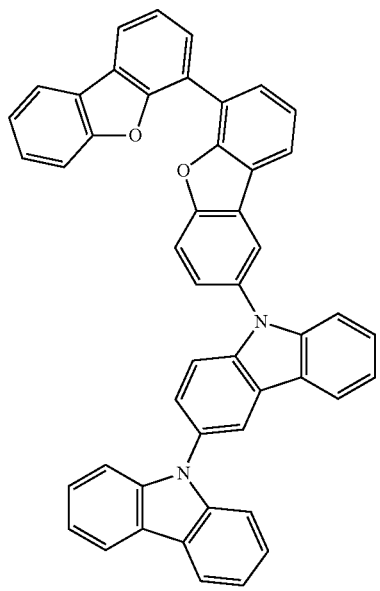

TH-41
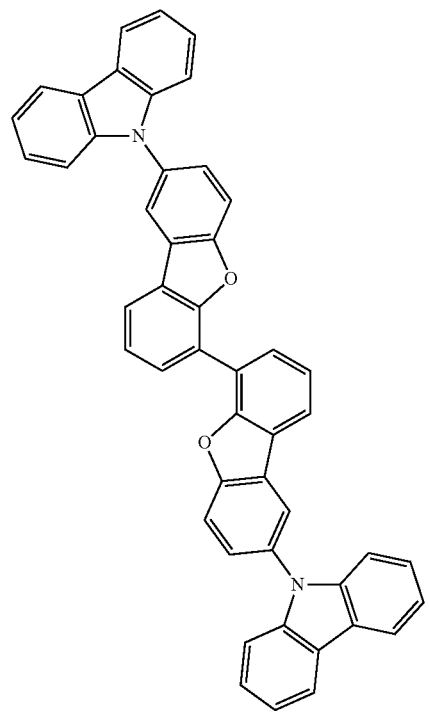
TH-42
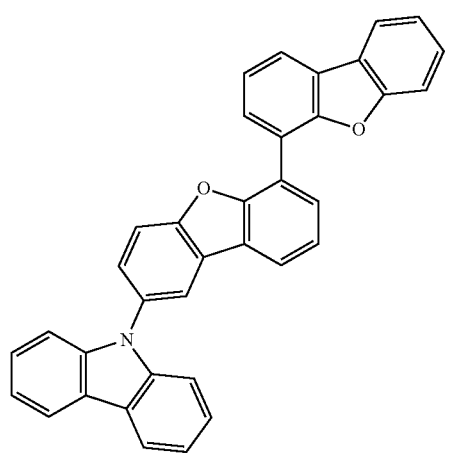
TH-43
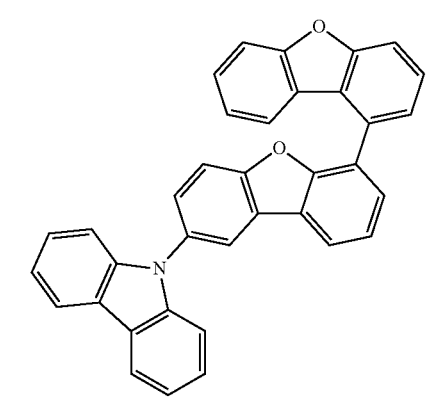
TH-44
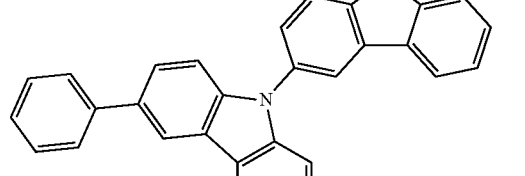
TH-45
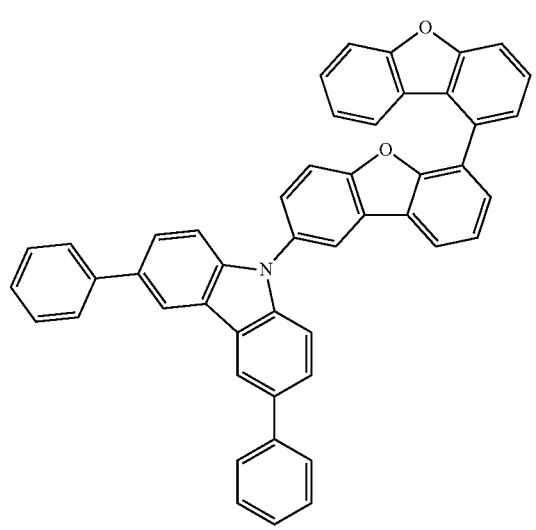
TH-46
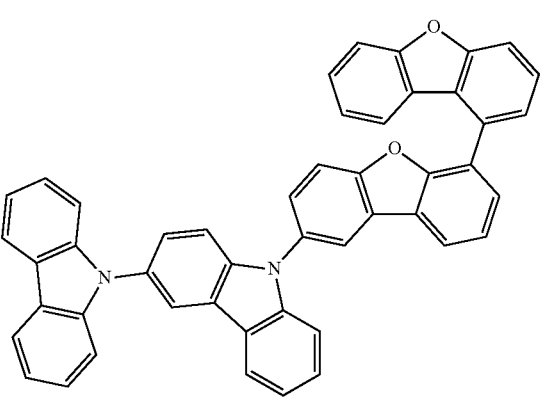

TH-47
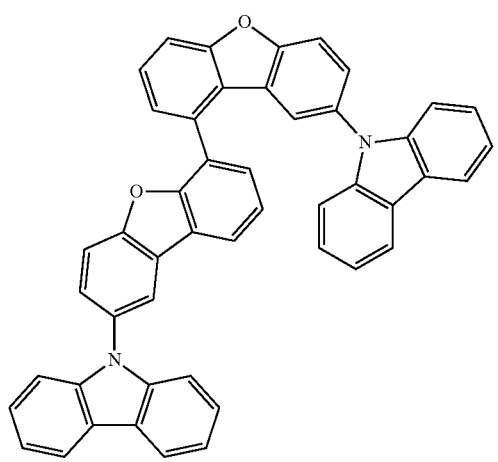
TH-48
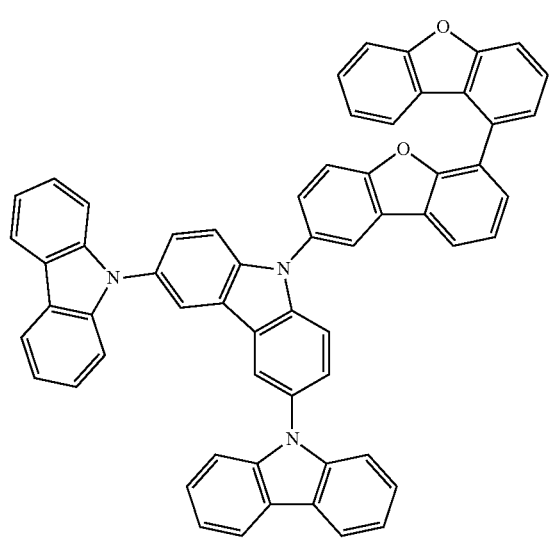
TH-49
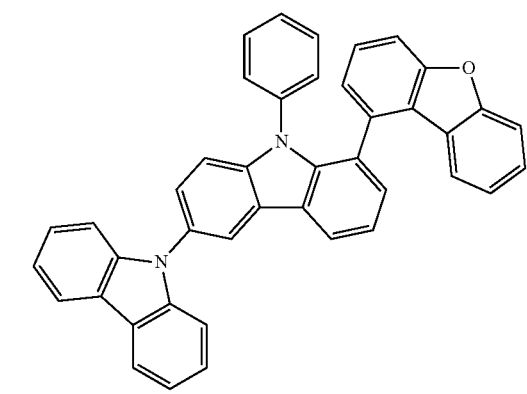
TH-50
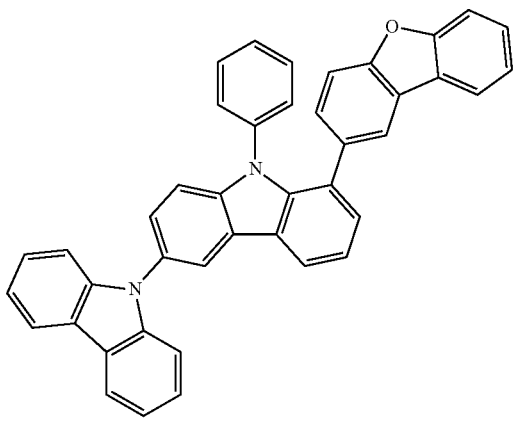
TH-51
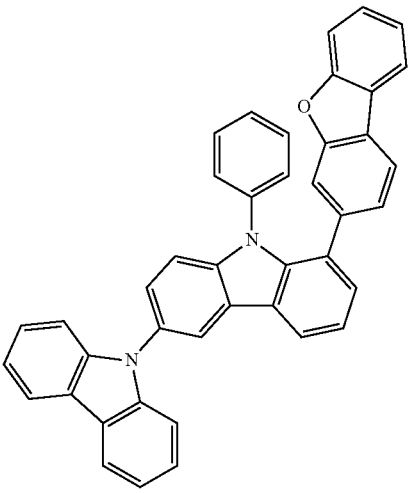
TH-52
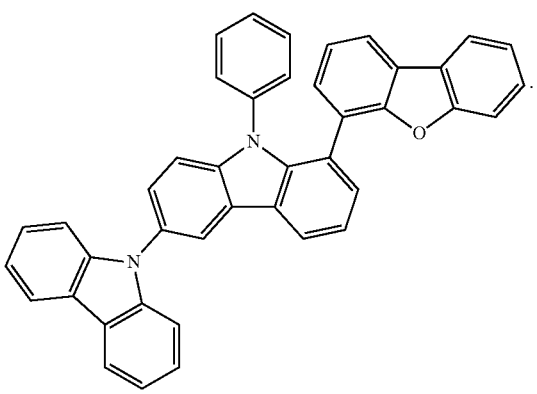
* * * * *